United States Patent
Heatherington

(10) Patent No.: US 12,409,288 B2
(45) Date of Patent: Sep. 9, 2025

(54) RESPIRATORY MASK ASSEMBLY FOR USE WITH CONTINUOUS POSITIVE AIRWAY PRESSURE (CPAP) EQUIPMENT

(71) Applicant: SNAP CPAP, LLC, Chapel Hill, NC (US)

(72) Inventor: Stuart Heatherington, Chapel Hill, NC (US)

(73) Assignee: SNAP CPAP, LLC, Chapel Hill, NC (US)

( * ) Notice: Subject to any disclaimer, the term of this patent is extended or adjusted under 35 U.S.C. 154(b) by 1000 days.

(21) Appl. No.: 17/197,135

(22) Filed: Mar. 10, 2021

(65) Prior Publication Data
US 2021/0290881 A1 Sep. 23, 2021

Related U.S. Application Data

(63) Continuation of application No. PCT/US2021/021430, filed on Mar. 9, 2021.
(Continued)

(51) Int. Cl.
*A61M 16/06* (2006.01)
*A61M 16/08* (2006.01)
*A61M 16/10* (2006.01)

(52) U.S. Cl.
CPC .... *A61M 16/0616* (2014.02); *A61M 16/0666* (2013.01); *A61M 16/0816* (2013.01);
(Continued)

(58) Field of Classification Search
CPC ...... A61M 2205/0272; A61M 16/0616; A61M 16/0666; A61M 16/0816; A61M 16/105; A61M 16/06
See application file for complete search history.

(56) References Cited

U.S. PATENT DOCUMENTS

| 3,225,982 A | 12/1965 | Melton |
| 3,613,678 A * | 10/1971 | Mayhew ............ A41D 13/1115 |
| | | 128/206.19 |

(Continued)

FOREIGN PATENT DOCUMENTS

| JP | 2006505373 A | 2/2006 |
| JP | 2014000398 A | 1/2014 |

(Continued)

OTHER PUBLICATIONS

Machine English Translation of KR 101758652 B1 (accessed on Nov. 18, 2024).*

(Continued)

*Primary Examiner* — Kendra D Carter
*Assistant Examiner* — Maap Ellabib
(74) *Attorney, Agent, or Firm* — NK Patent Law

(57) ABSTRACT

Respiratory assembly for use in conjunction with a continuous positive airway pressure (CPAP) equipment is provided. The respiratory assembly includes a conduit coupler comprising a male member and a female member. The respiratory assembly also includes a disposable respiratory mask that defines a central opening therethrough that is sized to receive the male member. A gasket is positioned between the male member and the respiratory mask, the gasket encircling the central opening to provide a sealing thereto. A channel opening of one of the male member and the female member connects to a continuous positive airway pressure (CPAP) mask that couples to one or more of a patient's nare and mouth.

12 Claims, 38 Drawing Sheets

Related U.S. Application Data

(60) Provisional application No. 62/993,220, filed on Mar. 23, 2020, provisional application No. 62/992,966, filed on Mar. 21, 2020.

(52) U.S. Cl.
CPC ... *A61M 16/105* (2013.01); *A61M 2205/0272* (2013.01); *A61M 2207/00* (2013.01)

(56) References Cited

U.S. PATENT DOCUMENTS

| | | | |
|---|---|---|---|
| 5,676,133 | A | 10/1997 | Hickle et al. |
| 5,806,898 | A | 9/1998 | Hollnagle |
| 6,196,223 | B1 | 3/2001 | Belfer et al. |
| 7,229,516 | B2 * | 6/2007 | Busby .................. B32B 27/04 156/247 |
| 7,730,847 | B1 | 6/2010 | Redd |
| 7,997,267 | B2 | 8/2011 | Ging |
| 8,887,725 | B2 | 11/2014 | Hernandez et al. |
| 9,517,317 | B2 | 12/2016 | McAuley et al. |
| 9,981,104 | B1 | 5/2018 | Groll et al. |
| 10,265,493 | B2 | 4/2019 | Heatherington |
| 2003/0047189 | A1 * | 3/2003 | Kumar .................. A61M 16/06 128/206.29 |
| 2004/0031490 | A1 * | 2/2004 | Haaga .................. A41D 13/11 128/206.19 |
| 2006/0217665 | A1 | 9/2006 | Prosek |
| 2007/0095348 | A1 | 5/2007 | Fisher et al. |
| 2007/0163600 | A1 | 7/2007 | Hoffman |
| 2010/0326441 | A1 | 12/2010 | Zucker |
| 2011/0030250 | A1 | 2/2011 | Boyd |
| 2011/0297152 | A1 * | 12/2011 | Duveen ................ A61M 16/06 128/203.29 |
| 2013/0131534 | A1 | 5/2013 | Heatherington |
| 2013/0263858 | A1 | 10/2013 | Ho et al. |
| 2014/0090649 | A1 * | 4/2014 | Groll .................... A61M 16/06 128/205.25 |
| 2015/0075530 | A1 | 3/2015 | Collazo et al. |
| 2015/0250972 | A1 | 9/2015 | Haibach et al. |
| 2015/0335846 | A1 | 11/2015 | Romagnoli |
| 2016/0022947 | A1 * | 1/2016 | Heatherington .. A61M 16/0825 128/205.25 |
| 2017/0368291 | A1 | 12/2017 | Heatherington |
| 2018/0110945 | A1 | 4/2018 | Cheng et al. |
| 2018/0296785 | A1 | 10/2018 | Heatherington |
| 2019/0125998 | A1 | 5/2019 | Baiko et al. |
| 2019/0175863 | A1 | 6/2019 | Hocking et al. |

FOREIGN PATENT DOCUMENTS

| | | | | |
|---|---|---|---|---|
| JP | 2018530389 | A | 10/2018 | |
| KR | 101758652 | B1 * | 7/2017 | ............ A61M 16/06 |
| WO | 2009117163 | A1 | 9/2009 | |
| WO | 2011030250 | A1 | 3/2011 | |
| WO | 2012085758 | A1 | 6/2012 | |
| WO | 2014045245 | A1 | 3/2014 | |
| WO | 2014120271 | A1 | 8/2014 | |

OTHER PUBLICATIONS

ISA/KR, International Search Report and Written Opinion for corresponding PCT Patent Application No. PCT/US2021/021430, mailed Jul. 2, 2021, 9 pages.
Valfort, Cyril, Annex to European Search Report dated May 22, 2023, for corresponding EP Patent Application No. 20815110.0.
JPO, Office Action for corresponding Japanese Patent Application No. 2022-502104, mailed Jan. 9, 2024, 9 pages (including English translation).
EPO, Extended European Search Report for related European Patent Application No. 24172705.6, mailed Jun. 20, 2024, 5 pages.
WIPO; International Preliminary Report on Patentability for International Patent Application No. PCT/US2021/021430 dated Oct. 6, 2022, 7 pages.
IP India, Hearing Notice for corresponding Indian Patent Application No. 201827011815, mailed Mar. 18, 2024, 3 pages.
JPO, Office Action for corresponding Japanese Patent Application No. 2022-519753, mailed Mar. 5, 2024, 5 pages including translation.
EPO, Extended European Search Report for European Patent Application No. 21775939.8, dated Mar. 25, 2024, 12 pages.
JPO, Office Action for corresponding Japanese Patent Application No. 2022-556558, dated Sep. 17, 2024, 9 pages.
USPTO, Non-Final Office Action for corresponding U.S. Appl. No. 17/538,126, dated Nov. 14, 2024, 15 pages.
IP Australia, Examination Report for Australian Patent Application No. 2020311310, dated Apr. 16, 2025, 4 pages.
USPTO, Non-Final Office Action for U.S. Appl. No. 17/677,436, mailed Nov. 26, 2024, 16 pages.
JPO, Office Action for Japanese Patent Application No. 2024-062829, mailed Feb. 4, 2025, 6 pages (including translation).

\* cited by examiner

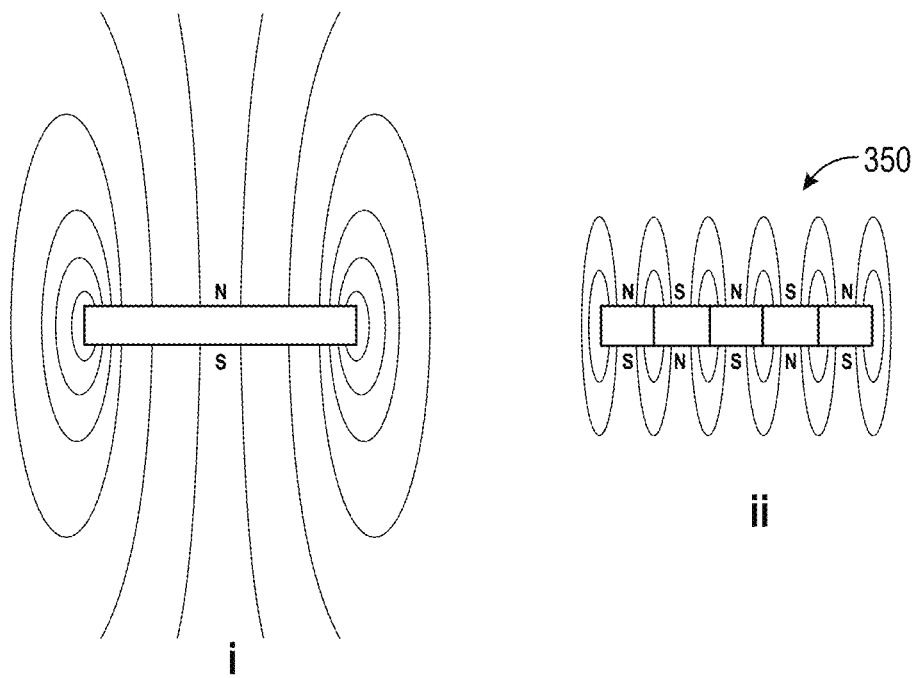
i  FIG. 28C
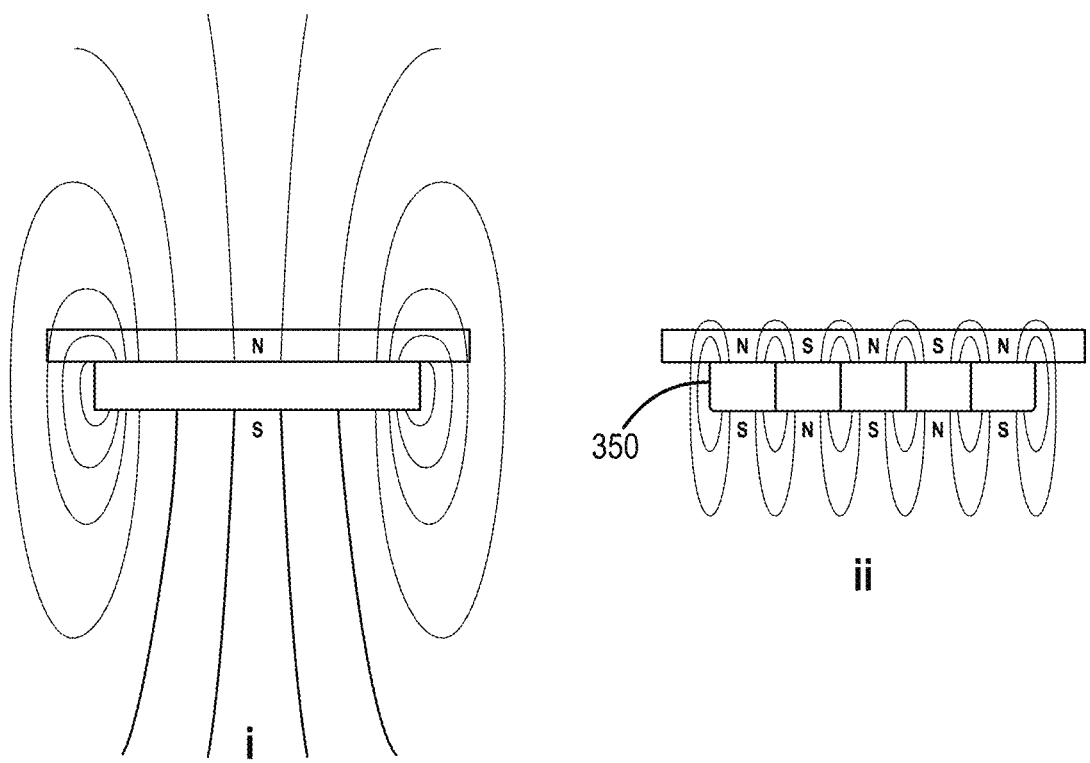
i  FIG. 28D

RESPIRATORY MASK ASSEMBLY FOR USE WITH CONTINUOUS POSITIVE AIRWAY PRESSURE (CPAP) EQUIPMENT

CROSS-REFERENCE TO RELATED APPLICATIONS

This application is a continuation of PCT Patent Application No. PCT/US2021/021430 entitled "RESPIRATORY MASK ASSEMBLY FOR USE WITH CONTINUOUS POSITIVE AIRWAY PRESSURE (CPAP) EQUIPMENT," which was filed on Mar. 9, 2021, which claims benefit of and priority to U.S. Provisional Patent Application 62/993,220 filed on Mar. 23, 2020, and to U.S. Provisional Patent Application 62/992,966 filed on Mar. 21, 2020, the entire contents of which are hereby incorporated by reference in their entirety.

TECHNICAL FIELD

The presently disclosed subject matter relates to a respiratory assembly, and particularly to a respiratory mask assembly for use in conjunction with continuous positive airway pressure (CPAP) equipment.

BACKGROUND

Facial masks and nasal cannula are typically used for treating individuals with breathing difficulties or otherwise in need of positive breathing air supply. High flow delivery of respirator gas can be delivered using a nasal cannula and/or a facial mask. Continuous positive airway pressure (CPAP) masks can deliver a treatment fluid such as ambient air, oxygen-enriched air, a gas, a mixture of gases, or a gas with a medication to a patient under a predetermined or desired pressure setting. Alternately, maskless respiratory assemblies can be used to deliver such fluids.

It may be beneficial for a patient connected to CPAP equipment to wear a respiratory mask such as a N95 respirator, a surgical mask, or a similar other face mask (hereinafter generally referred to as a "respiratory mask") to protect the wearer from airborne particles such as microbes such as, for example, bacteria and virus. Alternately, in instances where the patient is suffering from a communicable disease, a respiratory mask worn by the patient can reduce or eliminate the spread of the communicable disease to medical professionals, caretakers, relatives of the patient, and other patients that may be in the vicinity of the patient. However, it would not be practicable or possible for a person/patient connected a continuous positive airway pressure (CPAP) equipment to wear a respiratory mask at the same time.

Accordingly, it would be beneficial to provide an improvement that addresses the above-noted disadvantages.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Provided herein is a respiratory assembly for use in conjunction with a continuous positive airway pressure (CPAP) equipment. According to various embodiments, the respiratory assembly comprises a conduit coupler comprising a male member and a female member. The assembly also comprises a disposable respiratory mask that defines a central opening therethrough that is sized to receive the male member. A gasket is positioned between the male member and the respiratory mask. The gasket encircles the central opening to provide a sealing thereto. A channel opening of one of the male member and the female member connects to a continuous positive airway pressure (CPAP) mask that couples to one or more of a patient's nare and mouth.

According to one or more embodiments, the respiratory mask is configured for blocking at least 95 percent of particles of 0.3-micron size or greater.

According to one or more embodiments, the respiratory mask is a surgical mask.

According to one or more embodiments, the gasket comprises an adhesive foam material.

According to one or more embodiments, the gasket is formed of a stretchable elastomeric material.

According to one or more embodiments, at least one major surface of the gasket comprises a peel-back glue membrane.

According to one or more embodiments, at least one major surface of the gasket comprises a glue material.

According to one or more embodiments, the respiratory assembly comprises two gaskets, wherein each gasket encircles the central opening on each side of a respiratory mask wall.

According to one or more embodiments, the gasket forms an interference fit with the male member.

According to one or more embodiments, the female member selectively engages with the male member.

According to one or more embodiments, the female member screws over threads formed on the male member.

According to one or more embodiments, the female member includes one or more releases that can be pivoted to form a selective engagement with the male member.

According to one or more embodiments, the female member selectively engages the male member with a quick disconnect mechanism.

According to one or more embodiments, the channel opening of another of the male member and the female member receives a flexible tubing connected to a fluid source.

According to one or more embodiments, the fluid source is selected from a high flow generator, a continuous positive airway pressure (CPAP) machine, a fluid tank, a medicated fluid source, or a humidifier.

According to one or more embodiments, a fluid of the fluid source is selected from a gas, a mixture of gases, or a gas with a medication.

According to one or more embodiments, both sides of the gasket comprise one or more of: a peel-back glue membrane, and a glue material.

According to one or more embodiments, the central opening comprises a snap-on lid.

According to one or more embodiments, the snap-on lid had a circular profile.

Provided herein is a respiratory assembly for use in conjunction with a continuous positive airway pressure (CPAP) equipment. According to one or more embodiments, the respiratory assembly comprises a respiratory mask defining an opening. The assembly further comprises a conduit coupler forming a substantially airtight seal around the opening of the respiratory mask. The conduit coupler comprises a male member and a female member, each defining an aperture for a conduit to fit therethrough. A sleeve of the male member passes through the opening of the respiratory mask to selectively engage with the female member. A gasket is provided between the female member and the respiratory mask such that the gasket forms a substantially airtight seal between the sleeve of the male member and the opening when the male member selectively engages with the female member. A connector end of the female member is in fluid communication with a channel opening of a fluid source. A connector end of the male member is in fluid communication with a CPAP mask assembly, wherein the CPAP mask assembly couples to one or more of a patient's nare and mouth.

Provided herein is a nasal respiratory assembly. The nasal respiratory assembly includes a pair of sheets, each sheet defining an opening sized and shaped to fit over a nostril of a patient, with a ferromagnetic ring positioned at an underside of the sheet and circumferentially aligned with the opening, with an upper side of the sheet configured for sealable engagement with the nostril. The nasal respiratory assembly also includes a pair of posts, each post including a magnetic ring positioned at a first end of the post, and a ball shaped receptacle positioned at a second end of the post, with a passageway extending from the first end to the second end, the magnetic ring comprising an array of magnets, the magnetic ring removably attachable to the ferromagnetic ring. The nasal respiratory assembly also includes a connector with a pair of socket openings at a post end, each socket opening sized and shaped to receive the ball shaped receptacle in a ball and socket arrangement to form a substantially airtight connection therewith, and an inlet at a vent end that is fluid communication with a flexible tubing connected to a fluid source.

According to one or more embodiments, the array of magnets comprises magnets concentrically arranged at or near or about the first end of the post.

According to one or more embodiments, the array of magnets comprises a plurality of magnetic pellets embedded at or near or about the first end of the post.

According to one or more embodiments, the post is 3D printed.

Provided herein is a nasal respiratory assembly. The nasal respiratory assembly includes a pair of sheets, each sheet defining an opening sized and shaped to fit over a nostril of a patient, with a ferromagnetic ring positioned at an underside of the sheet and circumferentially aligned with the opening, with an upper side of the sheet configured for sealable engagement with the nostril. The nasal respiratory assembly further includes a connector. The connector includes a pair of slip rings at a sheet end, each slip ring accommodating a magnetic ring. Each slip ring defining a channel opening. The magnetic ring comprises an array of magnets. The magnetic ring is configured to pivotably tilt about the slip ring. The magnetic ring sized and shaped to be removably attachable to one of the ferromagnetic rings to form a substantially airtight connection therewith. An inlet is provided at a vent end that is fluid communication with a flexible tubing connected to a fluid source. The channel opening has a round, oblong, oval or tear drop shape.

According to one or more embodiments, an opening of the ferromagnetic ring has a round, oblong, oval or tear drop shape, wherein the shape of the opening of the ferromagnetic ring matches the shape of the channel opening of the magnetic ring.

According to one or more embodiments, the array of magnets comprises magnets concentrically arranged at or near or about the sheet end of the slip ring.

According to one or more embodiments, the slip ring is 3D printed.

BRIEF DESCRIPTION OF THE DRAWINGS

The foregoing, as well as the following Detailed Description of preferred embodiments, is better understood when read in conjunction with the appended drawings. For the purposes of illustration, there are shown in the drawings exemplary embodiments; however, the presently disclosed subject matter is not limited to the specific methods and instrumentalities disclosed.

The embodiments illustrated, described, and discussed herein are illustrative of the present invention. As these embodiments of the present invention are described with reference to illustrations, various modifications, or adaptations of the methods and or specific structures described may become apparent to those skilled in the art. It will be appreciated that modifications and variations are covered by the above teachings and within the scope of the appended claims without departing from the spirit and intended scope thereof. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

FIGS. 28A-28D illustrate various aspects of polymagnets forming part of a CPAP nasal respiratory assembly configured for engaging the nostrils of a patient, in accordance with some embodiments of the presently disclosed subject matter.

DETAILED DESCRIPTION OF THE EMBODIMENTS

Figure 1A:
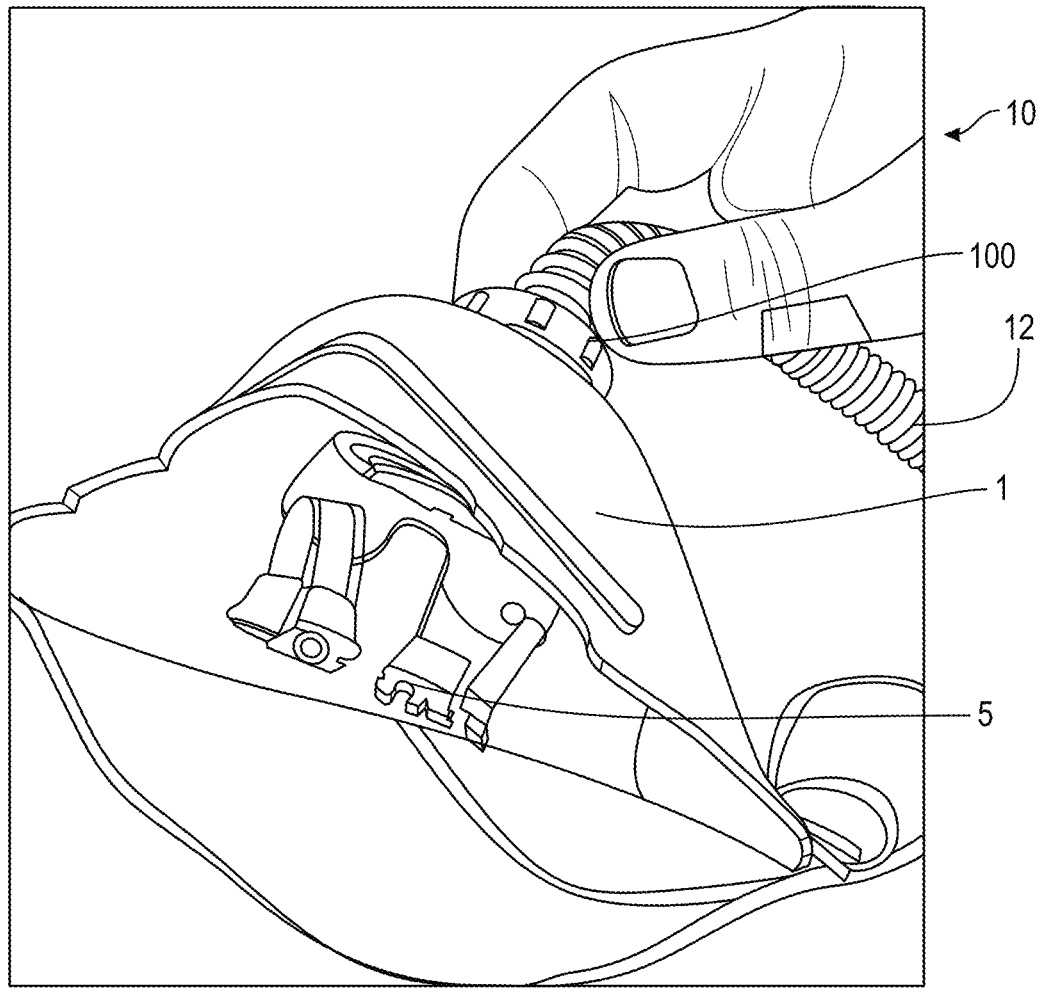
FIG. 1A illustrates a perspective view of a respiratory mask assembly in an assembled configuration.

Below, the technical solutions in the examples of the present invention are depicted clearly and comprehensively with reference to the figures according to the examples of the present invention. Obviously, the examples depicted here are merely some examples, but not all examples of the present invention. In general, the components in the examples of the present invention depicted and shown in the figures herein can be arranged and designed according to different configurations. Thus, detailed description of the examples of the present invention provided in the figures below are not intended to limit the scope of the present invention as claimed, but merely represent selected examples of the present invention. On the basis of the examples of the present invention, all of other examples that could be obtained by a person skilled in the art without using inventive efforts will fall within the scope of protection of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description of The Embodiments section explicitly defines such terms. Accordingly, the actual scope of the disclosure encompasses not only the disclosed embodiments, but also all equivalent ways of practicing or implementing the disclosure under the claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Figure 1B:
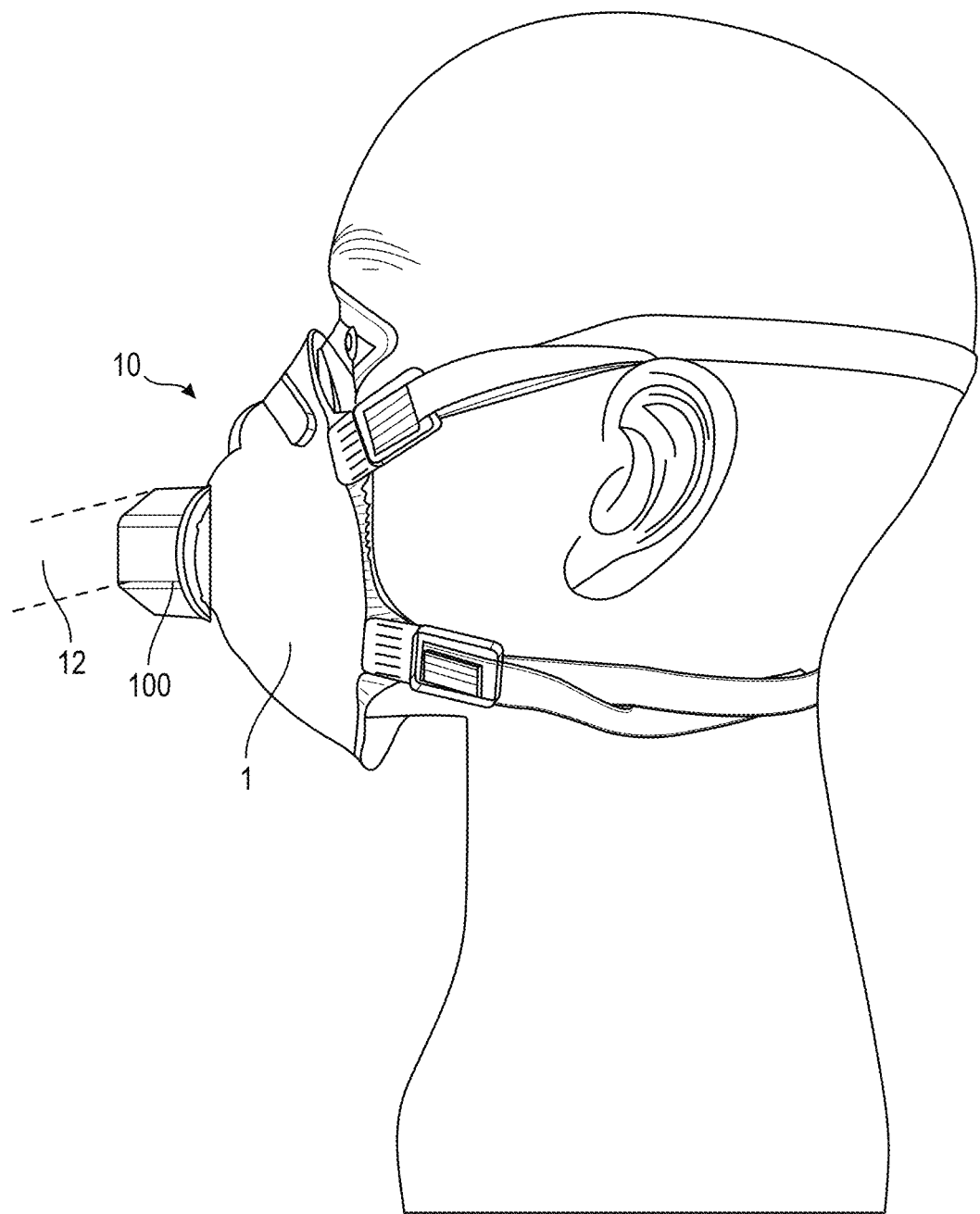
FIG. 1B illustrates the respiratory mask assembly affixed to a human face, in accordance with some embodiments of the presently disclosed subject matter.
Figure 2:
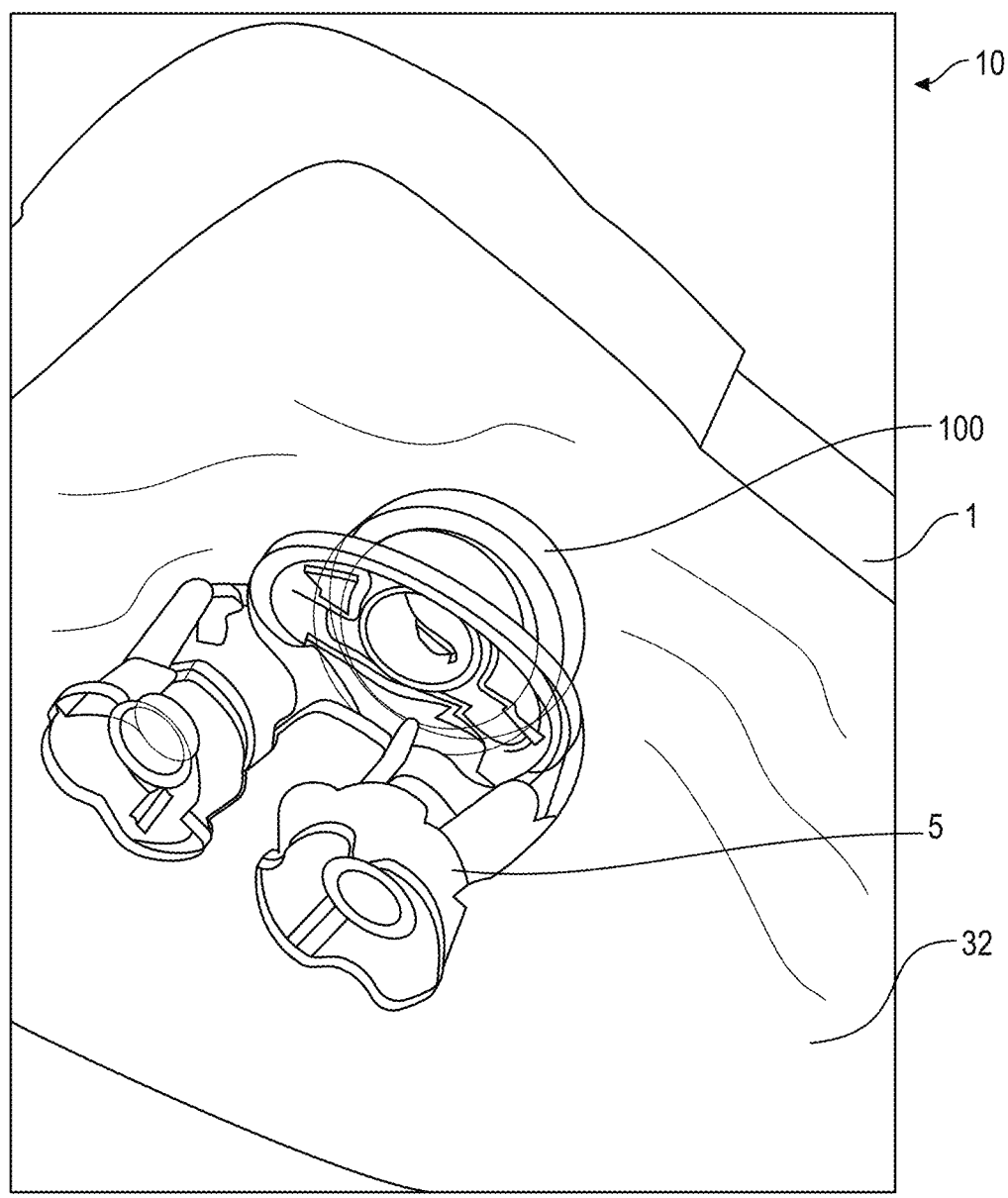
FIG. 2 illustrates a perspective view of an inner side of a respiratory mask assembly in an assembled configuration, in accordance with some embodiments of the presently disclosed subject matter.

Various embodiments of the presently disclosed subject matter are directed to a respiratory mask assembly 10. Some embodiments of the presently disclosed subject matter are directed to a conduit coupler 100 (alternately referred to as "coupler 100" or simply "coupler") for use with respiratory mask assembly 10. In various embodiments, respiratory mask assembly 10 comprises a conduit coupler 100 and a respiratory mask 1; in some embodiments, respiratory mask assembly 10 further comprises a nasal respiratory assembly 5, and a tubing 12 (e.g., a flexible conduit) to supply fluid to nasal respiratory assembly 5. FIG. 1A illustrates respiratory mask assembly 10 in an assembled configuration wherein conduit coupler 100 is assembled thereon, and FIG. 1B illustrates respiratory mask assembly 10 in an affixed configuration wherein the respiratory assembly is affixed to a person with conduit coupler 100 assembled thereon. According to at least one embodiment, respiratory mask assembly 10 may be used in conjunction with a variety of continuous positive airway pressure (CPAP) equipment commonly available in the market including, for example, with embodiments illustrated in FIGS. 14, 17, 18, 20 and 21.

In various embodiments, respiratory mask assembly 10 includes a conduit coupler 100 comprising a male member 24 and a female member 22. Respiratory mask assembly 10 further includes a respiratory mask 1 that defines a central opening therethrough, the central opening sized to receive the male member therethrough. In one implementation, respiratory mask 1 may be disposable. In various embodiments, respiratory mask 1 can be made of any suitable material including cloth, woven and non-woven fabric, paper, gauze, and polymers such as polypropylene, polyurethane, polyacrylonitrile, polystyrene, polycarbonate, polyethylene, and polyester. Respiratory mask assembly 10 also includes a gasket is positioned between the male member and the respiratory mask, the gasket 25 including a central opening 36 to provide a sealing thereto. A channel opening of one of male member 24 and female member 22 connects to a continuous positive airway pressure (CPAP) mask such as nasal respiratory assembly 5 that couples to one or more of a patient's nare and mouth.

In various implementations, nasal respiratory assembly 5 may be substituted or swapped out with any other similar CPAP mask (configured for supplying fluid/gas to a patient's mouth or nares or both) that a respiratory mask such as respiratory mask 1 can be used in conjunction with (as illustrated in FIG. 1) to thereby create a physical barrier between the mouth and nose of the wearer on the one side and potential contaminants in the immediate environment on the other side, or alternately prevent potential contaminants let out from the mouth and nose of the wearer on the one side from being spread into the immediate environment one the other side.

Conduit coupler 100 can include a gasket 25, a female member 22, and a male member 24. In at least one implementation, gasket 25 can be in the form of a membrane with an orifice formed therethrough. One or both sides of gasket 25 can include an adhesive for forming a sealing engagement with one or more of the male member 24, the female member 22, an interior surface 32 of the respiratory mask and an exterior surface 34 of the respiratory mask. In various embodiments, gasket 25 can take any suitable shape. In some embodiments, gasket 25 can effectively operate as a washer that helps maintain a substantially sealing engagement with one or more of the male member 24, the female member 22, an interior surface 32 of respiratory mask 1 and an exterior surface 34 of respiratory mask 1. In various implementations, conduit coupler 100 operates to form a substantially airtight seal around a central opening 36 formed on respiratory mask 1. Both male member 24 and a female member 22 define apertures therethrough for fluid flow or for insertion therein of a tubing or conduit such as tubing 12. In one embodiment, female member 22 selectively engages with male member 24 to form a substantially airtight connection therebetween. Coupler 100 further includes one or two gaskets 25 provided between the male and female members. A side of the at least one gasket is configured for scalable engagement with a wall of a respiratory mask when the male member is inserted through central opening 36 formed on respiratory mask 1 and selectively engaged with female member 22. A connector end of the female member 22 cooperates with a channel opening of a fluid source (e.g., a tubing or conduit). In some implementations, a connector end of the female member may form a substantially airtight connection with tubing 12. A connector end of the male member 24 is in fluid communication with one or more of a patient's nare and mouth.

In some embodiments, gasket 25 may engage with or may otherwise include one or more flexible adhesive sheets (not shown) to provide scalable engagement with one or more of the male member, the female member, an interior surface 32 of the respiratory mask, and an exterior surface 34 of the respiratory mask. Gasket 25 can be constructed from any known material, including (but not limited to) woven fabric, plastic, and/or latex. For example, in some embodiments, gasket 25 can be constructed from PVC, polyethylene, polyurethane, latex, or combinations thereof. In some embodiments, gasket 25 can be a foam medical tape, a surgical tape, and/or a hypoallergenic tape. One or both surfaces of gasket 25 can include an adhesive. In one embodiment, the adhesive can be any medically-safe adhesive known or used in the art. For example, the adhesive can be selected from one or more acrylates (such as methacrylate, alkyl acrylate, or epoxy diacrylate), acrylic acids, polyvinyl chloride, alkyl esters, or combinations thereof. In some embodiments, the adhesive may be a pressure-sensitive adhesive such that the gasket can be adhered and removed as desired. The adhesive may be selected to show mild or no irritation to a patient's skin. In some embodiments, the adhesive tape may be configured as a hydrocolloid tape and/or may include a polyurethane reactive layer. In some embodiments, gasket 25 may include a peel-back glue membrane.

Figure 14:
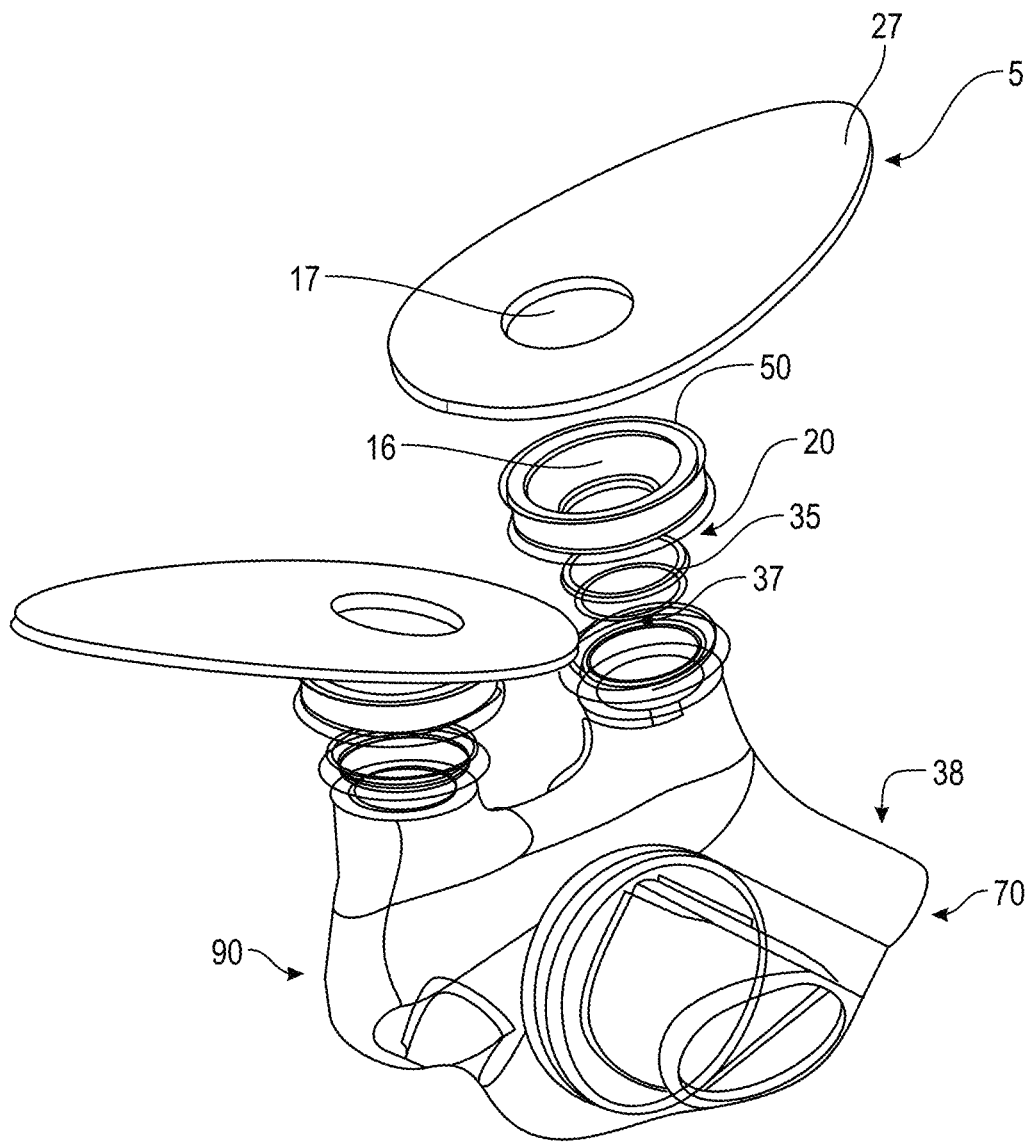
FIG. 14 illustrates a CPAP nasal respiratory assembly configured for engaging the nostrils of a patient, in accordance with some embodiments of the presently disclosed subject matter.

In one embodiment, tubing 12 passes through male member 24, central opening 36, one or more gaskets 25, and female member 22 to supply fluid to inlet 38 of a nasal respiratory assembly such as nasal respiratory assembly 5 shown in FIG. 14; tubing 12 may further form a substantially airtight connection with inlet 38, with the other end of tubing 12 in fluid communication to fluid source forming part of a CPAP machine, for example. Coupler 100 operates to form a substantially airtight seal around central opening 36 when male member 24 is coupled with female member 22 such that any particles of 0.3-micron size or greater such as for example, a microbe such as a virus, bacteria, fungus, and similar other microorganism, are prevented or limited in their movement across, or around the edges of, central opening 36 in either direction. In one embodiment, any particles of 0.1-micron size or greater are prevented or limited in their movement across, or around the edges of, central opening 36 in either direction. In one embodiment, any particles of 0.01-micron size or greater are prevented or limited in their movement across through central opening 36. In one embodiment, any particles of 1.0-micron size or greater are prevented or limited in their movement across, or around the edges of, central opening 36 in either direction. In one embodiment, any particles of 10.0-micron size or greater are prevented or limited in their movement across, or around the edges of, central opening 36 in either direction.

Embodiments of the presently disclosed subject matter can advantageously permit a person to simultaneously wear both a continuous positive airway pressure (CPAP) mask and a respiratory mask (such as, e.g., a N95 respirator) at the same time. Embodiments of the presently disclosed subject matter can operate to reduce or eliminate the spread of the communicable disease from a person wearing respiratory mask assembly 10 to medical professionals and caretakers who may spend time in the vicinity of the patient. Embodiments of the presently disclosed subject matter can further operate to reduce or eliminate the spread of the communicable disease to a person wearing respiratory mask assembly 10 from airborne microbes present in the vicinity of the person wearing respiratory mask assembly 10. Embodiments of the presently disclosed subject matter can accordingly permit a person/patient to wear both a continuous positive airway pressure (CPAP) assembly and respiratory mask simultaneously whereby movement of airborne particles of 0.01-micron size or 0.1-micron size or 0.3-micron size or 1.0-micron size or 10.0-micron size across central opening 36 in either direction (inward or outward) is prevented or limited.

In at least one embodiment, coupler 100 includes two gaskets 25 wherein a first gasket 25 contacts an exterior surface 34 of respiratory mask 1 to form a substantial airtight seal therewith and a second gasket contacts an interior surface 32 of the respiratory mask to form a substantial airtight seal therewith. In the same embodiment, the other side of first gasket 25 contacts female member 22 to form a substantial airtight seal therewith whereas the other side of second gasket 25 contacts male member 24 to form a substantial airtight seal therewith. In this embodiment, coupler 100 operates to form a substantially airtight seal around central opening 36 formed on a respiratory mask 1 by the use of two gaskets 25. Both sides of each gasket 25 includes an adhesive material or an adhesive tape.

In at least one embodiment, the respiratory mask is configured for blocking at least 95 percent of particles of 0.3-micron size or greater (i.e., a N95 respiratory mask or N95 respirator). In one embodiment, the respiratory mask is a surgical mask. In one embodiment, gasket 25 is in the form of a membrane with an orifice formed therethrough for insertion over a portion of male member 24 to form a substantially airtight seal therewith.

N95 respirators and surgical masks (face masks) are examples of personal protective equipment that are used to protect the wearer from airborne particles and from liquid contaminating the face. Center for Disease Control and Prevention (CDC), National Institute for Occupational Safety and Health (NIOSH) and Occupational Safety and Health Administration (OSHA) regulate N95 respirators. An N95 respirator is a respiratory protective device designed to achieve a very close facial fit and very efficient filtration of airborne particles. The edges of the respirator are designed to form a seal around the nose and mouth. Surgical N95 Respirators are commonly used in healthcare settings and are a subset of N95 Filtering Facepiece Respirators (FFRs), often referred to as N95s.

A surgical mask is a loose-fitting, disposable device that creates a physical barrier between the mouth and nose of the wearer and potential contaminants in the immediate environment. Surgical masks are regulated under 21 CFR 878.4040. Surgical masks are not to be shared and may be labeled as surgical, isolation, dental, or medical procedure masks. They may come with or without a face shield. These are often referred to as face masks, although not all face masks are regulated as surgical masks. Surgical masks are made in different thicknesses and with different ability to protect a wearer from contact with liquids and fluids. These properties may also affect how easily the wearer can breathe through the face mask and how well the surgical mask protects the wearer. If worn properly, a surgical mask is meant to help block large-particle droplets, splashes, sprays, or splatter that may contain germs (viruses and bacteria), keeping it from reaching your mouth and nose. Surgical masks may also help reduce exposure of your saliva and respiratory secretions to others. While a surgical mask may be effective in blocking splashes and large-particle droplets, a face mask, by design, does not filter or block very small particles in the air that may be transmitted by coughs, sneezes, or certain medical procedures. Surgical masks also do not provide complete protection from germs and other contaminants because of the loose fit between the surface of the face mask and your face. Surgical masks are not intended to be used more than once. If the mask is damaged or soiled, or if breathing through the mask becomes difficult, one should remove the face mask, discard it safely, and replace it with a new one. To safely discard the mask, it should be placed in a plastic bag and put it in the trash. Hands should be washed after handling the used mask. If worn properly, a surgical mask is meant to help block large-particle droplets, splashes, sprays, or splatter that may contain germs (viruses and bacteria), keeping it from reaching your mouth and nose. Surgical masks may also help reduce exposure of the wearer's saliva and respiratory secretions to others.

People with chronic respiratory, cardiac, or other medical conditions that make breathing difficult need to be careful when using an N95 respirator because the N95 respirator can make it more difficult for the wearer to breathe. Embodiments of the presently disclosed subject matter can help overcome this shortcoming whereby the N95 respirator can be work in conjunction with a CPAP or similar other positive air pressure device. In detail, respiratory mask 1 in the form of a N95 respirator can be fitted over (as illustrated in FIG. 1) a respiratory assembly such nasal respiratory assembly 5 to still a physical barrier between the mouth and nose of the wearer and potential contaminants in the immediate environment (or prevent potential contaminants let out from the mouth and nose of the wearer from being spread into the immediate environment).

In various embodiment, the gasket is formed of an adhesive foam material. In at least one embodiment, the gasket is formed of a stretchable elastomeric material. This elastomeric material can further include a glue material for forming a scalable engagement with surfaces of male member, female member, and the interior surface and/or exterior surface of the respiratory mask such as a N95 respirator. In one embodiment, one or more sides of the gasket comprises a peel-back glue membrane. In one embodiment, one or more sides of the at least one gasket comprises a glue material. In one embodiment, the gasket forms an interference fit with the male member. In one embodiment, both sides of the gasket comprise a peel-back glue membrane. In one embodiment, both sides of the gasket comprise a glue material.

In one embodiment, the female member detachably couples with the male member. In one embodiment, the female member screws over threads formed on the male member. In one embodiment, the female member includes one or more releases that can be pivoted to form a selective engagement with the male member. In one embodiment, the female member selectively engages the male member with a quick disconnect mechanism.

In one embodiment, the channel opening of the fluid source comprises a flexible tubing connected to the fluid source. In one embodiment, the fluid source comprises a continuous positive airway pressure (CPAP) source. In one embodiment, the fluid source is selected from a high flow generator, a continuous positive airway pressure (CPAP) machine, a fluid tank, a medicated fluid source, or a humidifier. In one embodiment, the fluid is selected from a gas, a mixture of gases, or a gas with a medication.

Nasal respiratory assembly 5 (see FIG. 14) is capable of being installed upon a patient according to one or more embodiments of the presently disclosed subject matter. In one embodiment, nasal respiratory assembly 5 is as described in U.S. provisional application No. 62/855,193 filed on May 31, 2019, the entire contents of which are incorporated by reference herein. In one embodiment, nasal respiratory assembly 5 may be replaced by a respiratory assembly such as respiratory mask assembly 10 as described in international patent application number PCT US/2018/019109 filed on Aug. 31, 2018, the entire contents of which are incorporated by reference herein.

In some embodiments, the fluid source can be a high flow generator, a continuous positive airway pressure (CPAP) machine, a fluid tank, a humidifier, or any other fluid source known or used in the art. The term "fluid" as used herein refers to any gas, mixture of gases, or gas with medication (such as an aerosol medication) suitable for delivery to the airway of a human. A flexible tubing such as tubing 12 as shown in FIG. 1, for example, can couple with inlet to supply the fluid from the fluid source, the tubing can include any known flexible tubing. The term "tubing" as used herein refers to any conduit, a delivery conduit, a tube, pipe, passage, or channel through which fluid flows. The term "flexible" as used herein refers to any tubing that is able to flex or bend and that is compliant and will readily conform to the general shape and contours of the human body. In some embodiments, tubing 12 can be constructed from medical grade materials, such as (but not limited to) polyurethane, polyvinyl chloride, polyamide, polyester, polyolefin, silicone, fluoropolymer, and combinations or copolymers thereof. The tubing is flexible, resilient, and hollow. In some embodiments, the tubing can have an inner diameter of between about 2-4 mm, although tubing with larger or smaller diameters can be used. For example, the inner diameter of the tubing can be increased or decreased to adjust for a particular wearer's preferences and/or needs. In some embodiments, during use, tubing can be hooked over the cars of a patient and can be brought up under the chin during use.

According to one or more embodiments, a method of forming a substantially airtight seal around an opening formed on a respiratory mask is provided. In at least one embodiment, the method comprises providing respiratory assembly conduit coupler. The coupler comprises a male member and a female member defining apertures therethrough for fluid flow, the female member selectively engageable with the male member to form a substantially airtight connection therebetween, and at least one gasket provided between the male and female members. A side of the at least one gasket is configured for scalable engagement with a wall of a respiratory mask when the male member is inserted through an opening formed on the respiratory mask and selectively engaged with the female member. A connector end of the female member cooperates with a channel opening of a continuous positive airway pressure (CPAP) machine to form a substantially airtight connection therewith. A connector end of the male member is in fluid communication with one or more of a patient's nare and mouth. The method further comprises forming an opening in the respiratory mask, inserting the male member through the opening formed in the respiratory mask, and selectively engaging the male member by the female member such that the at least one gasket forms a substantially airtight scalable engagement with the wall of the respiratory mask.

According to various embodiments, a respiratory assembly conduit coupler for forming a substantially airtight seal around an opening formed on a respiratory mask is provided. In various embodiments, the coupler comprises a male member and a female member defining apertures therethrough for fluid flow, the female member selectively engageable with the male member to form a substantially airtight connection therebetween, and at least one gasket provided between the male and female members. A side of the at least one gasket configured for scalable engagement with a wall of a respiratory mask when the male member is inserted through an opening formed on a respiratory mask and selectively engaged with the female member. A connector end of the male member cooperates with a channel opening of a fluid source to form a substantially airtight connection therewith. A connector end of the female member is in fluid communication with one or more of a patient's nare and mouth. Accordingly, the position of the male member can be exchanged with the position of the female member.

The respiratory assembly disclosed herein has a wide variety of applications. For example, in some embodiments, the assembly can be used for high flow delivery of respirator gas via nasal assembly. In some embodiments, the air can be heated to near body temperature (e.g., about 37° C.) and/or humidified (e.g., about 100% relative humidity) to decrease airway moisture loss, airway cooling, nasal irritation, and the like. In high flow therapy, the source of oxygen is typically blended with compressed air, allowing the delivery of air, blends of air and oxygen from about 22% to about 99%, or delivery of 100% oxygen with the use of an oxygen blender. Advantageously, the disclosed assembly includes tubing large enough to deliver flow rate of respiratory gas of up to about 50 liters per minute for adults. The nasal assembly and its components are also small enough to prevent sealing of the nares, allowing flow during exhalation and allowing the escape of excess gas during inhalation. Beneficially, because the delivered flow rate can meet the inspiration flow rate, the delivered gases are not diluted by room air.

Alternatively, or in addition, the disclosed respiratory assembly can be used with a continuous positive airway pressure (CPAP) machine. CPAP machines typically apply mild air pressure on a continuous basis to keep a patient's airway continuously open. As a result, CPAP machines used in conjunction with a patient's stent can advantageously cause the lungs' alveoli to open and thus recruit more of the lung's surface area for ventilation. CPAP machines are generally used for people with breathing problems, such as sleep apnea. Alternatively, CPAP machines can be used to treat pre-term infants whose lungs have not yet fully developed. In some embodiments, the disclosed assembly can be used as a replacement for traditional CPAP masks.

The disclosed respiratory assembly can further be used in pressure recording applications in clinical settings, such as to diagnose sleep apnea or other disorders. Particularly, sleep apnea can be diagnosed based on characteristic clinical features associated with episodes of cessation of breathing that define hypopnoeic and apnoeic events. The disclosed device can be used to measure nasal pressure by measuring nasal pressure with nasal prongs connected to a pressure transducer.

The disclosed assembly can further be used with a fluid tank, a humidifier, or any other fluid source known or used in the art. Advantageously, the disclosed assembly may eliminate over-the-car soreness and lip soreness commonly found in traditional respiratory masks and cannula. In addition, the disclosed assembly may enable better control of gases (e.g., oxygen) during fluid delivery applications. In some embodiments, the disclosed assembly is strapless and maskless, thereby increasing using comfort. As a result, patients are more likely to follow doctor's orders and use the assembly. In addition, unsightly mask and strap skin indentations are eliminated. The disclosed assembly is less likely to be dislodged inadvertently by the patient, such as during movement or when being pressed against a pillow.

In some embodiments, the disclosed respiratory assembly includes a sanitizing enclosure that can be used to sanitize the reusable portions of the CPAP assembly. The term "sanitizing" as used herein refers to the elimination of all or nearly all microbial forms. The sanitizing enclosure can include an activated oxygen and/or UV light generator that is used to clean and/or sanitize the reusable CPAP elements. For example, in some embodiments, the generator can generate activated oxygen to sanitize the contents of interior of the enclosure and the reusable CPAP system Activated oxygen (also known as $O_3$ or ozone) is a safe, naturally-occurring gas that has been shown to kill virtually all known forms of viruses in water and air. Particularly, activated oxygen has been shown to interfere with the metabolism of bacterium cells, likely through inhibiting and blocking the operation of the enzymatic control system. A sufficient amount of activated oxygen breaks through the cell membrane, leading to destruction of the bacteria. Activated oxygen destroys viruses by diffusing through the protein coat into the nucleic acid core, resulting in damage to the viral RNA. At higher concentrations, activated oxygen destroys the viral capsid by oxidation to affect the DNA or RNA structure. Activated oxygen has been shown to be effective in destroying dozens of harmful pathogens, including *E. coli*, influenza virus, Staphlococus, *Streptococcus* bacteria, Stomatitis virus, and many more.

In some embodiments, the generator can produce activated oxygen in a concentration of about 10-500 ppm (parts per million) within the interior and/or within the disclosed system. In some embodiments, the generator can produce UV light to sanitize the contents of the interior of the enclosure and the associated CPAP equipment. To this end, the generator can include one or more ultraviolet lights that can be activated for a pre-set time period. UV light is highly effective at deactivating microorganisms, including bacteria, viruses, yeasts, and molds. In some embodiments, the UV light is in the range of about 100-280 nanometers which is known to damage the DNA molecules in bacteria, viruses, molds, yeasts, and other microorganisms, preventing them from replicating and causing harm.

The sanitizing enclosure can kill about 99% of mold, bacteria, and viruses in the CPAP user's sockets (or mask), tubing, humidifier, and CPAP chamber. In addition to being highly effective, the sanitizing enclosure is designed for ease of use. Users simply place their sockets or mask in the sanitizing enclosure, close the lid, and walk away. Importantly, no disassembly of the CPAP apparatus is required prior to start of the sanitizing process. Advantageously, the sanitizing enclosure can be used daily. In one embodiment, the sanitizing enclosure is configured to support several sanitization cycles to be carried out per day. The enclosure can be configured in any desired shape, such as circular, oval, square, triangular, oval, hexagonal, pentagonal, star, abstract, and the like. The enclosure can be configured in any desired size. In some embodiments, the enclosure can have a relatively small size, compared to the size of the CPAP assembly. For example, the enclosure can have a height, width, and depth of less than about 5 inches, such as no more than about 5.0, 4.75, 4.5, 4.25, 4.0, 3.75, 3.5, 3.25, 3.0, 2.75, 2.5, 2.25, 2.0, 1.75, 1.5, 1.25, or 1.0 inches. However, the enclosure can have any desired size to accommodate a particular CPAP element within its interior.

Figure 13:
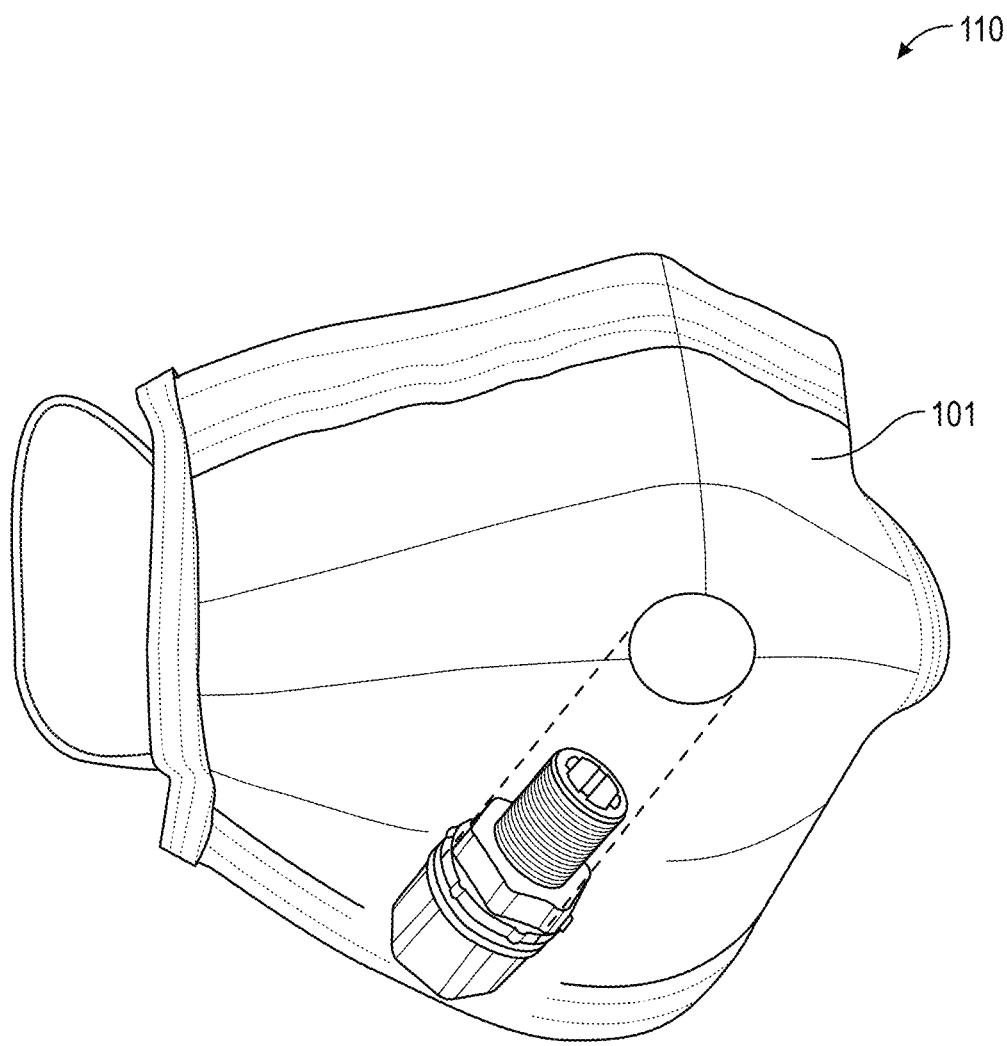
FIG. 13 illustrates a respiratory mask assembly wherein the respiratory mask forming part of the respiratory mask assembly is a typical surgical mask, in accordance with some embodiments of the presently disclosed subject matter.

FIG. 13 illustrates a respiratory assembly 110 wherein respiratory mask 101 is a surgical mask, as is well understood in the art. Respiratory assembly 110 may otherwise share same or similar features as respiratory mask assembly 10.

FIG. 14 illustrates nasal respiratory assembly 5 that can be installed upon a patient along with respiratory mask assembly 10, according to one or more embodiments of the presently disclosed subject matter. As shown, nasal respiratory assembly 5 includes sheets 27 that are configured to engage the nares (i.e., nostrils) of the patient. The nasal respiratory assembly also includes socket magnet posts 20. One end of each socket magnet post 20 is configured to removably attach to a ferromagnetic dome ring on sheet 27 through the presence of a magnetic field; the other end of each socket magnet post 20 is configured to engage an opening of nasal connector 90. Nasal respiratory assembly 5 accordingly includes a pair of sheets 27, each sheet defining an opening 17 sized and shaped to fit over the nostril of a patient, with a ferromagnetic dome-shaped ring positioned at an underside of the sheet and circumferentially aligned with the opening, with an upper side of the sheet configured for scalable engagement with the nostril. Nasal respiratory assembly 5 includes a pair of socket magnet posts 20, each socket magnet post 20 including a magnetic ring 50 (e.g., in the form of a magnetic ring as shown in FIG. 1) positioned at a first end and a post receptacle 35 positioned at a second end with a passageway extending from the first to the second ends. The magnetic ring 50 removably attaches to the dome-shaped ring at exit end 16. In one embodiment, magnetic ring 50 is configured to pivotably move or rotate about the surface of dome-shaped ring in a ball and socket arrangement while continuing to maintain a substantially airtight connection at the interface between magnetic ring 50 and the dome-shaped ring. Nasal connector 90 of nasal respiratory assembly 5 includes a pair of channel openings, each channel opening sized and shaped to cooperate with one of the post receptacles 35 to form a substantially airtight connection therewith such that channel 37 of socket magnet post 20 is aligned with the channel opening of nasal connector 90, and an inlet such as a vent coupling at a vent end that is configured for fluid communication with a tubing 12 connected to a fluid source. In one embodiment, a vent such as vent 70 is located between the vent coupling and the tubing 12. Vent 70 includes a vent receptacle sized and shaped to cooperate with the coupling to form a substantially airtight connection therewith, and inlet 38 sized and shaped to cooperate with a tubing such as tubing 12 shown in FIG. 1 to form a substantially airtight connection therewith.

In some embodiments, each magnetic ring 50 can be in the form of a plurality of magnets 250 arranged as an array on a periphery of a sheet-facing side of magnet socket 52 is positioned about a first end of socket magnet post 20. In an alternate embodiment, each magnetic ring 50 can be in the form of a single ring magnet provided on a periphery of a sheet-facing side of magnet socket 52 is positioned about a first end of socket magnet post 20.

Figure 15:
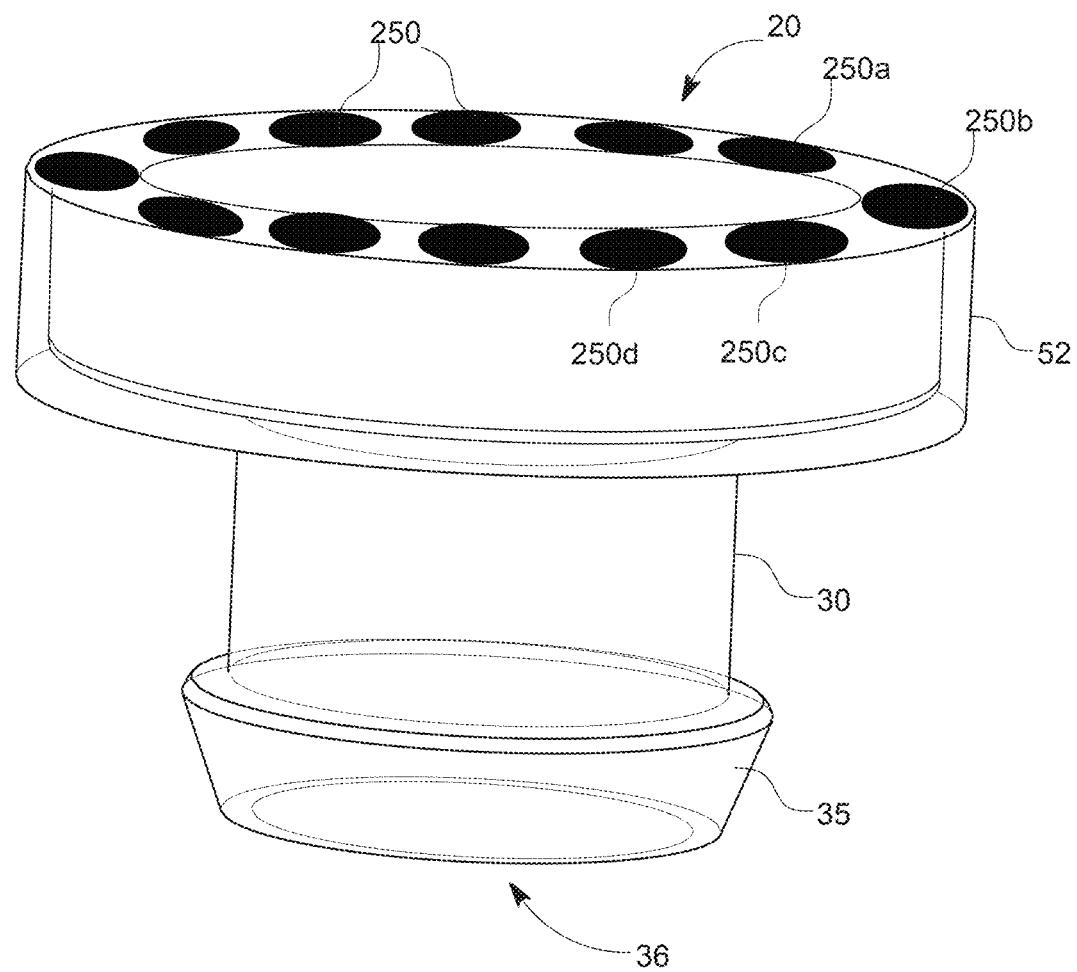
FIG. 15 is a side perspective view of a socket magnet post that can be used with the disclosed nasal respiratory assembly in some embodiments.

Accordingly, in at least one embodiment, each socket magnet post 20 may include a magnetic ring 50 comprising a plurality of magnets 250 forming an array as shown in FIG. 15, instead of a magnetic ring 50 comprising a single ring magnet as illustrated in FIG. 14. In one embodiment, the plurality of magnets 250 may take the form of magnet pellets that are embedded within magnetic ring 50 of socket magnet post 20, for example, using 3D printing technics commonly known in the art. Magnetic ring 50 can accordingly include a plurality of magnets 250 arranged as an array on a periphery of a sheet-facing side of magnetic ring 50. In various embodiments, the polarity of the magnets 250 may be arranged such that each magnet 250 has the opposite polarity as an adjacent magnet 250. In other words, the polarity may be alternated among the plurality of magnets 250 arranged as an array on magnetic ring 50. Accordingly, the plurality of magnets 250 of alternating polarities may attach to ring 262 (ring 262 may be a ferromagnetic ring or a magnetic ring in various embodiments) by magnetic attraction forces. In one embodiment, socket magnet post 20 can be formed by 3D printing technics. In various embodiments, the array of magnets 250 may be substantially planar. In various embodiments, a plane of the array of magnets 250 may be substantially planar to a transverse plane passing through the center of magnetic ring 50. In various embodiments, the array of magnets 250 may be concentrically arranged.

As is commonly known in the art, 3D printing, or additive manufacturing, is the construction of a three-dimensional object from a CAD model or a digital 3D model. The term "3D printing" can refer to a variety of processes in which material is deposited, joined, or solidified under computer control to create a three-dimensional object, with material being added together (such as plastics, liquids or powder grains being fused together), typically layer by layer. The precision, repeatability, and material range of 3D printing have increased to the point that some 3D printing processes are considered viable as an industrial-production technology, whereby the term additive manufacturing can be used synonymously with 3D printing. One of the key advantages of 3D printing is the ability to produce very complex shapes or geometries that would be otherwise impossible to construct by hand, including hollow parts or parts with internal truss structures to reduce weight. Fused deposition modeling, or FDM, is the most common 3D printing process in use as of 2020.

According to one embodiment, a nasal respiratory assembly 5 comprises a pair of sheets, each sheet defining an opening sized and shaped to fit over a nostril of a patient, with a ferromagnetic ring positioned at an underside of the sheet and circumferentially aligned with the opening, with an upper side of the sheet configured for scalable engagement with the nostril. The nasal respiratory assembly 5 comprises a pair of socket magnet posts 20. Each socket magnet post 20 includes a magnetic ring 50 positioned at a first end of the post, and a ball shaped receptacle positioned at a second end of the post, with a passageway extending from the first end to the second end, the magnetic ring 50 comprising an array of magnets 250. The magnetic ring 50 removably attachable to the ferromagnetic ring. Nasal respiratory assembly further comprises a connector with a pair of socket openings at a post end, each socket opening sized and shaped to receive the ball shaped receptacle in a ball and socket arrangement to form a substantially airtight connection therewith, and an inlet at a vent end that is fluid communication with a flexible tubing connected to a fluid source. The array of magnets can comprise magnets concentrically arranged at the first end of the post. The array of magnets can comprise a plurality of magnetic pellets embedded at the first end of the post. Post 20 can be 3D printed.

Nasal respiratory assembly 5 includes at least one vent 70 for receiving treatment gases to the nasal cavity of a patient. One end of vent 70 has an inlet 38 configured for connecting to a fluid source (not shown) via a fluid tubing such tubing 12 that provides the respiratory gas, while a vent receptacle located at the other end of vent 70 engages a vent coupling of nasal connector 90. Accordingly, nasal respiratory assembly 5 can include one or more vents 70 positioned proximal to where fluid flow occurs. It should be appreciated that vent 70 can be positioned at any desired location and are not limited to the locations illustrated herein. In some embodiments, vent 70 can include a socket including an adaptor. The adaptor can be constructed in any desired shape to allow connection with tubing 12 (tubing 12 is shown in FIG. 1). In such embodiments, the outer diameter of the adaptor is greater than the inner diameter of tubing 12. In this way, the adaptor is held within the tubing for a desired amount of time, and cannot be accidentally unlodged by the patient, such as during sleep. However, the adaptor can be releasably connected to tubing 12 using any known mechanism.

In some embodiments, the fluid source can be a high flow generator, a continuous positive airway pressure (CPAP) machine, a fluid tank, a humidifier, or any other fluid source known or used in the art. The term "fluid" as used herein refers to any gas, mixture of gases, or gas with medication (such as an aerosol medication) suitable for delivery to the airway of a human. A flexible tubing such as tubing 12 as shown in FIG. 1, for example, can couple with inlet 38 to supply the fluid from the fluid source, the tubing can include any known flexible tubing. The term "tubing" as used herein refers to any conduit, a delivery conduit, a tube, pipe, passage, or channel through which fluid flows. The term "flexible" as used herein refers to any tubing that is able to flex or bend and that is compliant and will readily conform to the general shape and contours of the human body. In some embodiments, tubing 12 can be constructed from medical grade materials, such as (but not limited to) polyurethane, polyvinyl chloride, polyamide, polyester, polyolefin, silicone, fluoropolymer, and combinations or copolymers thereof. The tubing is flexible, resilient, and hollow. In some embodiments, the tubing can have an inner diameter of between about 2-4 mm, although tubing with larger or smaller diameters can be used. For example, the inner diameter of the tubing can be increased or decreased to adjust for a particular wearer's preferences and/or needs. In some embodiments, during use, tubing can be hooked over the ears of a patient and can be brought up under the chin during use.

Socket magnet posts 20 are configured as nasal prongs that extend towards and contact rings 262 (shown in FIG. 17) of sheets 27 via magnetic ring 50. Sheets 27 are configured for attaching to the nostrils of a wearer such that fluid received at inlet 38 is delivered into the nostrils of the wearer via the respective opening 17 in sheets 27. Ring 262 (which may be dome-shaped in some embodiments) is made an integral component of sheet 27 such that the openings of ring 262 is aligned with the respecting openings 17 of sheets 27.

In some embodiments, as shown in FIG. 15 for example, each socket magnet post 20 is configured to removably attach to a respective ring 262 of sheets 225 via a plurality of magnets 250 arranged as an array on a periphery of a sheet-facing side of magnet socket 52 is positioned about a first end of socket magnet post 20. Accordingly, in one embodiment, each socket magnet post 20 may include a plurality of magnets 250 (as shown in FIG. 15) instead of a single ring as illustrated in FIG. 14. In one embodiment, the plurality of magnets 250 may take the form of magnet pellets that are embedded within magnet socket 52 of socket magnet post 20, for example, using 3D printing technics commonly known in the art. Magnet socket 52 of FIG. 15 embodiment is accordingly configured to house a plurality of magnets 250 arranged as an array on a periphery of a sheet-facing side of magnet socket 52. In various embodiments, the polarity of the magnets 250 may be arranged such that each magnet 250 has the opposite polarity as an adjacent magnet 250. In other words, the polarity may be alternated among the plurality of magnets 250 arranged as an array on magnet socket 52. For example, in the FIG. 15 embodiment, an exposed side of magnet 250a and magnet 250c (i.e., the side shown exposed on FIG. 15) may have a north polarity whereas an exposed side of magnet 250b and magnet 250d may have a south polarity. Accordingly, the plurality of magnets 250 of alternating polarities may attach to ring 262 by magnetic attraction forces. In one embodiment, socket magnet post 20 can be formed by 3D printing technics. In various embodiments, the array of magnets 250 may be substantially planar. In various embodiments, a plane of the array of magnets 250 may be substantially planar to a transverse plane passing through the center of magnet socket 52. In various embodiments, the array of magnets 250 may be concentrically arranged.

In some embodiments, magnet socket 52 (i.e., an upper surface of socket magnet post 20) can be angled in relation to post body 30 to allow for enhanced attachment to ring 262 of sheet 27 for better positioning on the patient's nostrils. Sheets 27 may be configured for attaching to the nostrils of a wearer such that fluid received at inlet 38 is delivered into the nostrils of the wearer via the respective opening 17 in sheets 27. Ring 262 (which may be dome shaped in some embodiments) is made an integral component of sheet 27 such that the openings of ring 262 is aligned with the respecting openings 17 of sheets 27. As shown in FIG. 15, an upper end of each socket magnet post 20 includes a magnet socket 52 housing a plurality of magnets 250 arranged as an array. Socket magnet post 20 further includes post body 30, a post receptacle 35 and a central opening 36. In some embodiments, socket magnet posts 20 are parallel or about parallel to each other. While each magnet 250 may be cylindrical or pellet shaped, other shapes are possible without deviating from the spirit of the presently disclosed subject matter; similarly, ring 262 may take other shapes such that any shape taken by ring 262 compliments or matches the configuration/arrangement of magnets 250. In various embodiments, ring 62 is made of a ferromagnetic material such that it is attracted by the magnetic field of magnets 250 so as to form a substantially airtight bond or attachment therewith. In some embodiments that include an HFO source and/or a HFNC, the upper end of each socket magnet post 20 can include a magnet socket 52 configured to house magnets such as magnets 250.

According to one embodiment, a nasal respiratory assembly 5 comprises a pair of sheets, each sheet defining an opening sized and shaped to fit over a nostril of a patient, with a ferromagnetic ring positioned at an underside of the sheet and circumferentially aligned with the opening, with an upper side of the sheet configured for scalable engagement with the nostril. The nasal respiratory assembly 5 comprises a pair of socket magnet posts 20. Each socket magnet post 20 includes a magnetic ring in the form of magnet socket 52 positioned at a first end of the post, and a ball shaped receptacle positioned at a second end of the post, with a passageway extending from the first end to the second end, the magnet socket 52 comprising an array of magnets 250. The magnet socket 52 is removably attachable to the ferromagnetic ring. Nasal respiratory assembly further comprises a connector with a pair of socket openings at a post end, each socket opening sized and shaped to receive the ball shaped receptacle in a ball and socket arrangement to form a substantially airtight connection therewith, and an inlet at a vent end that is fluid communication with a flexible tubing connected to a fluid source. The array of magnets can comprise magnets concentrically arranged at the first end of the post. The array of magnets can comprise a plurality of magnetic pellets embedded at the first end of the post. Post 20 can be 3D printed.

Figure 16:
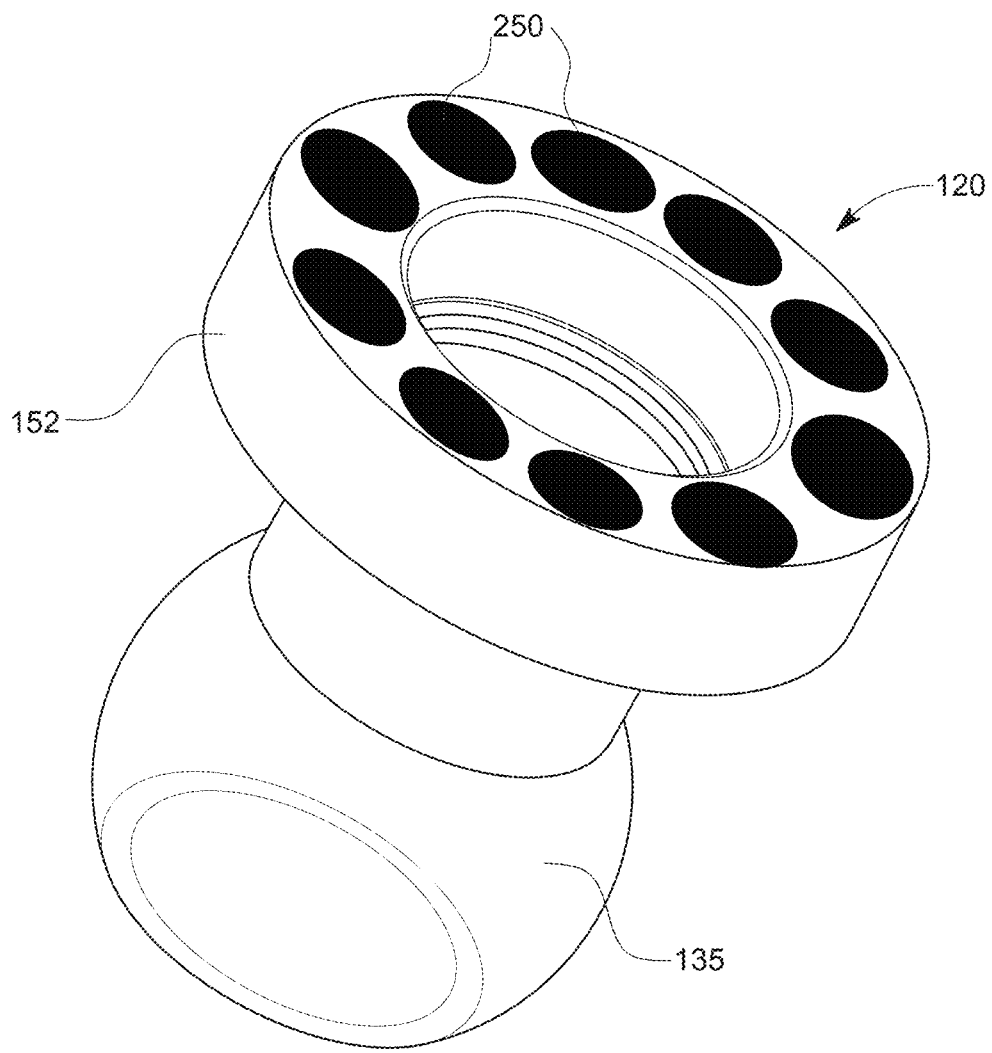
FIG. 16 is a side perspective view of a port magnet post that can be used with the disclosed ferromagnetic ring in some embodiments.

FIG. 16 illustrates port magnet post 120 that may be used in place of socket magnet post 20 in nasal respiratory assembly 5. Port magnet post 120 may replace socket magnet post 20 in nasal respiratory assembly 5. Port magnet post 120 includes a ball shaped receptacle 135 that cooperates with socket opening of nasal connector 90 in a ball and socket arrangement. The ball shaped receptacle is configured to pivotably move or rotate about an inner surface of socket opening while still maintaining a substantially airtight connection therewith.

In some embodiments, as shown in FIG. 16 for example, each port magnet post 120 is configured to removably attach to a respective ring 262 of sheets 227 via a plurality of magnets 250 arranged on a periphery of a sheet-facing side of magnet socket 152 is positioned about a first end of port magnet post 120. Each ring 262 includes an opening 217. Accordingly, in one embodiment, each port magnet post 120 may include a plurality of magnets 250 (as shown in FIG. 16) instead of a single ring magnet as illustrated in FIG. 14. In one embodiment, the plurality of magnets 250 may take the form of magnet pellets that are embedded within magnet socket 152 of port magnet post 120, for example, using 3D printing technics commonly known in the art. Magnet socket 152 of FIG. 16 embodiment is accordingly configured to house a plurality of magnets 250 arranged on a periphery of a sheet-facing side of magnet socket 152. In various embodiments, the polarity of the magnets 250 may be arranged such that each magnet 250 has the opposite polarity as an adjacent magnet 250. In other words, the polarity may be alternated among the plurality of magnets 250 arranged on magnet socket 152. Accordingly, the plurality of magnets 250 of alternating polarities may attach to ring 262 by magnetic attraction forces. In one embodiment, port magnet post 120 can be formed by any commonly known 3D printing technics.

The magnets 250 arranged on magnet socket 152 removably attach or couple to the ring 262 (which is a ferromagnetic ring) at an exit end of port magnet post 120. In one embodiment, magnet socket 152 is configured to move or rotate about the surface of ring 262 while continuing to maintain a substantially airtight connection at the interface between magnets 250 and ring 262. Ring 262 can thus advantageously prevent or reduce the possibility of the nasal connector 90 from inadvertently getting dislodged when the wearer of the nasal respiratory assembly 5 moves the head either when awake or sleeping to thereby allowing for the continued supply of treatment gases to a patient's (or wearer's) nare under ideal pressure. In at least one embodiment, the ring 262 can permit magnet socket 152 to move or rotate about the surface of ring 262 while continuing to maintain a substantially airtight connection therewith when the face of a patient wearing nasal respiratory assembly 5 is moved in a sudden jerky movement. In at least one embodiment, ring 262 can permit magnet socket 152 to move or rotate about the surface of ring 262 while continuing to maintain a substantially airtight connection therewith when the wearer's pillow contacts or applies a shearing force against a portion of the nasal respiratory assembly 5 or the tubing supplying fluid to the nasal respiratory assembly 5.

Figure 17:
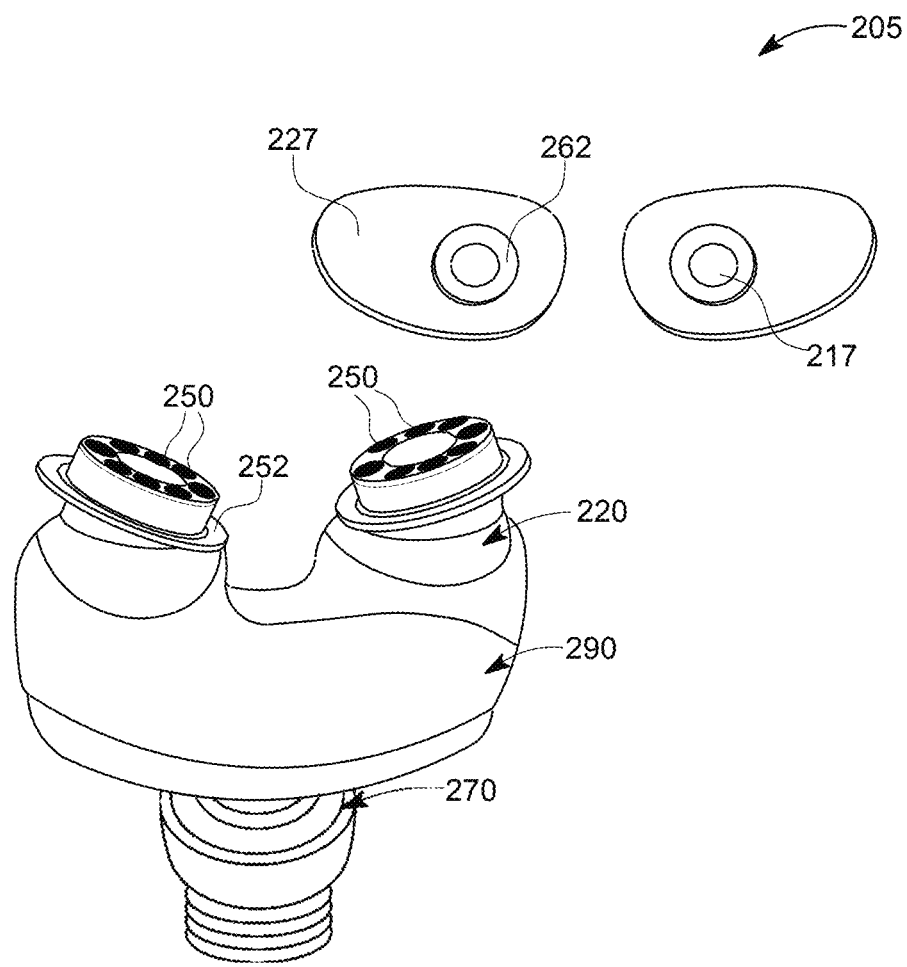
FIG. 17 is a perspective view of a nasal respiratory assembly in accordance with some embodiments of the presently disclosed subject matter.

FIG. 17 illustrates a nasal respiratory assembly 205 that includes port magnet post 220 that may be used in place of socket magnet post 20. Port magnet post 220 of nasal respiratory assembly 205 includes a receptacle that cooperates with an opening of nasal connector 290 in a substantially airtight arrangement. In one embodiment, a vent such as vent 270 is located between the vent coupling and a tubing such as tubing 12 shown in FIG. 1 to form a substantially airtight connection therewith. Vent 270 may have similar features as vent 70. In some embodiments, as shown in FIG. 17 for example, each port magnet post 220 is configured to removably attach to a respective ring 262 of sheet 227 via a plurality of magnets 250 arranged on a periphery of a sheet-facing side of magnet socket 152, with magnet socket 152 being positioned about a first end of port magnet post 220. Accordingly, in one embodiment, each port magnet post 220 may include a plurality of magnets 250 (as shown in FIG. 17), instead of a single ring magnet as illustrated in FIG. 14. In one embodiment, the plurality of magnets 250 may take the form of magnet pellets that are embedded within magnet socket 252 of port magnet post 220, for example, using 3D printing technics commonly known in the art. Magnet socket 152 of FIG. 16 embodiment is accordingly configured to house a plurality of magnets 250 arranged on a periphery of a sheet-facing side of magnet socket 252. In various embodiments, the polarity of the magnets 250 may be arranged such that each magnet 250 has the opposite polarity as an adjacent magnet 250. In other words, the polarity may be alternated among the plurality of magnets 250 arranged on magnet socket 252. Accordingly, the plurality of magnets 250 of alternating polarities may attach to ring 262 by magnetic attraction forces. In one embodiment, port magnet post 220 can be formed by any commonly known 3D printing technics.

Ring 262 may or may not have a dome shape. The upper surface of port magnet post 220 may be angled as illustrated, for example, in FIG. 17. Magnet socket 252 is positioned about a first end of the port magnet post 220. In some embodiments, magnet socket 252 (e.g., an upper surface the port magnet post 220) may be angled in relation to the body of port magnet post 220 to allow for enhanced attachment to ring 262 of sheet 227 for better positioning on a patient's nostrils.

The remaining components of nasal respiratory assembly 205 can have substantially similar or identical features as the respective components of nasal respiratory assembly 5, with the components of nasal respiratory assembly 205 labelled with numerals that include a 100th place prefix of "2" used to label respective parallel components of nasal respiratory assembly 5. For example, sheet 227 of nasal respiratory assembly 205 can be substantially similar to or identical to sheet 27 of nasal respiratory assembly 5, and so on.

Figure 18:
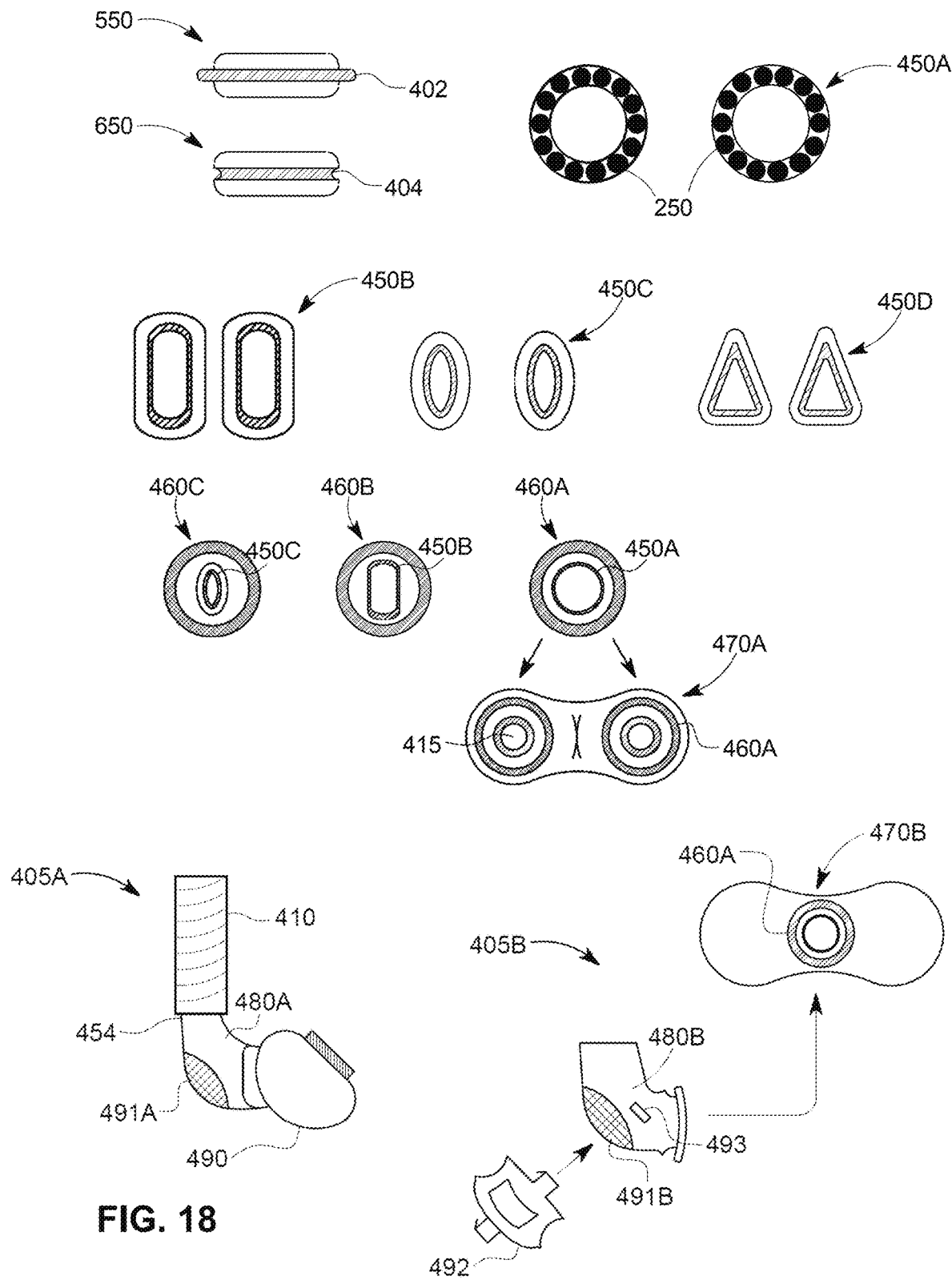
FIG. 18 includes schematic views of components of a nasal respiratory assembly in accordance with some embodiments.
Figure 19:
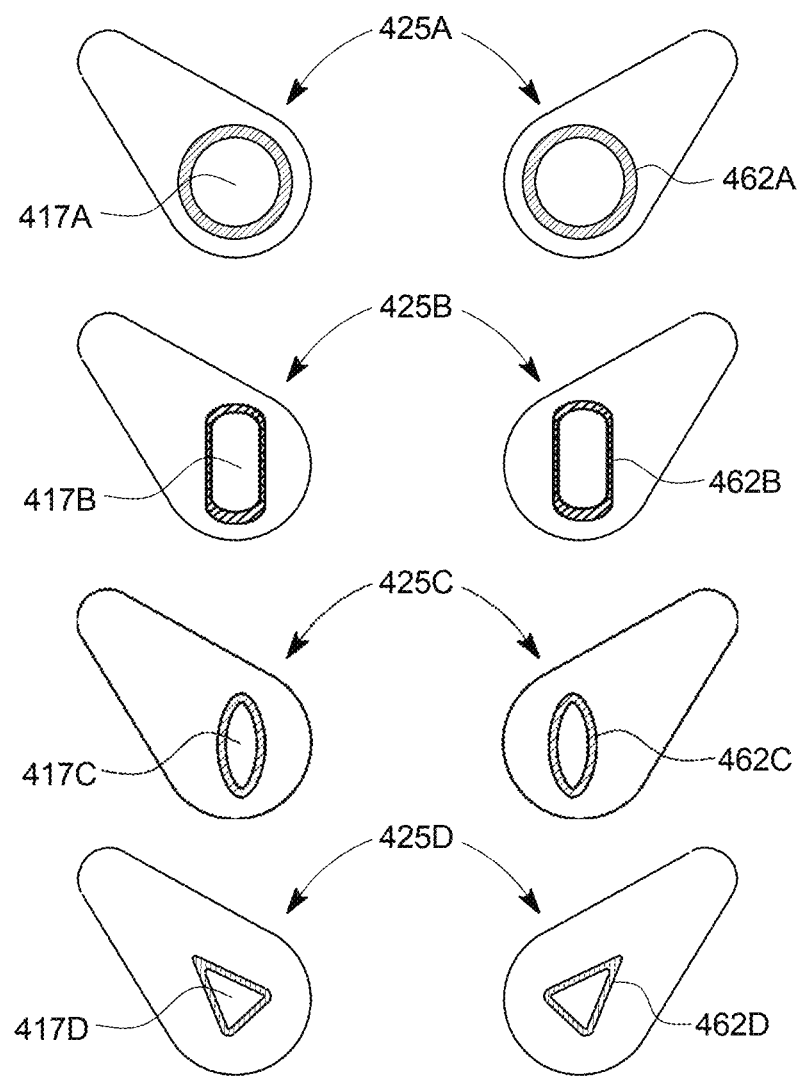
FIG. 19 includes schematic views of variable embodiments of a sheet including a ferromagnetic ring that can form part of a nasal respiratory assembly in accordance with some embodiments.

FIGS. 18 and 19 illustrate the components of nasal respiratory assembly 405A and nasal respiratory assembly 405B according to one or more embodiments of the presently disclosed subject matter. As illustrated in FIG. 18, nasal respiratory assembly 405A includes flexible tubing 410 in fluid connection with hollow elbow 480A, with swivel coupling 454 operating to provide a substantially airtight connection between flexible tubing 410 and elbow 480A. Swivel coupling 454 can conveniently allow one of elbow 480A and flexible tubing 410 to pivotally move relative to the other. The end of elbow 480A facing nasal connector 490 is sized and shaped to cooperate with a vent end of nasal connector 490 to form a substantially airtight connection therewith. Accordingly, through a hollow opening running through elbow 480A, the vent end of nasal connector 490 that faces elbow 480A is configured for fluid communication with flexible tubing 410 connected to a fluid source. Thus, in one embodiment, a hollow elbow such as elbow 480A is located between nasal connector 490 and flexible tubing 410.

Elbow 480A can include a $CO_2$ exhaust 491A sized and shaped to facilitate venting of $CO_2$ exhaled by a patient wearing nasal respiratory assembly 405A. Similarly, elbow 480B includes a $CO_2$ exhaust 491B sized and shaped to facilitate venting of $CO_2$ exhaled by a patient wearing nasal respiratory assembly 405B. Each of nasal respiratory assembly 405A and nasal respiratory assembly 405B can further include a diffuser cap 492 that removably attaches to elbow 480A via protrusions provided on the diffuser cap that engage corresponding recessed notches 493 (see FIG. 18) provided on either sides of elbow 480A and elbow 480B, the recessed notches positioned diagonally across from each other. $CO_2$ exhaust 491A operates to ensure that the patient's ability to breathe is not hampered, and to ensure excess fluid has an outlet. $CO_2$ exhaust 491A can be sized and shaped in any desired configuration and can be positioned proximal to any of the regions where fluid flow occurs. $CO_2$ exhaust 491A can vary in size and location such that manipulation of all exhaled fluids (e.g., carbon dioxide) is controlled and titratable to alter the flow rate to a desired setting. In some embodiments, $CO_2$ exhaust 491A can include polymeric fibers, membranes, and/or webs with an extremely small thickness (e.g., from nanoscale to microscale).

Nasal connector 490 can be constructed of silicone or similar other flexible material according to one or more embodiments of the presently disclosed subject matter. A sheet of nasal connector 490 located on the side of nasal connector 490 opposite to the vent end (i.e., the end opposite to the end facing elbow 480A) includes a flange such as flange 470A, as shown in FIG. 18. Flange 470A present on the sheet end of nasal connector 490 can include silicone or a similar other flexible material according to one or more embodiments of the presently disclosed subject matter. As shown in FIG. 18, flange 470A accommodates two slip rings such as slip rings 460A. 460B, 460C or 460D securely held therein, with flange 470A comprising a silicone sheet or a similar other material. Each slip ring 460A, 460B, 460C or 460D securely holds therein a respective magnet array 450A, 450B, 450C or 450D. As shown in FIG. 18, magnet array 550 includes a ridge 402 that circumferentially surrounds magnet array 550, and magnet array 650 includes a groove 404 that circumferentially surrounds magnet array 650.

In various embodiments, each magnet array 450A, 450B, 450C or 450D may be provided with either a groove 404 or a ridge 402 that circumferentially surrounds the magnet array. Groove 404 or ridge 402 of a magnetic ring in the form of magnet array 450A, 450B. 450C or 450D operates to provide an increased secure coupling between the magnetic ring in the form of magnet array 450A, 450B, 450C or 450D and a respective slip ring 460A, 460B, 460C or 460D. Each slip ring is made of a flexible material. In some embodiments, each slip ring can include a material such as LDPE (low density polyethylene) at or near its inner edge that holds magnet array 450A, and a material such as styrene butadiene copolymer (SBC) sold under the trade name K-resin® at or near it outer edge. This combination of materials forming part of the slip ring can advantageously permit round magnet array 450A, for example, to swivel within and about a respective slip ring 460A while fixed attached thereto. In various embodiments, magnet arrays 450A, 450B, 450C or 450D can take any suitable shape such as a round, oblong, oval or tear drop shape, wherein the shape of the opening of the respective ferromagnetic ring 462A, 426B, 426C or 426D compliments or matches the shape of the channel opening of the magnetic ring. The materials used in the construction of slip ring 460A, 460B, 460C or 460D can conveniently provide for magnet array 450A, 450B, 450C or 450D to pivotally move relative to the respective slip ring 460A, 460B, 460C or 460D that holds the magnet array 450A, 450B, 450C or 450D. In some embodiments, the slip ring can further include a soft playable membrane that surrounds the magnet array and fills the remaining void inside each slip ring between its outer and inner edges to help increase the comfort for the patient wearing nasal respiratory assembly by reducing or eliminating the torque that may otherwise be felt at the nose of the patient of the assembly during use of the assembly by the patient. In some embodiments, the soft playable membrane may include silicone or as similar other material that can conveniently reduce or eliminate the torque that may otherwise be felt at the nose of the patient of the assembly during use of the assembly by the patient. In some embodiments, the whole of the slip ring may consist of only the magnet array 450A, 450B, 450C or 450D and the soft playable membrane that surrounds the magnet array and fills the whole void inside the slip ring.

In some embodiments, as shown in the top right portion of FIG. 18 as an example, each magnet array 450A may include a plurality of magnets 250 arranged as a circular array, for example, instead of a single ring magnet as illustrated in FIG. 14. Accordingly, in one embodiment, each magnet array 450A may include a plurality of magnets 250 (as shown in magnet array 450A illustrated in the top right corner of FIG. 18) instead of a single ring magnet as illustrated in FIG. 14). In one embodiment, the plurality of magnets 250 may take the form of magnet pellets that are embedded within magnet array 450A, for example, using 3D printing technics commonly known in the art. Magnet array 450A of FIG. 18 embodiment is accordingly configured to house a plurality of magnets 250 arranged on a periphery of a sheet-facing side of magnet array 450A. In various embodiments, the polarity of the magnets 250 may be arranged such that each magnet 250 has the opposite polarity as an adjacent magnet 250. In other words, the polarity may be alternated among the plurality of magnets 250 arranged on each magnet array 450A. Accordingly, the plurality of magnets 250 of alternating polarities may attach to ferromagnetic ring 462A by magnetic attraction forces. In one embodiment, port magnet post 220 can be formed by any commonly known 3D printing technics.

While FIG. 18 only illustrates magnet array 450A as including an array of magnets 250, it is to be noted that each of the other magnet arrays 450B, 450C or 450D include an array of magnets 250 similar to magnet array 450A, with such magnets 250 of magnet arrays 450B, 450C or 450D not being shown in FIG. 18 due to limitation of space. Each of magnet arrays 450A, 450B, 450C or 450D can magnetically attach with a respective ferromagnetic ring 462A, 462B, 462C or 462D (see FIG. 19) of sheet 425A, 425B, 425C or 425D (see FIG. 19) through magnetic attraction forces to form a substantially airtight connection therewith. In various embodiments, each magnet array 450A, 450B, 450C or 450D is accordingly configured to removably attach to a respective ferromagnetic ring 462A, 462B, 462C or 462D via the plurality of magnets 250 arranged on a periphery of a sheet-facing side of each magnet array 450A, 450B, 450C or 450D. Provision of ferromagnetic rings 462A-462D of various circumferential shapes laid onto sheets 425A-425D can allow for an improved patient experience when integrated into a nasal respiratory assembly 405A or nasal respiratory assembly 405B capable of being installed upon a patient.

In some further embodiments, an inner portion of the space between an outer perimeter of the magnet array and the outer contour of the slip ring (i.e., the portion contiguous to the outer perimeter of the magnet array) includes a slender, loose, extremely flexible, and forgiving thin-layer of silicone that is configured to bounce in an out relative to the slip ring or relative to the magnet array to help accommodate movements initiated by the patient during use of the nasal respiratory assembly to reduce torque. In the same embodiments, an outer portion of the space between an outer perimeter of the magnet array and the outer contour of the slip ring (i.e., the portion contiguous to the outer perimeter of the slip ring) can include a silicon layer that is less slender, less flexible, and thicker relative to the portion that is contiguous to the outer perimeter of the magnet array. Further, the material of the flange 470A directly adjoining and encircling the slip ring too can include a silicon layer that is less slender, less flexible, and thicker relative to the portion that is contiguous to the outer perimeter of the magnet array. Such an arrangement can help further increase the comfort level for the patient wearing nasal respiratory assembly by reducing or eliminating the torque that may otherwise be felt at the nose of the patient of the assembly during use of the assembly by the patient.

In various embodiments, the outer perimeter of slip rings 460A, 460B, and 460C may be of a standard dimension, whereas the dimensions of the perimeter of the inner opening of the slip rings can vary, with the size and shape of the inner opening configured and adapted for the respective magnet array to be received therein; in other words, the inner opening of the slip ring is sized and shaped for securely holding the magnet array to be received therein. Thus, the dimensions of the inner opening cane be different for each of round magnet array 450A, oblong shaped magnet array 450B, oval shaped magnet array 450C and tear drop shaped magnet array 450D.

For example, round magnet array 450A held in place by slip ring 460A magnetically attaches to ferromagnetic ring 462A (see FIG. 19) of sheet 425A (see FIG. 19) to form a substantially airtight connection therewith. During use of the nasal respiratory assembly 405A by a patient, when round magnet array 450A is detachably attached to ferromagnetic ring 462A of sheet 425A (see FIG. 19), upper ends of channel openings 415 on round magnet arrays 450A of nasal connector 490 are in fluid communication with the interior of the nostrils of the wearer, whereas the lower ends of channel openings 415 are in fluid communication with the interior of nasal connector 90 such that respiratory fluid flows from flexible tubing 410, through elbow 480A, through each channel opening 415 of flange 470A, and through opening 417A of each sheet 425A and into the interior of the nostrils of the wearer. Thus, each channel opening 415 comprises a unique pathway for conveying fluid from a fluid source to the nasal passage of the patient.

Nasal respiratory assembly 405A can further include a pair of sheets such as sheet 425A, 425B, 425C or 425D, each sheet defining an opening sized and shaped to fit over the nostril of a patient, with a respective ferromagnetic ring 462A, 462B, 462C or 462D positioned at an underside of the sheet and circumferentially aligned with the opening, with an upper side of the sheet configured for scalable engagement with the nostril. Channel opening 415 of round magnet array 450A has a circular cross-section, which compliments/matches the circular cross-section of opening 417A of sheet 425A. Channel opening 415 of round magnet array 450B has an oblong cross-section, which compliments/matches the oblong cross-section of opening 417B of sheet 425B. Channel opening 415 of round magnet array 450C has an oval cross-section, which compliments/matches the oval cross-section of opening 417C of sheet 425C. Channel opening 415 of round magnet array 450D has a tear drop cross-section, which compliments/matches the tear drop cross-section of opening 417D of sheet 425D. Accordingly, each of magnet arrays 450A, 450B, 450C or 450D is configured to engage with a respective ferromagnetic ring 462A, 462B, 462C or 462D (see FIG. 19) of sheet 425A, 425B, 425C or 425D (see FIG. 19). Each sheet 425A, 425B, 425C or 425D is configured to engage a nostril of the patient. Each sheet 425A, 425B, 425C or 425D directly contacts the exterior of a patient's nostril or the skin surrounding the patient's nostril. The sheets can be configured for providing a flush, scalable engagement with the patient's nares.

In various embodiments, each sheet 425A, 425B, 425C or 425D engages with or includes one or more flexible adhesive sheets (not shown) to provide scalable engagement with the patient's nostrils. Sheet 425A, 425B, 425C or 425D can be constructed from any known material, including (but not limited to) woven fabric, plastic, and/or latex. For example, in some embodiments, sheet can be constructed from PVC, polyethylene, polyurethane, latex, or combinations thereof. In some embodiments, sheet 425A, 425B, 425C or 425D can be a foam medical tape, a surgical tape, and/or a hypoallergenic tape. The patient contacting surface of sheet 425A, 425B, 425C or 425D can include an adhesive. The adhesive can be any medically safe adhesive known or used in the art. For example, the adhesive can be selected from one or more acrylates (such as methacrylate, alkyl acrylate, or epoxy diacrylate), acrylic acids, polyvinyl chloride, alkyl esters, or combinations thereof. In some embodiments, the adhesive is a pressure-sensitive adhesive such that the sheet can be adhered and removed from the patient's skin as desired. The adhesive can be selected to show mild or no irritation to the skin when used daily. In some embodiments, the adhesive tape can be configured as a hydrocolloid tape and/or can include a polyurethane reactive layer that adheres more to the nostril as the patient's body temperature warms up the adhesive. Alternatively, in some embodiments, the adhesive can be directly applied to the patient's nostril or the nasal engaging portion to provide a removeable connection (e.g., no sheet is used). In various embodiments, each sheet 425A, 425B, 425C or 425D or the adhesive present therein is configured to match the shape of each respective magnet array 450A, 450B, 450C or 450D (shown in FIG. 18).

In various embodiments, providing for the magnet arrays 450A, 450B, 450C or 450D to rest directly or indirectly against or near a surface of the nose can significantly reduce torque. Additionally, the ability of magnet arrays 450A, 450B, 450C or 450D to shift and spin will help in significantly reducing torque. In other words, the ability of magnet arrays 450A, 450B, 450C or 450D to pivotally move relative to a slip ring 460A, 460B, 460C or 460D that securely holds the magnet array 450A, 450B, 450C or 450D while the respective magnet array 450A, 450B, 450C or 450D maintains an airtight connection with a respective ferromagnetic ring 462A, 462B, 462C or 462D can help increase the comfort for the patient wearing nasal respiratory assembly by reducing or eliminating the torque that may otherwise be felt at the nose of the patient of the assembly during use of the assembly by the patient.

Accordingly, in various embodiments, nasal respiratory assembly 405A can comprise a pair of sheets 425C, each sheet 425C defining an opening sized and shaped to fit over the nostril of a patient, with a ferromagnetic ring 462C positioned at an underside of the sheet and circumferentially aligned with the opening, with an upper side of the sheet 425C configured for scalable engagement with the nostril. Nasal respiratory assembly 405A further comprises a nasal connector 490 including a pair of slip rings 460C at a sheet end, each slip ring 460C including a magnet arrays 450C defining a channel opening 415, the magnet arrays 450C configured to pivotably tilt about the slip ring 460C, each magnet array 450C sized and shaped to removably attachable to one of the ferromagnetic rings 462C to form a substantially airtight connection therewith, and an inlet at a vent end that is fluid communication with a flexible tubing 410 connected to a fluid source, wherein the channel opening has an oval shape. In various embodiments, the channel openings can also have a round, oblong, oval or tear drop or a similar other shape. The opening of the ferromagnetic ring can have a shape that compliments/matches the shape of the channel opening of the magnetic ring. For example, the opening 417C of the ferromagnetic ring 462C can have an oval shape that compliments/matches the oval shape of the channel opening of the magnetic ring.

In at least one embodiment, each magnet array 450A, 450B, 450C or 450D may removably attach to a respective ring 262 (see FIG. 17) of sheets 227 via the plurality of magnets 250 arranged on a periphery of a sheet-facing side of each magnet array 450A, 450B, 450C or 450D.

Nasal respiratory assembly 405A can further comprise hollow elbow 480A connecting the inlet at the vent end of the connector to flexible tubing 410 connected to the fluid source. In some embodiments, swivel coupling 454 can connect hollow elbow 480A to flexible tubing 410.

The bottom right side of FIG. 18 further illustrates a nasal respiratory assembly 405B according to one or more embodiments of the presently disclosed subject matter. Nasal respiratory assembly 405B can have same or similar components as nasal respiratory assembly 405A except as explained herein. Nasal respiratory assembly 405B may omit a nasal connector such as nasal connector 490; in other words, in nasal respiratory assembly 405B, flange 470B may attach directly to a sheet end of elbow 480B, the sheet end being positioned opposite to the side of elbow 480B that includes swivel coupling 454. Swivel coupling 454 connects to flexible tubing 410 such that swivel coupling 454 can allow for flexible tubing 410 to swivel relative to elbow 480B. $CO_2$ exhaust 491B can be configured similar to, or identical to $CO_2$ exhaust 491A. In some embodiments, nasal respiratory assembly 405B can include pairs of flexible tubing 410, elbow 480B, and flange 470B-one for each nostril. In some embodiments, flange 470B can include two slip rings on a same single flange, as shown, for example, with regard to flange 470A of FIG. 18. Nasal respiratory assembly 405B can be otherwise be similar or identical to, and operate similar as, nasal respiratory assembly 405A in all other respects.

The remaining components of nasal respiratory assembly 405A and nasal respiratory assembly 405B can have substantially similar or identical features as the respective components of nasal respiratory assembly 5, with the components of nasal respiratory assembly 405A/405B labelled with numerals that include a 100th place prefix of "4" used to label respective parallel components of nasal respiratory assembly 5. For example, sheet 427 of nasal respiratory assembly 405A/405B can be substantially similar to or identical to sheet 27 of nasal respiratory assembly 5, and so on. In some embodiments, the remaining components of nasal respiratory assembly 405A and nasal respiratory assembly 405B can have substantially similar or identical features as the respective components of nasal respiratory assembly 105, with the components of nasal respiratory assembly 405A/405B labelled with numerals that include a 100th place prefix of "4" instead of "1" used to label respective parallel components of nasal respiratory assembly 105. For example, magnetic array 450 of nasal respiratory assembly 405A/405B can be substantially similar to or identical to magnet 250 of nasal respiratory assembly 205. As a further example, sheet 425 of nasal respiratory assembly 405A/405B can be substantially similar to or identical to sheet 125 of nasal respiratory assembly 205, and so on.

According to at least one embodiment, nasal respiratory assembly 405A/405B comprises a pair of sheets 425A, 425B, 425C or 425D, each sheet 425A, 425B, 425C or 425D defining an opening sized and shaped to fit over a nostril of a patient, with a ferromagnetic ring 462A, 462B, 462C or 462D positioned at an underside of the sheet and circumferentially aligned with the opening, with an upper side of the sheet 425A, 425B, 425C or 425D configured for scalable engagement with the nostril. Nasal respiratory assembly 405A/405B further includes a nasal connector 490. The nasal connector 490 includes: a pair of slip rings 460A, 460B, 460C or 460D at a sheet end, each slip ring 460A, 460B, 460C or 460D accommodating a magnetic ring in the form of magnet array 450A, 450B, 450C or 450D. Each slip ring 460A, 460B, 460C or 460D defines a channel opening. the magnetic ring comprising an array of magnets. The magnetic ring in the form of magnet array 450A, 450B, 450C or 450D is configured to pivotably tilt about the slip ring. The magnetic ring in the form of magnet array 450A, 450B, 450C or 450D is sized and shaped to be removably attachable to one of the ferromagnetic rings 462A, 462B, 462C or 462D to form a substantially airtight connection therewith. Nasal respiratory assembly 405A/405B further includes an inlet at a vent end that is fluid communication with a flexible tubing connected to a fluid source. The channel opening has a round, oblong, oval or tear drop shape. The opening of the ferromagnetic ring has a round shape (e.g., ferromagnetic ring 462A) oblong shape (e.g., ferromagnetic ring 462B), oval shape (e.g., ferromagnetic ring 462C) or tear drop shape (e.g., ferromagnetic ring 462D), wherein the shape of the opening of the ferromagnetic ring matches the shape of the channel opening of the magnetic ring in the form of magnet array 450A, 450B, 450C or 450D. The array of magnets may include magnets 250 concentrically arranged at the sheet end of the slip ring 460A, 460B, 460C or 460D. The slip ring may be 3D printed.

Figure 20:
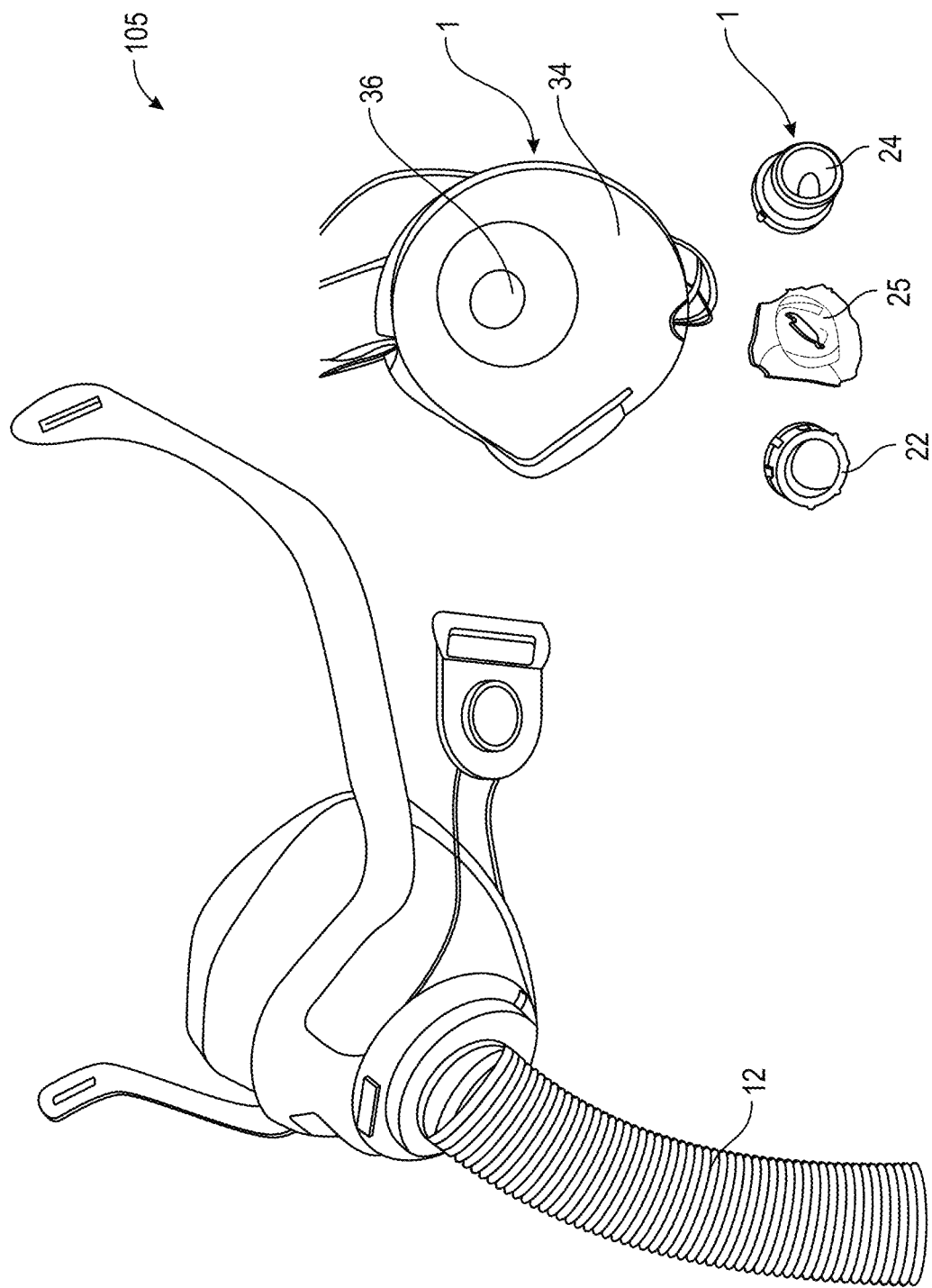
FIG. 20 illustrates another CPAP respiratory assembly that can be used in conjunction with the respiratory mask assembly illustrated in FIG. 3, in accordance with some embodiments of the presently disclosed subject matter.

FIG. 20 illustrates a nasal respiratory assembly 105 that can be installed upon a patient along with respiratory mask assembly 10, according to one or more embodiments of the presently disclosed subject matter. Nasal respiratory assembly 105 can accordingly replace nasal respiratory assembly 5 of respiratory mask assembly 10 in at least one embodiment. Nasal respiratory assembly 105 can accordingly be used in conjunction with coupler 100 and respiratory mask 1.

Figure 21:
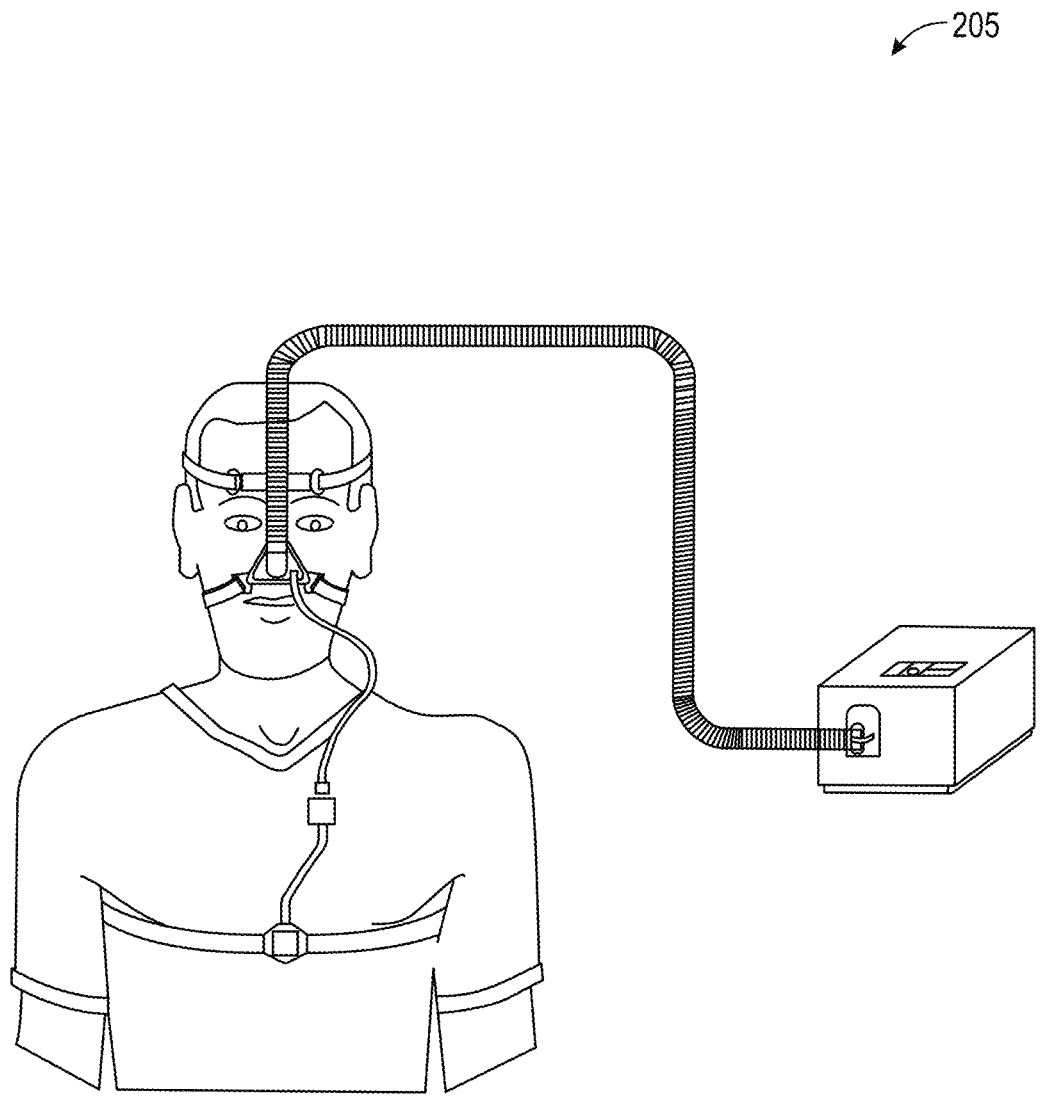
FIG. 21 illustrates a further CPAP respiratory assembly that can be used in conjunction with the respiratory mask assembly illustrated in FIG. 3, in accordance with some embodiments of the presently disclosed subject matter.
Figure 22A:
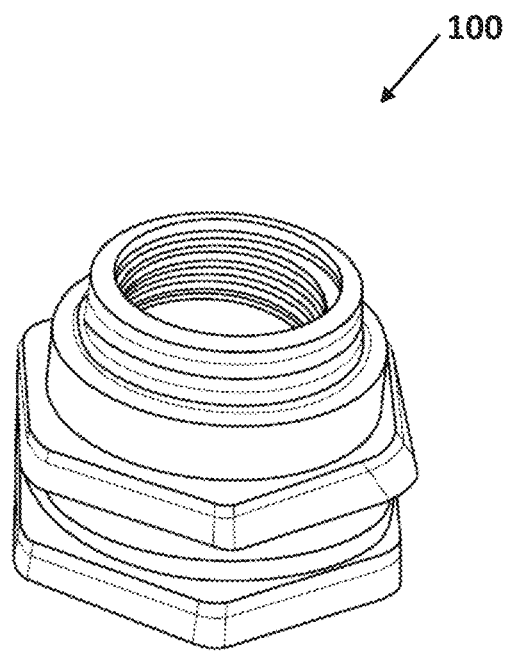
FIGS. 22A. 22B, 22C, 23A, 23B, 23C, 24A, 24B, 24C. 24D and 25 illustrate additional embodiments and aspects of a conduit coupler that can be used in conjunction with the respiratory mask illustrated in FIG. 3, in accordance with some embodiments of the presently disclosed subject matter.
Figure 22B:
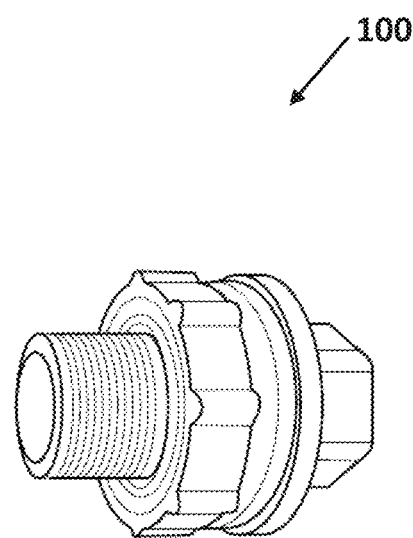
Figure 22C:
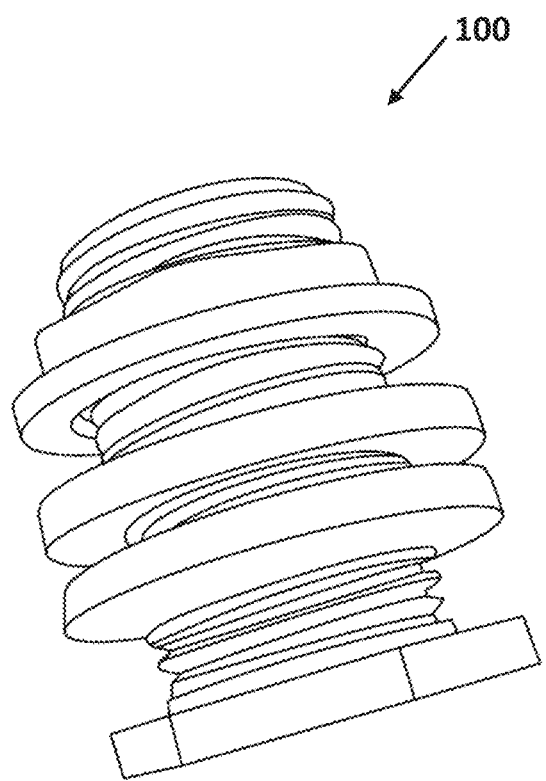
Figure 23A:
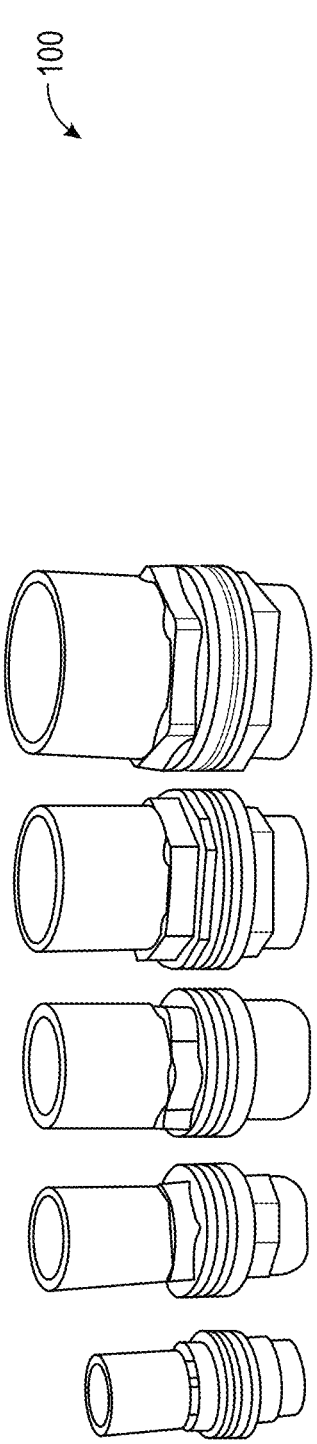
Figure 23C:
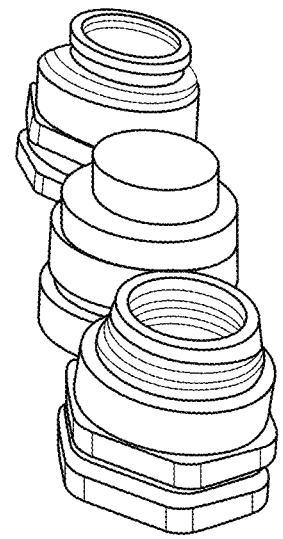
Figure 23B:
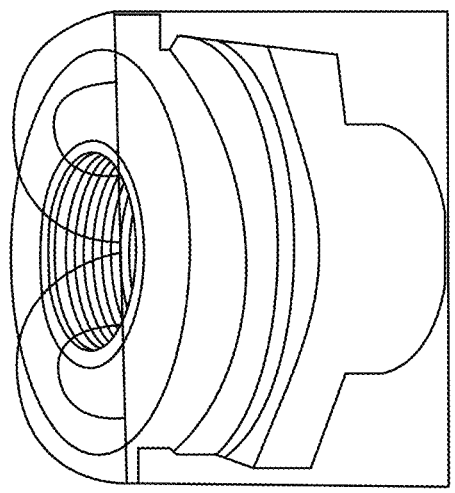
Figure 24C:
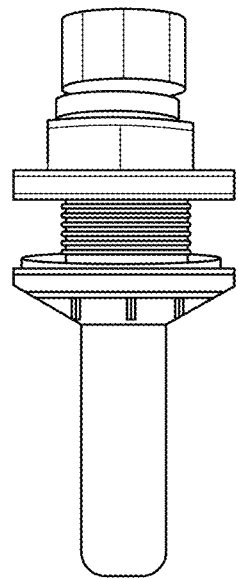
Figure 24D:
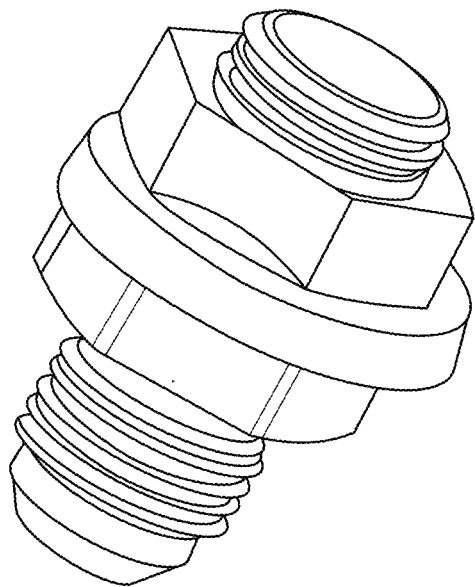
Figure 24A:
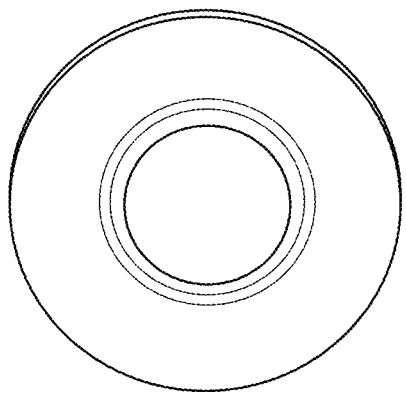
Figure 24B:
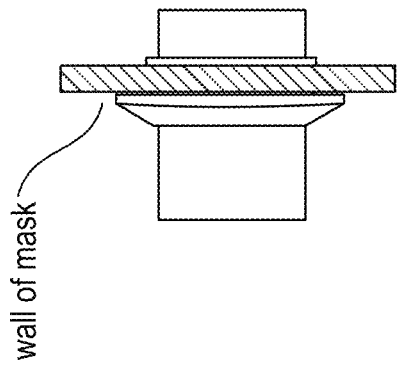
Figure 25:
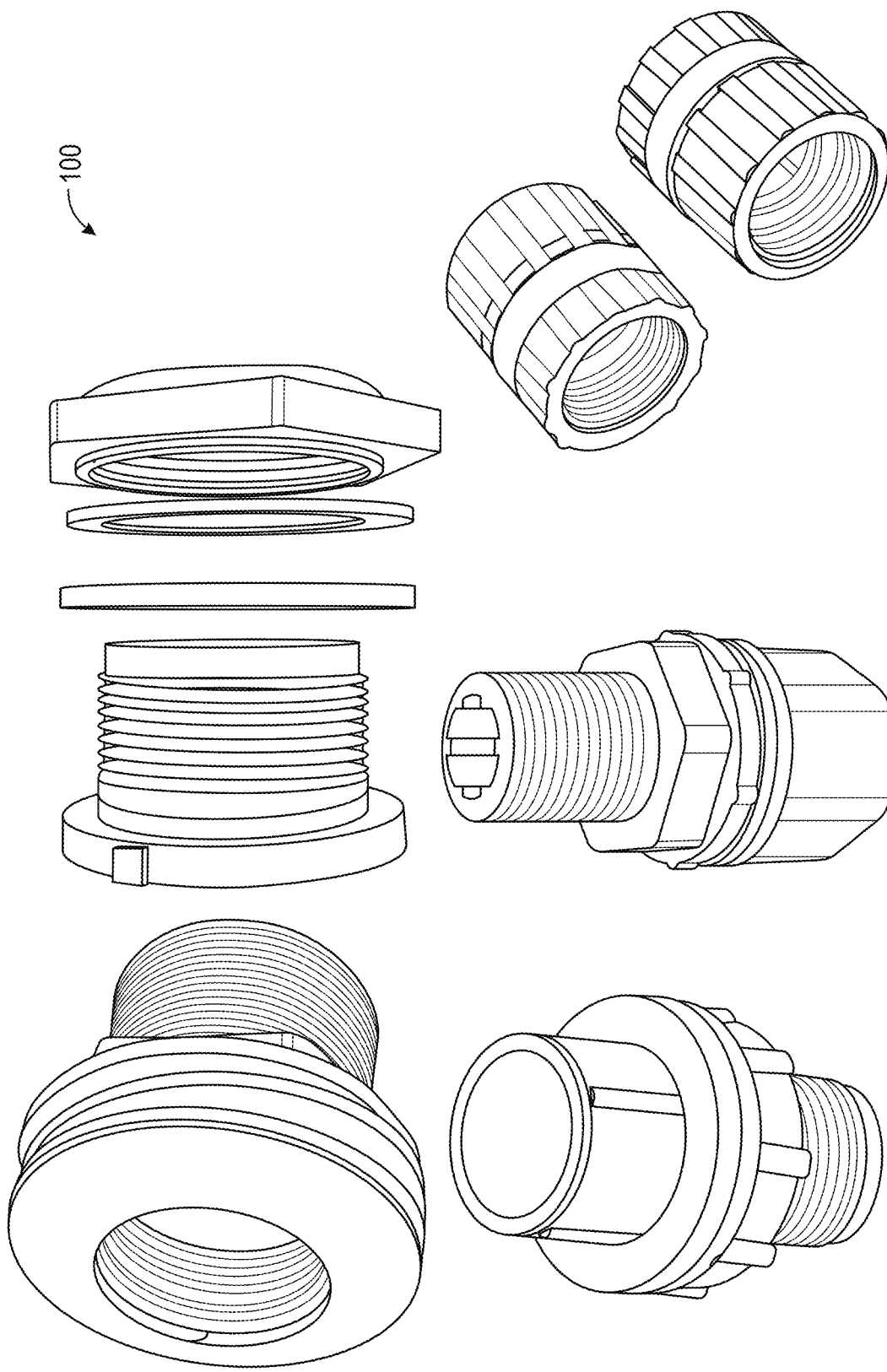

FIG. 21 illustrates a nasal respiratory assembly 605 that can be installed upon a patient along with respiratory mask assembly 10, according to one or more embodiments of the presently disclosed subject matter. Nasal respiratory assembly 605 can accordingly replace nasal respiratory assembly 5 of respiratory mask assembly 10 in at least one embodiment.

FIGS. 22 through 25 illustrate additional embodiments and additional embodiments of coupler 100 that can form part of respiratory mask assembly 10, according one or more embodiments of the presently disclosed subject matter. In various embodiments, the gasket can take various sizes and shapes without deviating from the spirit of the invention.

Respiratory mask 1 as described herein and coupler 100 as described herein can be used in conjunction with any generic CPAP masks, CPAP assemblies, and other positive airway pressure masks and breathing aids. Respiratory mask 1 as described herein and coupler 100 as described herein can further be used in conjunction with any generic respiratory masks including N95 respirators, surgical masks, and any other respirators that can filter particulate matter or microbes that available in the market currently and in future.

Figure 3:
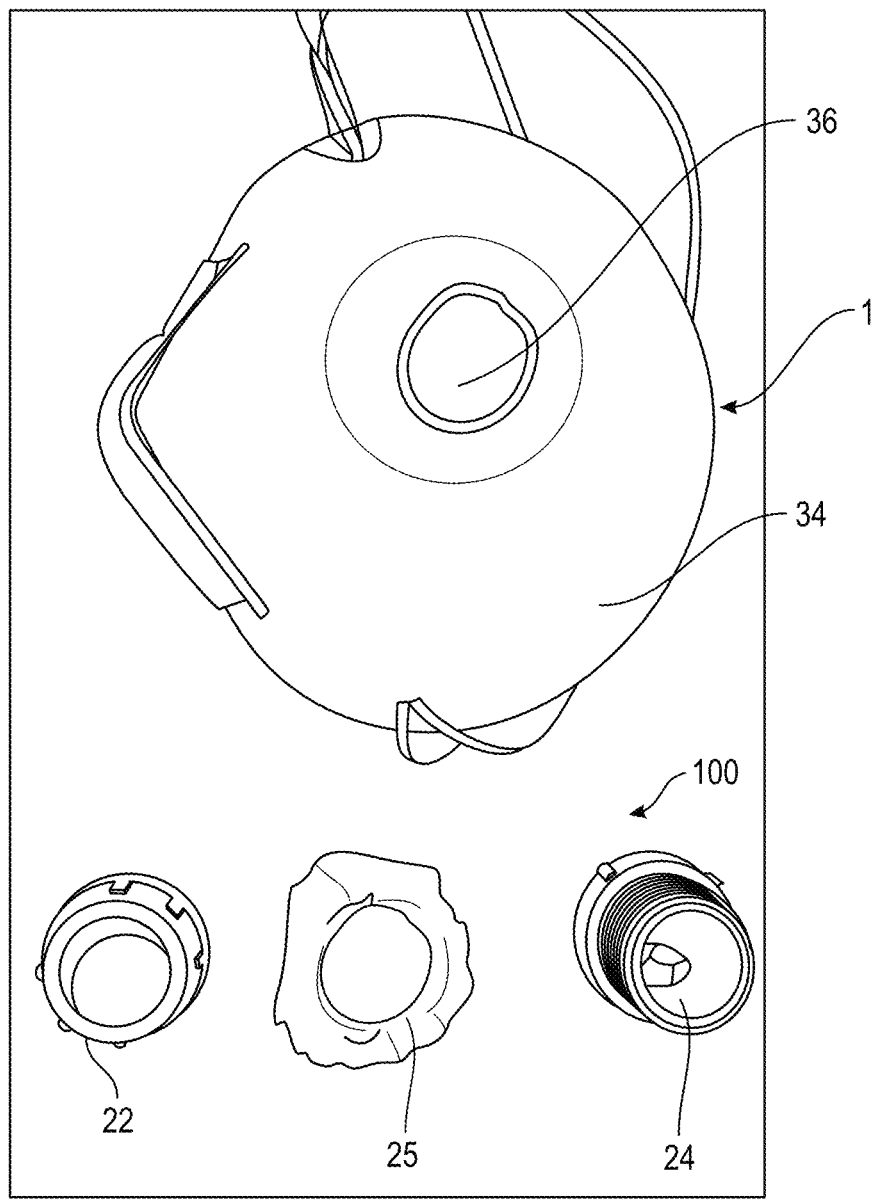
FIG. 3 illustrates a perspective view of an outer side of the respiratory mask assembly in a disassembled configuration along with the disassembled parts of a coupler that forms part thereof, in accordance with some embodiments of the presently disclosed subject matter.
Figure 4:
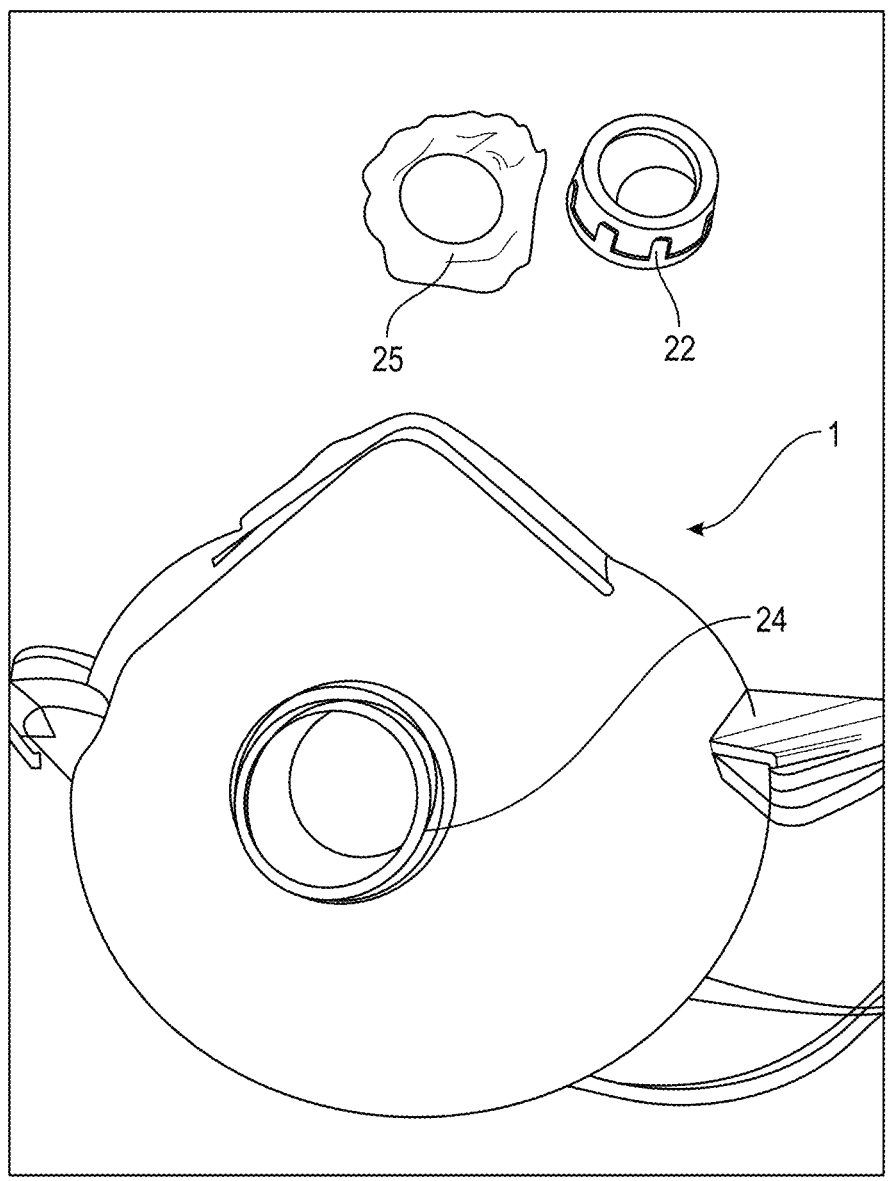
FIG. 4 illustrates a perspective view of an outer side of a respiratory mask assembly with a male member inserted through a central opening of the respiratory mask assembly, in accordance with some embodiments of the presently disclosed subject matter.
Figure 5:
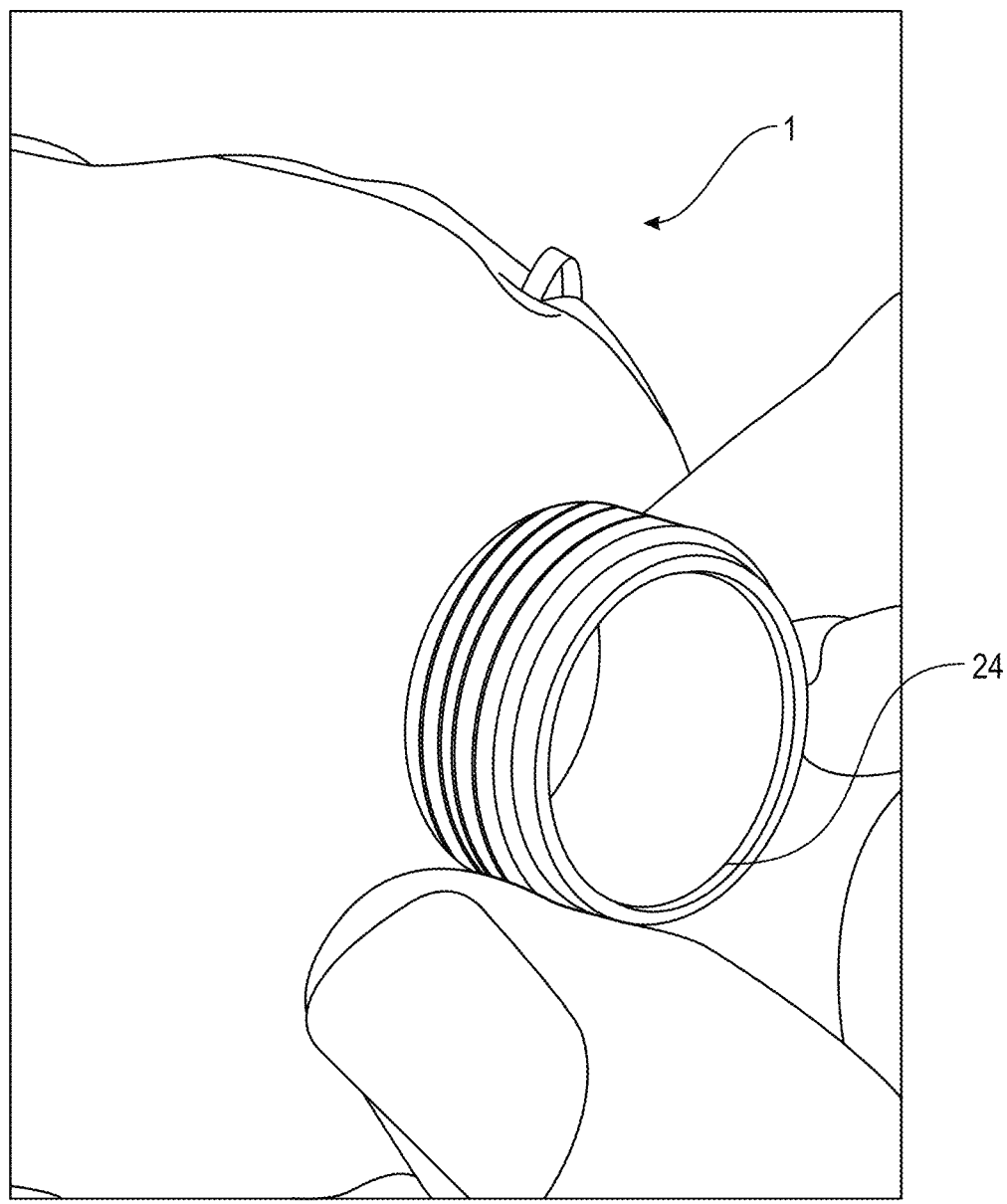
FIG. 5 illustrates a side perspective view of an outer side of a respiratory mask assembly with a male member inserted through a central opening of the respiratory mask assembly, in accordance with some embodiments of the presently disclosed subject matter.
Figure 6:
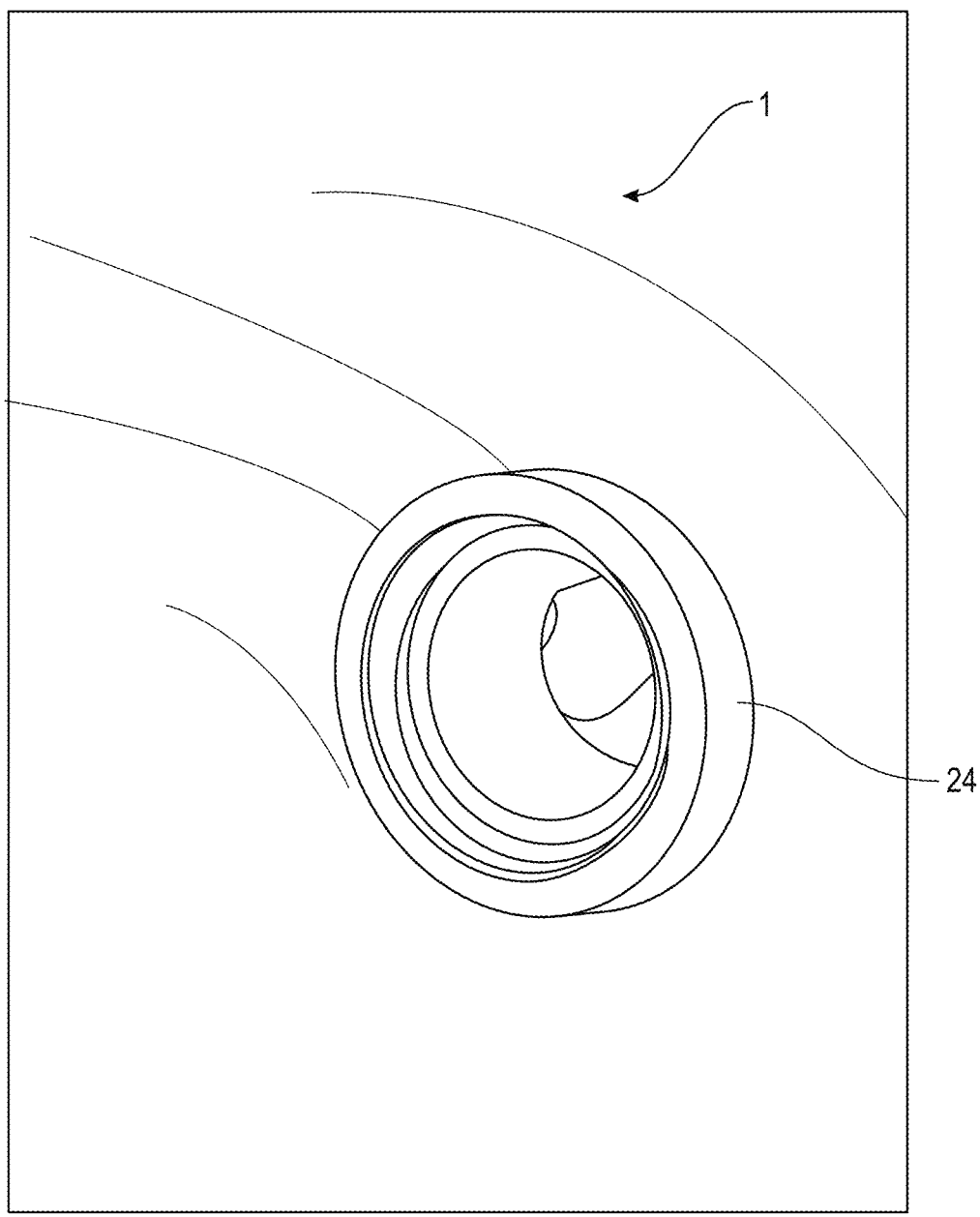
FIG. 6 illustrates a perspective view of a portion of an inner side of the respiratory mask assembly with the male member inserted through the central opening, in accordance with some embodiments of the presently disclosed subject matter.
Figure 7:
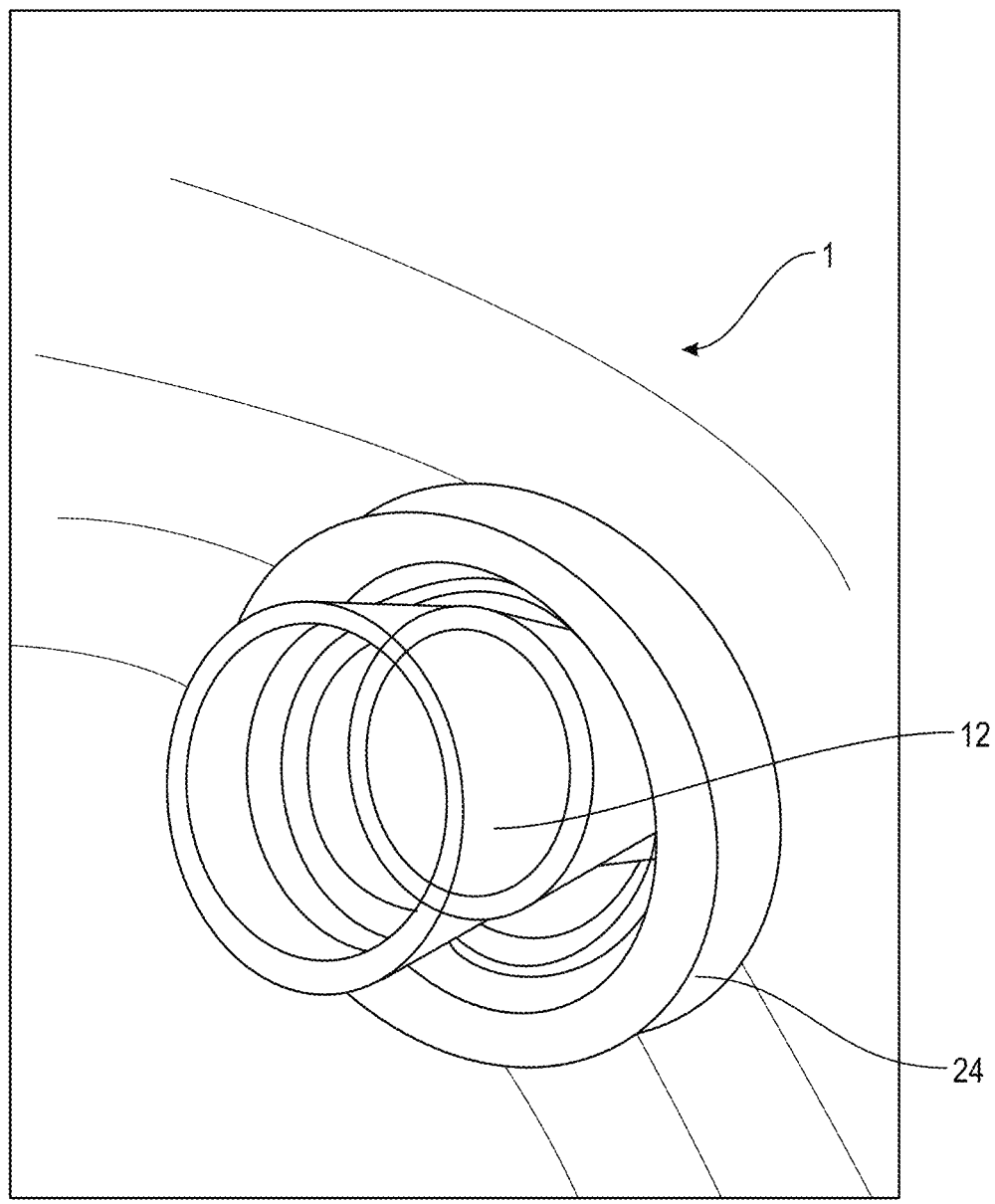
FIG. 7 illustrates a perspective view of a portion of the inner side of a respiratory mask assembly with a flexible tubing inserted through the male member, in accordance with some embodiments of the presently disclosed subject matter.
Figure 8:
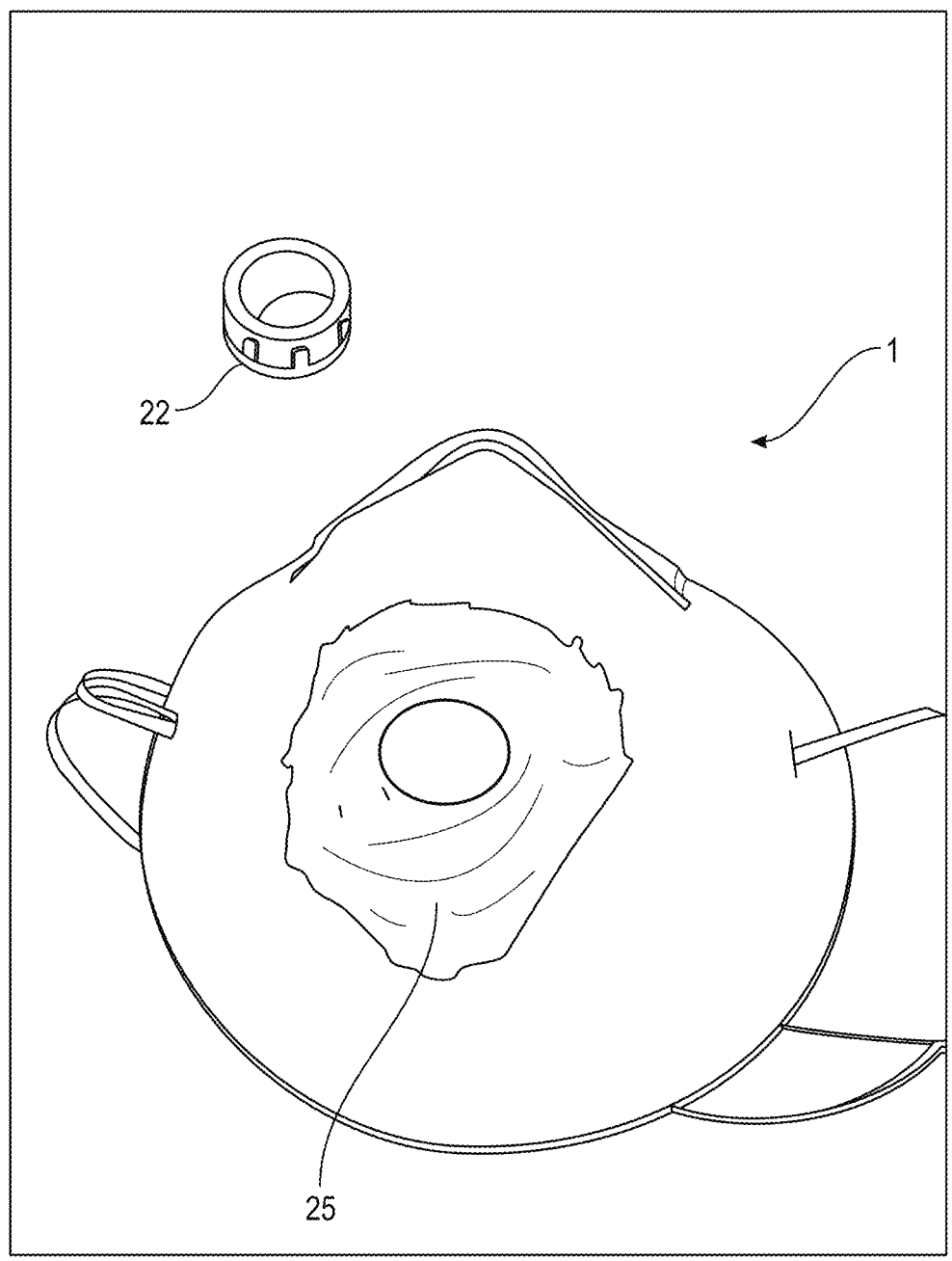
FIG. 8 illustrates a perspective view of an outer side of a respiratory mask assembly with a gasket placed on top of the male member inserted through the central opening of the respiratory mask assembly, in accordance with some embodiments of the presently disclosed subject matter.
Figure 9:
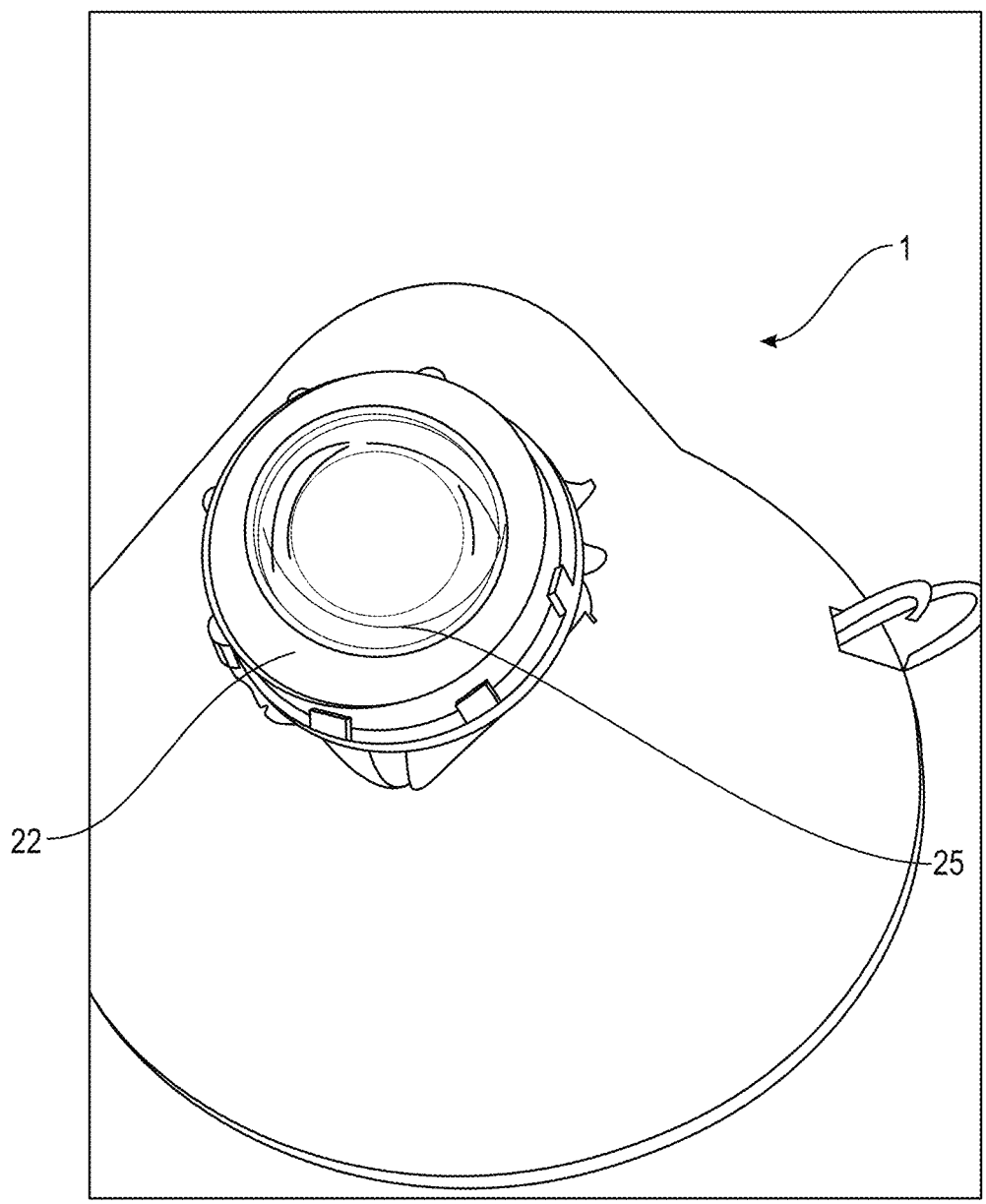
FIG. 9 illustrates a perspective view of the outer side of a respiratory mask assembly with the female member removably coupled to the male member without the tubing inserted therethrough for illustration purposes, in accordance with some embodiments of the presently disclosed subject matter.
Figure 10:
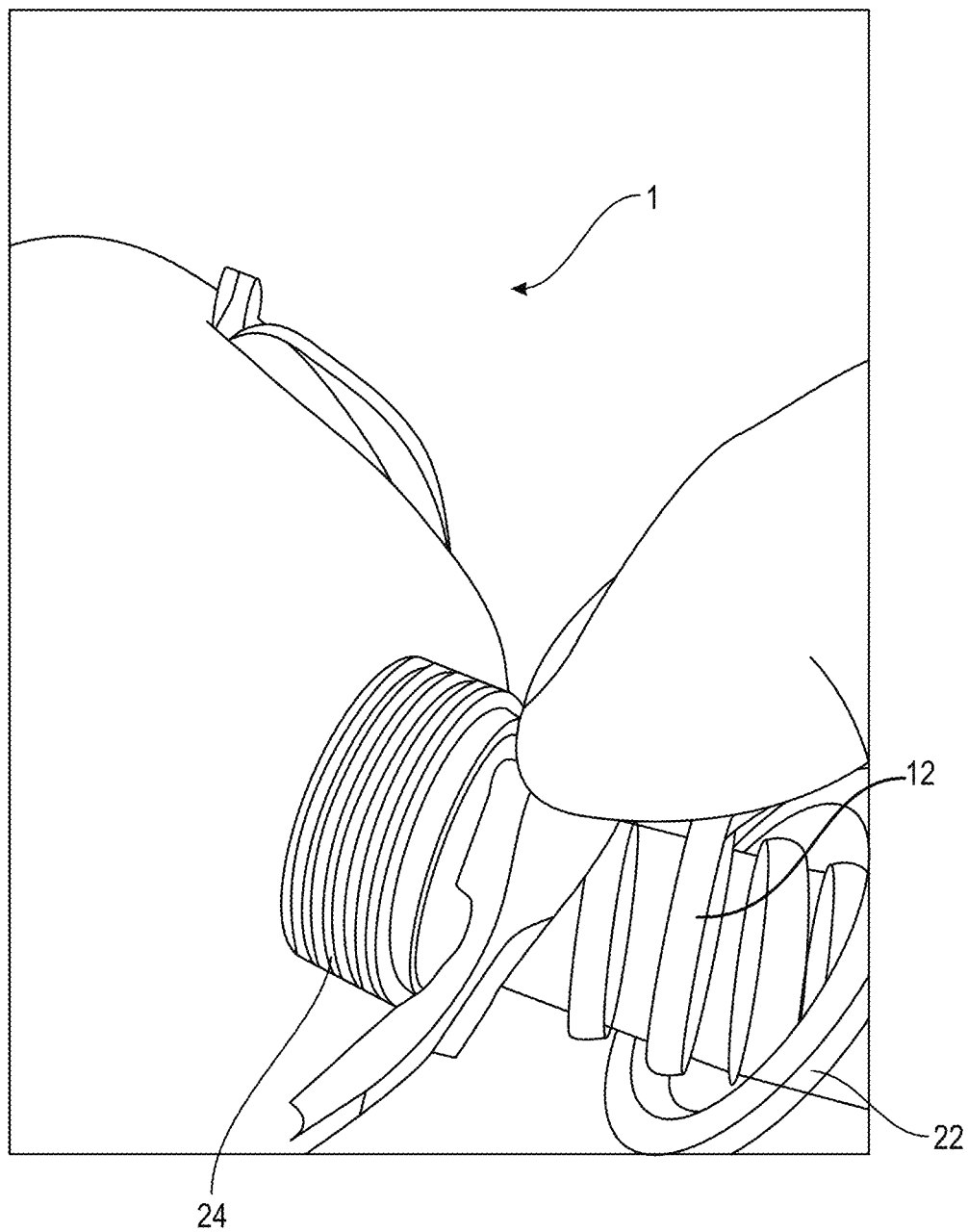
FIGS. 10 and 11 illustrate side perspective views of the outer side of a respiratory mask assembly with the female member about to be removably coupled to the male member with a CPAP tubing inserted through both the male and female members, in accordance with some embodiments of the presently disclosed subject matter.
Figure 11:
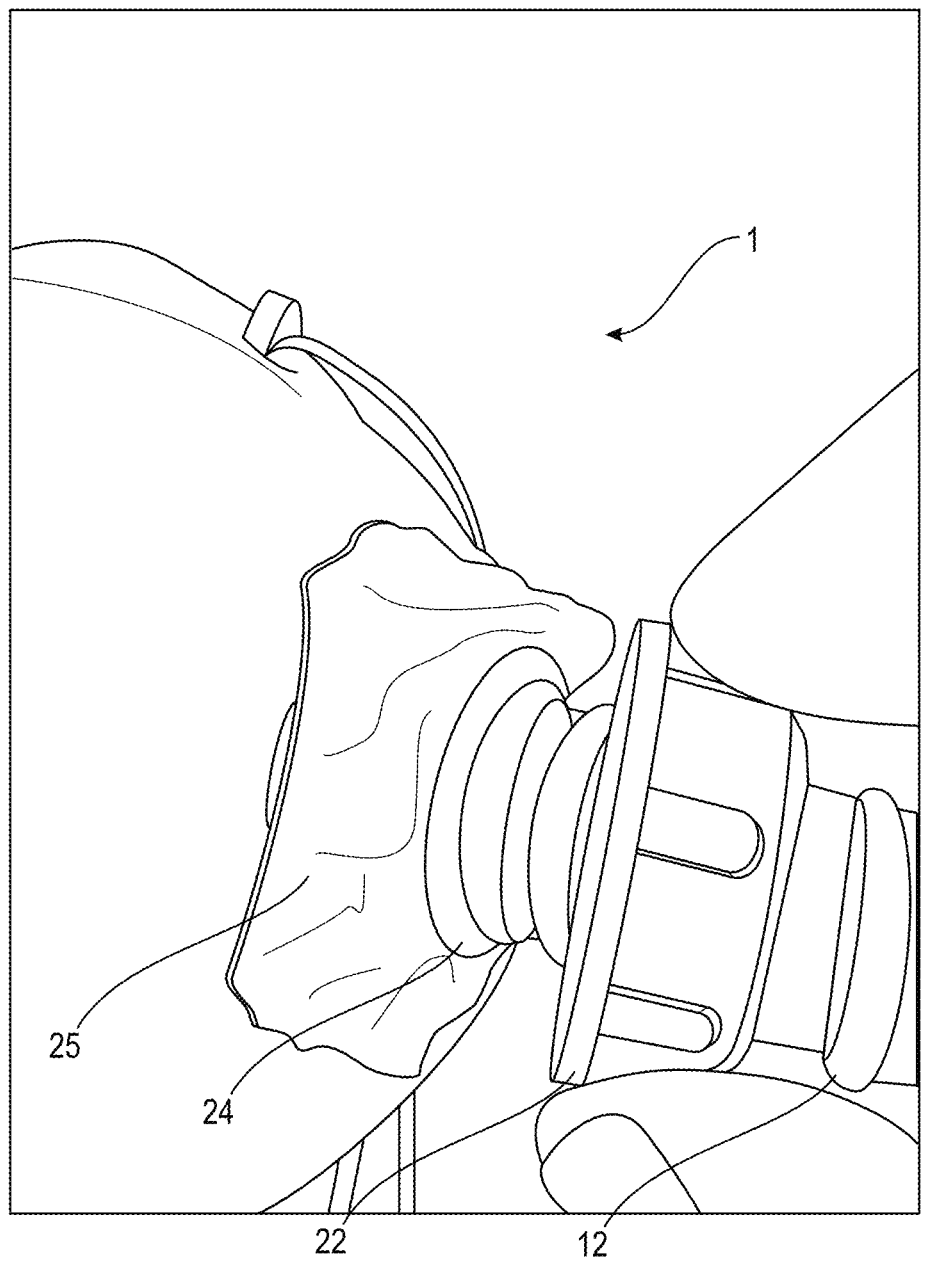
Figure 12:
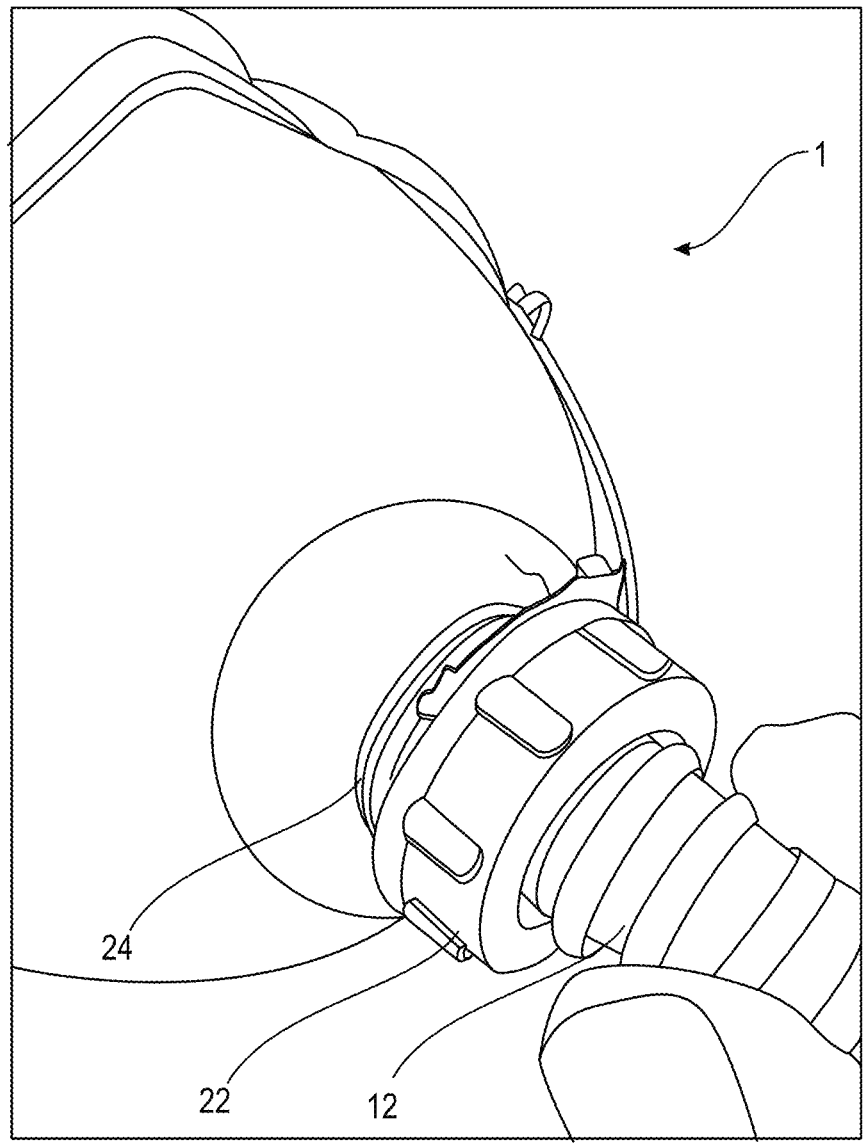
FIG. 12 illustrates a side perspective view of the outer side of a respiratory mask assembly with a CPAP tubing inserted through both the male and female members, in accordance with some embodiments of the presently disclosed subject matter.
Figure 26:
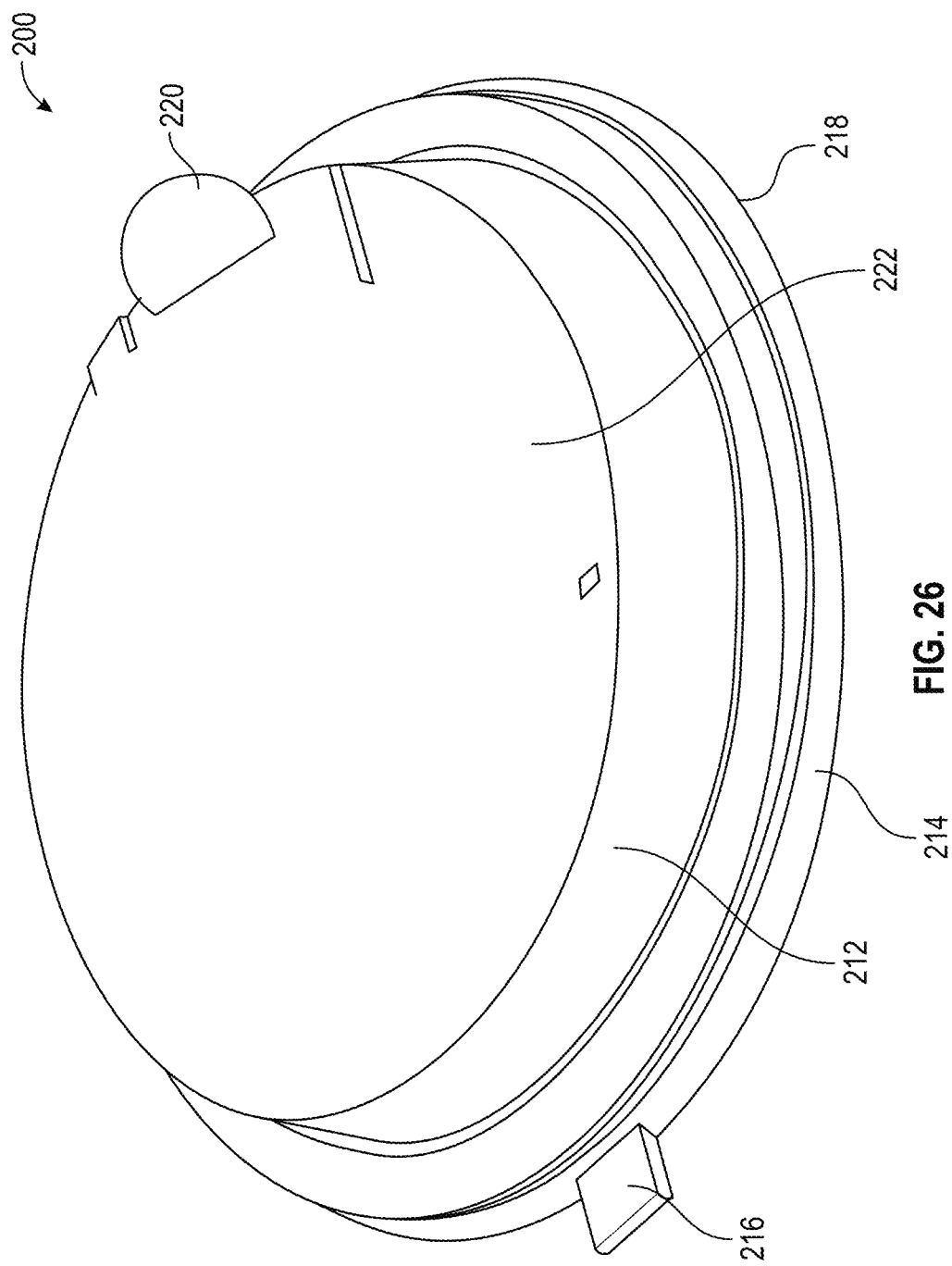
FIG. 26 illustrates a schematic perspective view of a snap-on lid that can be built into the respiratory mask assembly illustrated in FIG. 3 for controlling access to a central opening of the respiratory mask, in accordance with some embodiments of the presently disclosed subject matter.

FIG. 26 shows a schematic perspective view of a snap-on lid 200 provided on respiratory mask 1 for providing access to central opening 36 formed on respiratory mask 1. In various embodiments, access to central opening 36 (shown in FIG. 3) can be made by opening exterior cover 212 provided on snap-on lid 200. Snap-on lid 200 can have a substantially flat top in a closed position. Accordingly, in some embodiments, snap-on lid 200 is provided on respiratory mask 1 covering central opening 36 of respiratory mask 1 whereby exterior cover 212 of snap-on lid 200 can be opened to provide access to central opening 36. Exterior cover 212 has been folded over the frame 214 provided around the circumference of central opening 36. When exterior cover 212 is folded over and snapped onto frame 214 to snap close snap-on lid 200, a substantially airtight seal is formed between exterior cover 212 of snap-on lid 200 and frame 214 of snap-on lid 200. Tab 221 is provided on snap-on lid 200 for snapping exterior cover 212 open as well as for snapping exterior cover 212 close.

Exterior cover 212 can be folded over and snapped onto frame 214 to snap close snap-on lid 200 by folding the hinge 216 connecting exterior cover 212 and frame 214. Frame 214 can include an outer lip 218 that seals frame 214 around the rim or circumference of central opening 36 formed on a respiratory mask such as respiratory mask 1. In various embodiments, snap-on lid 200 can include an exterior cover 212 is a hinged relationship with a frame 214 provided on the rim or circumference of central opening 36 formed on respiratory mask 1. In various embodiments, frame 214 is molded into, glued to, or otherwise integrated with the fabric that respiratory mask 1 is formed of. The top surface of the elevated portion 222 of exterior cover 212 is substantially planar. In various embodiments, central opening 36 is configured to accommodate any tubing 12 connected to a fluid supply that supplies a fluid from a device such as a CPAP fluid supply source, a high flow technology device, and any other noninvasive ventilation options.

Figure 27:
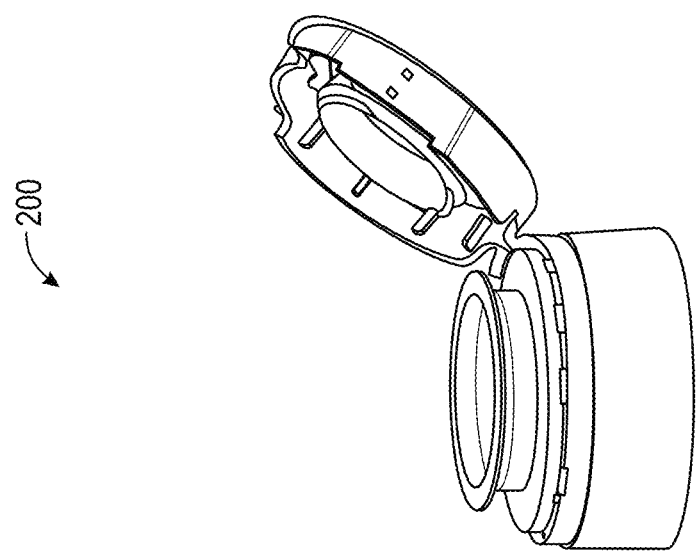
FIG. 27 illustrates additional embodiments of snap-on lids that can be built into a respiratory mask such as a N95 respirator or other generic CPAP masks, CPAP assemblies, and other positive airway pressure masks and breathing aids, in accordance with some embodiments of the presently disclosed subject matter.
Figure 27:
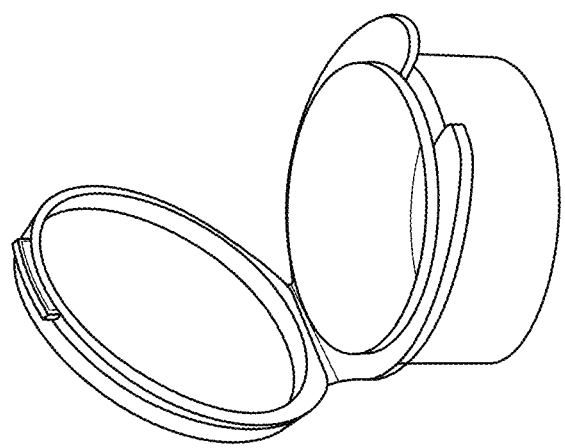
Figure 27:
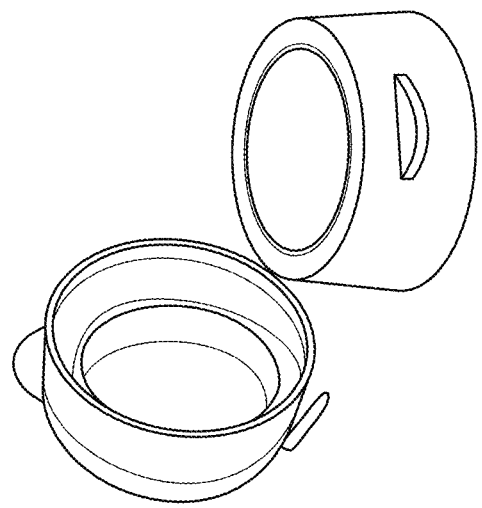

FIG. 27 illustrates some additional embodiments of snap-on lid 200 that can be built into a respiratory mask 1 such as a N95 respirator. The snap-on lid as described herein can be used in conjunction with any generic CPAP masks, CPAP assemblies, and other positive airway pressure masks and breathing aids. The snap-on lid as described herein can further be used in conjunction with any generic respiratory masks including N95 respirators, surgical masks, and any other respirators that can filter particulate matter or microbes that available in the market currently and in future.

In some embodiments, coupler 100 can be inserted through frame 214 after exterior cover 212 is opened to expose central opening 36, following which gasket 25 forming part of coupler 100 operates to engage with or includes one or more flexible adhesive sheets (not shown) to provide scalable engagement with one or more of the male member, the female member, frame 214, an interior wall or interior surface 32 of the respiratory mask, and an exterior surface 34 of the respiratory mask.

In some embodiments, the frame 214 can be provided with a sealing mechanism that provides a substantially airtight seal around tubing 12 inserted therethrough whereby a coupler 100 may not be needed. In various embodiments, the sealing mechanism can be an adhesive layer, a peel-back glue, or a similar other sealing mechanism. In at least one embodiment, the sealing mechanism can be in the form of an elastomeric membrane or a gasket (similar to gasket 25 described earlier) extending from, or otherwise coupled to frame 214, that is configured to form a substantially airtight seal between tubing 12 and frame 214.

FIG. 28 through FIG. 31 illustrate various aspects of polymagnets forming part of a continuous positive airway pressure (CPAP) mask such as nasal respiratory assembly 5 that couples to one or more of a patient's nare and mouth, in accordance with some embodiments of the presently disclosed subject matter. In some embodiments, each magnetic ring 50 can be in the form of one or more programmed magnets or polymagnets 350 as illustrated, for example, in FIGS. 28 through 31. In some embodiments, ring 262 may be replaced with, or may otherwise comprise, polymagnets 350. Similarly, in some embodiments, magnets 250 as mentioned herein too can represent polymagnets 350. In some embodiments, each magnetic ring 50 can be in the form of a plurality of polymagnets 350 arranged as an array on a periphery of a sheet-facing side of magnet socket 52 is positioned about a first end of socket magnet post 20. In an alternate embodiment, each magnetic ring 50 can be in the form of a single ring polymagnet provided on a periphery of a sheet-facing side of magnet socket 52 is positioned about a first end of socket magnet post 20. Accordingly, in at least one embodiment, each socket magnet post 20 may include a magnetic ring 50 comprising one or more polymagnets 350 forming an array as shown in FIG. 15, instead of a magnetic ring 50 comprising a single ring polymagnet 350 as illustrated in FIG. 14.

In one embodiment, the one or more polymagnets 350 may further take the form of poly magnet pellets that are embedded within magnetic ring 50 of socket magnet post 20, for example, using 3D printing technics commonly known in the art. Magnetic ring 50 can accordingly include one or more polymagnets 350 arranged as an array on a periphery of a sheet-facing side of magnetic ring 50. In various embodiments, the polarity within each polymagnet 350 and among polymagnets 350 may be arranged such as to maximize the intended effect of maintaining a substantially airtight coupling between magnetic ring 50 and ring 262, with such coupling otherwise not inadvertently detached during sleep of the wearer of the CPAP equipment. For example, in one embodiment, both magnetic ring 50 and ring 262 may be latch polymagnets, as described herein.

Accordingly, in at least one embodiment, the one or more polymagnets 350 of magnetic ring 50 may have alternating polarities, with magnetic ring 50 attaching to ring 262 by magnetic attraction forces. In one embodiment, socket magnet post 20 comprising one or more polymagnets 350 can be formed by 3D printing technics. In one embodiment, ring 262 comprising one or more polymagnets 350 can be formed by 3D printing technics. In at least one embodiment, one or more polymagnets 350 may be substantially planar. In various embodiments, a plane of the one or more polymagnets 350 may be substantially planar to a transverse plane passing through the center of magnetic ring 50. In various embodiments, the one or more polymagnets 350 may be concentrically arranged.

Polymagnets 350 as illustrated in FIGS. 28A through 31F may represent magnetic structures that incorporate correlated patterns of magnets with alternating polarity, designed to achieve a desired behavior and deliver stronger local force. By varying the magnetic fields and strengths, different mechanical behaviors may be controlled. Polymagnets 350 can be programmed, or coded, by varying the polarity and/or field strengths of each source of the arrays of magnetic sources that make up each structure. The resulting magnetic structures can be one-dimensional, two-dimensional, three-dimensional, and even four-dimensional if produced using an electromagnetic array. In one embodiment, the coding theory used to design radio frequency signals in communication and radar can be applied to form the magnetic regions of correlated magnets. A 3D magnetizing printer such as, for example, the "MagPrinter" developed by the U.S firm Correlated Magnetics Research (CMR), Huntsville, AL, may be used to fabricate polymagnets 350. This printer consists of a magnetizing coil in a cabinet with a motion-control system. In various embodiments, a polymagnet printer can be used to create multi-pole encoded magnets that contain small magnetic elements called maxels. This technology can be used to produce superior attachment forces, safer magnets, precision alignment, shear and torque stiffness, and complex, multi-level/multi-force control on a scale that is not easy to achieve with traditional magnets. The polymagnet printer uses engineered encoding of polarity patterns into a magnet and can be tailored to meet specific application requirements, allowing for: magnets with unique functions; multiple forces per magnetic surface; stronger forces-especially on the magnet face; control the 'reach' and 'shape' of the magnetic field; and enhanced break away off and sheer forces, which may be several times stronger than found in conventionally magnetized materials.

Figure 28A:
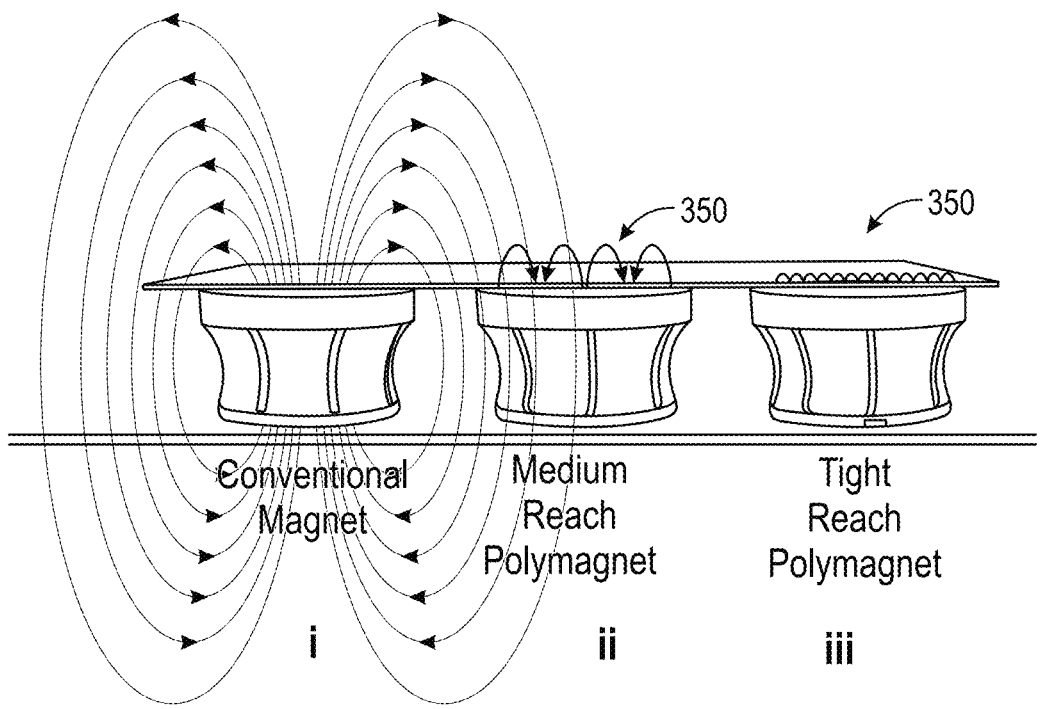

Polymagnet 350 can accordingly be made from reprogramming a conventional magnetic material in a few minutes. With Polymagnets, magnetic coupling can have softer 'feel' or snappier or crisper closing or opening behavior, and may be given the sensation of a spring or latch. On a conventional magnet, there is a North (N) pole on one surface and a South(S) pole on the opposite surface (see FIG. 28Ai, FIG. 28Bii, FIG. 28Ci, and FIG. 28Di), with magnetic field lines flowing around the magnetic from pole to pole. By contrast, on a polymagnet, many small, polarized (N or S) magnetic pixels ("maxels") are manufactured by printing in a desired pattern on the same surface (see FIG. 28Aii, FIG. 28Aiii, FIG. 28Bi, FIG. 28Cii, and FIG. 28Dii), with the magnetic field lines being completed between the maxels on that surface, resulting in a very compact, strong magnetic field. This basic concept is shown in FIG. 28Aii, FIG. 28Aiii, FIG. 28Bi, FIG. 28Cii, and FIG. 28Dii. Accordingly, the mechanical 3-D behavior of a polymagnet such as polymagnet 350 may be determined by the pattern and strength of the maxels embedded on the surface of the magnet. The customizable behaviors include spring, latch, shear, align, snap, torque, hold, twist, soften and release. The compact magnetic field set up reduces magnetic interference with other equipment.

Most off the shelf magnets have a simple nature. North on one side, south on the other. In polymagnets, rather than simple arrangements of north and south, customizable patterns can be designed in software and programmed into a magnet in minutes. Polymagnets can be manufactured in any quantity from prototype to production volumes. Since the pattern is created in software, it can be changed, and new prototypes delivered in days. Conventional magnets do not necessarily align when attaching to each other while polymagnets can be programed to achieve various types of alignments. Polymagnets can be configured as very strong magnets because their magnetic energy has been concentrated near the surface. Polymagnets can be up to 5× stronger than conventional magnets.

Polymagnets, when used in pairs, can leverage the attraction, and repel forces of magnetism, exploiting the idea of controlled cancelation or interaction of these forces in space. The arrangement or pattern of magnetic regions (called maxels) can create a unique magnetic circuit that defines the function of the magnetic device and its interaction with other magnets or ferrous metals. Correlated magnet pairs (e.g., a magnetic ring 50 in the form of one or more polymagnets and a ring 262 in the form of one or more polymagnets) can be programed to attract or repel with a prescribed force and engagement distance, or, to attract or repel at a certain spatial orientation. Correlated magnets can be programmed to interact only with other magnetic structures that have been coded to respond. Correlated magnets can even be programmed to attract and repel at the same time.

Compared to conventional magnets, the correlated magnet provides much stronger holding force to the target and stronger shear resistance. The programmable behavior can be achieved by creating multipole structures comprising multiple magnetic elements (maxels) of varying size, location, orientation, and saturation. The sizes of maxels range from 1 mm to 4 mm. By overlapping these maxels, a very intricate magnetic field can be produced. Correlated magnetic structures can be developed from ferrites, rare-earth materials (e.g., neodymium magnet, samarium-cobalt magnet), ceramics, and electromagnets alike, and the correlation effects are scalable from very large permanent magnets to nanometer-scale devices. Multi-pole magnetic devices may be constructed from discrete permanent magnets, or by exposing heated magnetizable material to a coded magnetic field. Polymagnets can be designed to align with a wide variety of alignment functions. There are four main functions that correlated magnets can achieve:

Attach Polymagnets (see FIG. 29A)—The magnetic field of attach polymagnets is designed to be close to the surface of the magnet. This feature provides greater safety from a distance and concentrates the field making it stronger. For best results, a traction tape may be used.

Latch Polymagnets (see FIG. 29D)—latch polymagnets are configured to repel until the magnet pair pass through a defined transition point, and after the transition point, they reverse polarity and attract. They can be used on sliding and rotating latches.

Spring Polymagnets (see FIG. 29B and FIG. 29C)—spring polymagnets are configured to attract until they pass through a defined transition point, and beyond the transition point they will repel, and can be configured to come to rest at an equilibrium distance.

Align Polymagnets (see FIG. 30A and FIG. 30B)—conventional magnets do not necessarily align when attaching to each other whereas polymagnets may be designed to align with a wide variety of alignment functions. Align polymagnets can provide for rotational alignment, twist release and axial centering. Rotational alignment polymagnets (see FIG. 30B) are designed to attach together and have a rotational detent or alignment position. Twist release polymagnets-attract in one position and repel when rotated. Centering alignment polymagnets (see FIG. 30A) are designed to attach together with high shear/slide force.

Figure 28B:
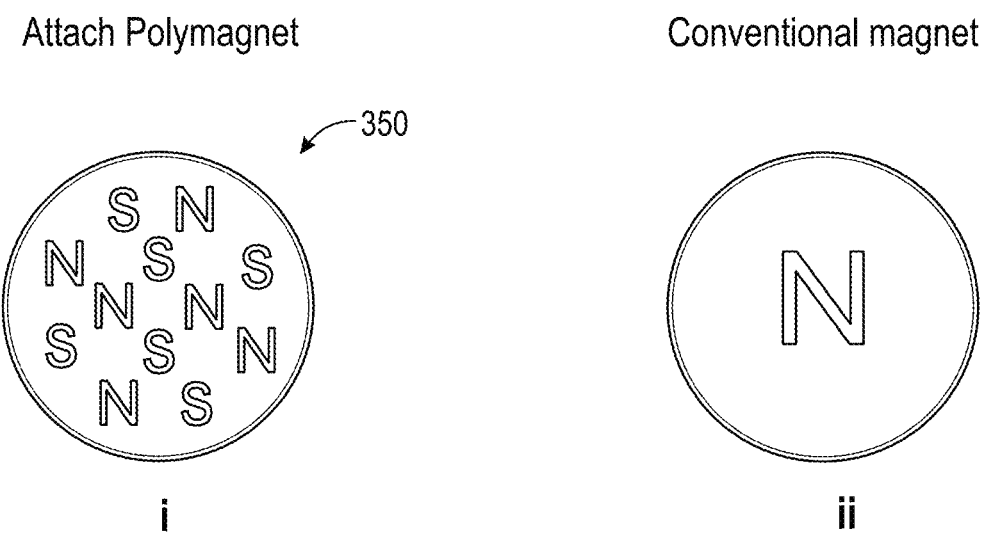

FIG. 28Ai illustrates magnetic field lines of a conventional magnet with magnetic field lines flowing from a single north pole to a single south pole. FIG. 28Bii illustrates a conventional magnet including a single north pole and a single south pole.

FIG. 28Aii and FIG. 28*iii* illustrate magnetic field lines of a poly magnet that includes many small, polarized (N or S) magnetic pixels ("maxels") manufactured by printing in a desired pattern on the same surface, with the magnetic field lines being completed between the maxels on that surface, resulting in a very compact, strong magnetic field.

FIG. 28Ci illustrates magnetic field lines of a bar shaped conventional magnet with magnetic field lines flowing from a single north pole to a single south pole. FIG. 28Di illustrates the conventional magnet of FIG. 28Ci attached to a ferromagnetic bar.

FIG. 28Ci illustrates magnetic field lines of a bar shaped polymagnet that includes many small, polarized (N or S) magnetic pixels, with the magnetic field lines being completed between each set of north pole south pole combination, resulting in a very compact, strong magnetic field. FIG. 28Dii illustrates the polymagnet of FIG. 28Cii attached to a ferromagnetic bar.

Figure 29A:
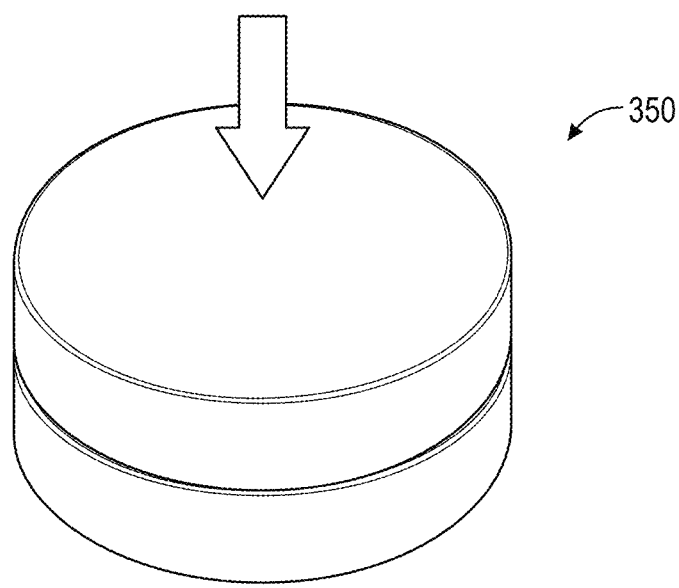
FIGS. 29A-29D illustrate various aspects of customized polymagnets forming part of a CPAP nasal respiratory assembly configured for engaging the nostrils of a patient, in accordance with some embodiments of the presently disclosed subject matter.

FIG. 29A illustrates two attach polymagnets wherein the magnetic field is designed to be close to the surface of the magnet. This feature provides greater safety from a distance and concentrates the field making it stronger.

Figure 29B:
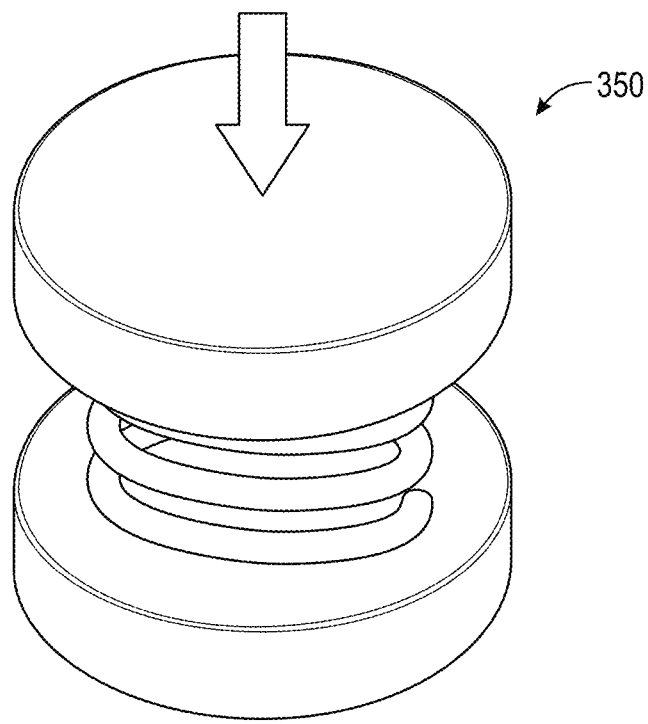

FIG. 29B illustrates two spring polymagnets configured to attract until they pass through a defined transition point, and beyond the transition point they will repel, and can be configured to come to rest at an equilibrium distance.

Figure 29C:
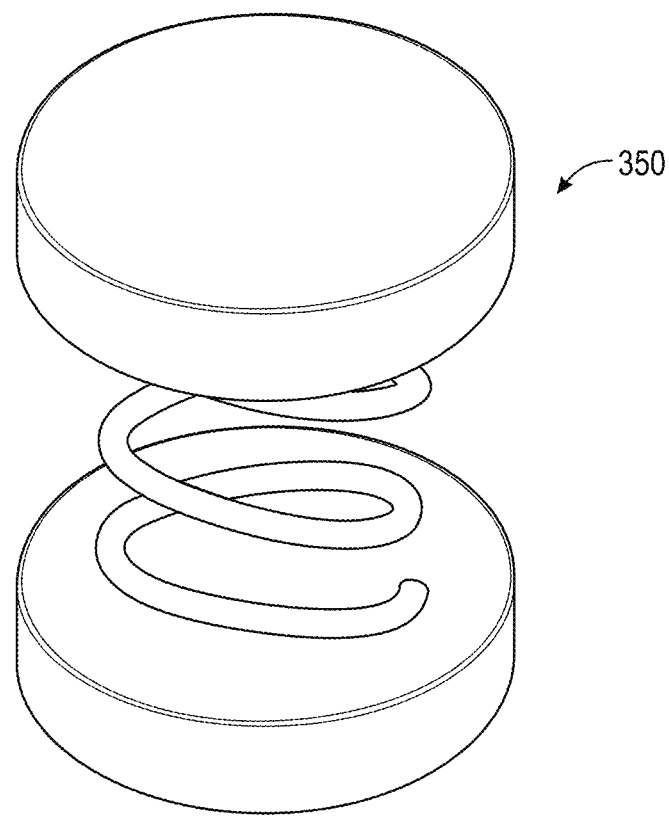

FIG. 29C illustrates another set of two spring polymagnets configured to attract until they pass through a defined transition point, and beyond the transition point they will repel, and can be configured to come to rest at an equilibrium distance, wherein the equilibrium distance is set to be greater than the equilibrium distance set for the FIG. 29B embodiment.

Figure 29D:
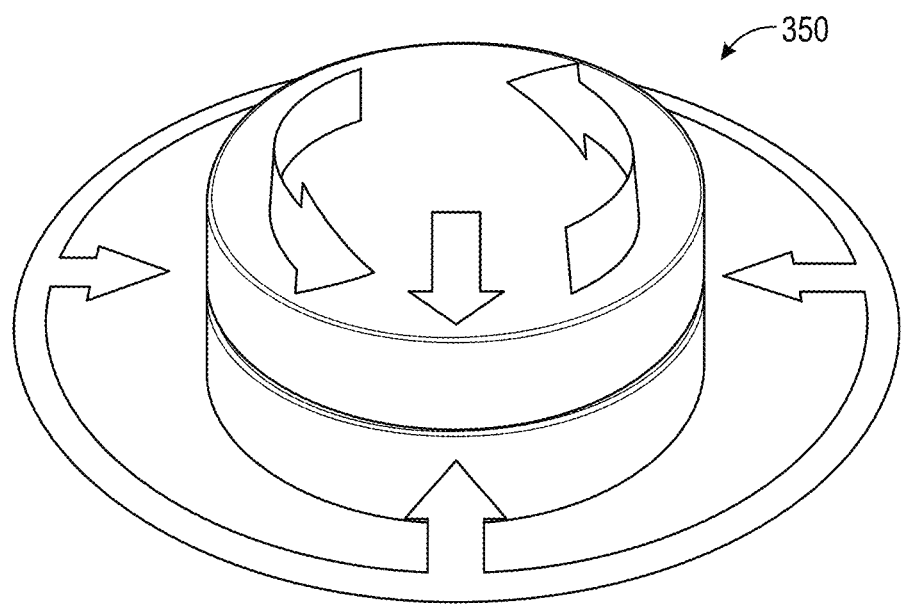

FIG. 29D illustrates two latch polymagnets configured to repel until the magnet pair pass through a defined transition point, and after the transition point, they reverse polarity and attract.

Figure 30A:
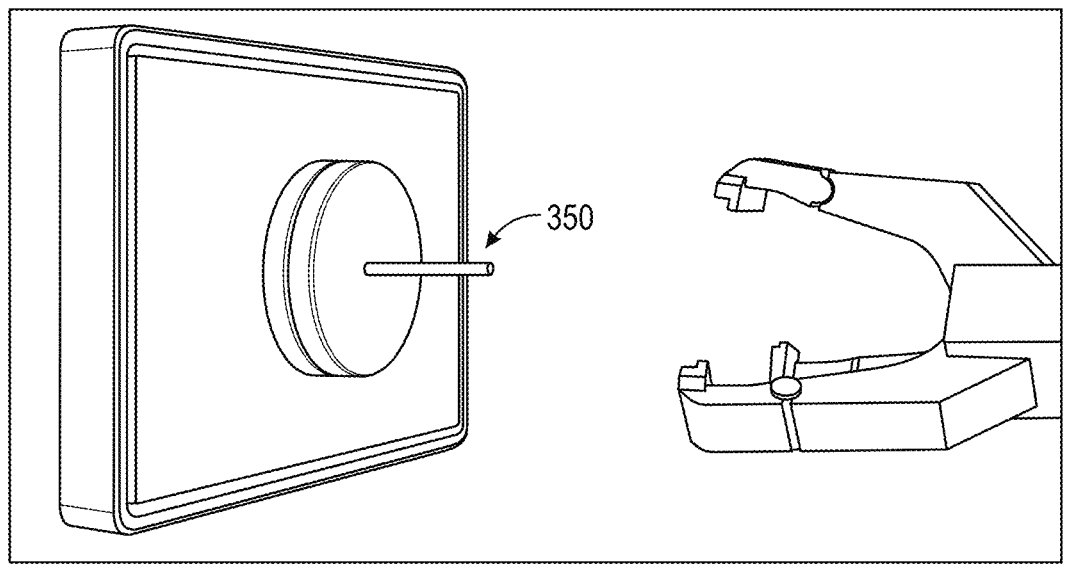
FIGS. 30A and 30B illustrate various aspects of align polymagnets forming part of a CPAP nasal respiratory assembly configured for engaging the nostrils of a patient, in accordance with some embodiments of the presently disclosed subject matter.
Figure 30B:
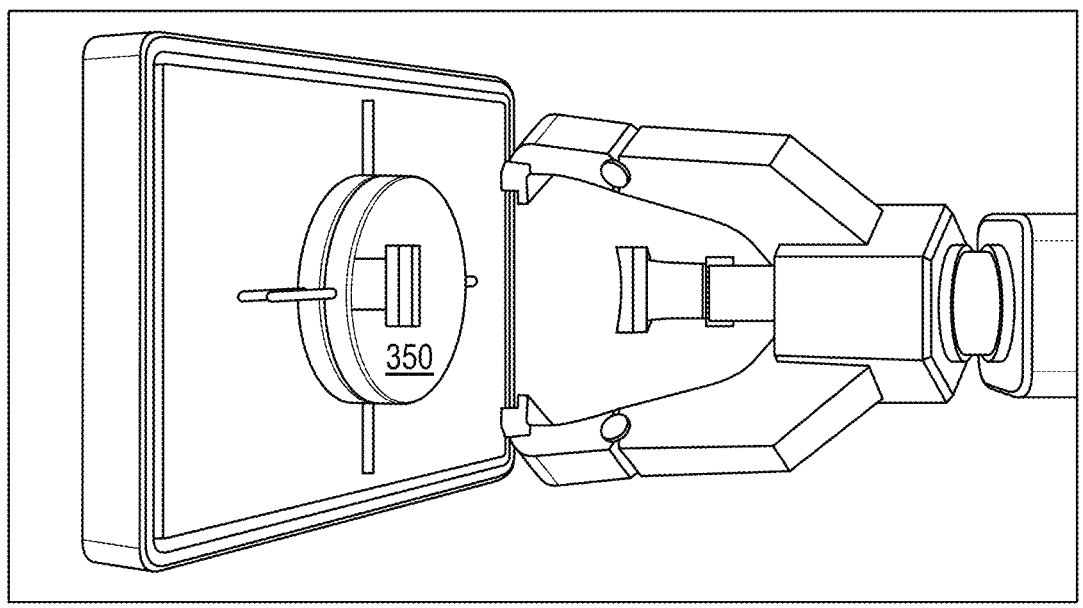
Figure 31A:
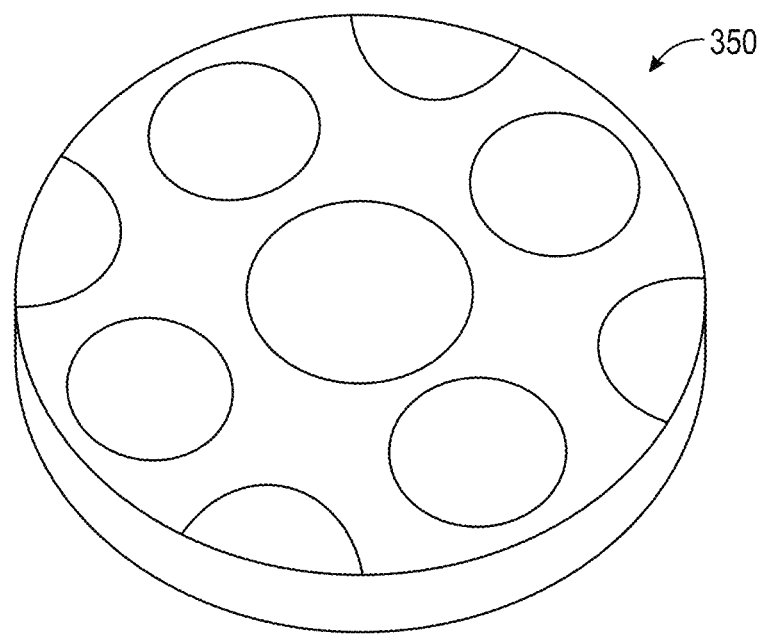
FIGS. 31A and 31F illustrate various patterns programed onto polymagnets forming part of a CPAP nasal respiratory assembly configured for engaging the nostrils of a patient, in accordance with some embodiments of the presently disclosed subject matter.
Figure 31B:
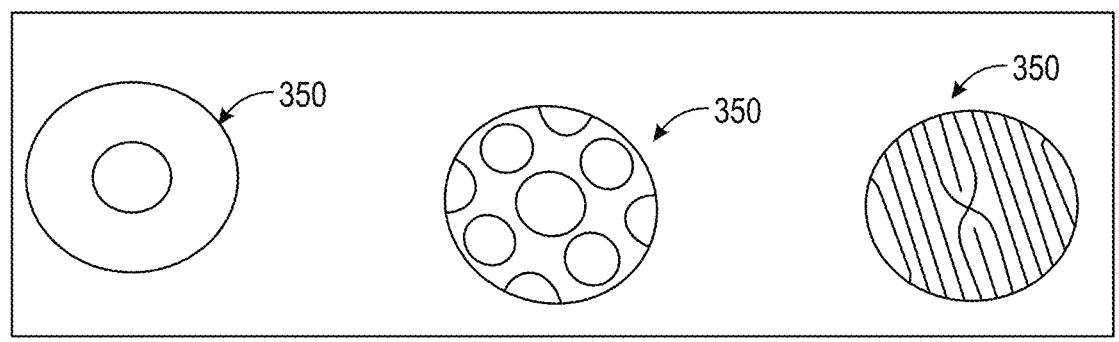
Figure 31C:
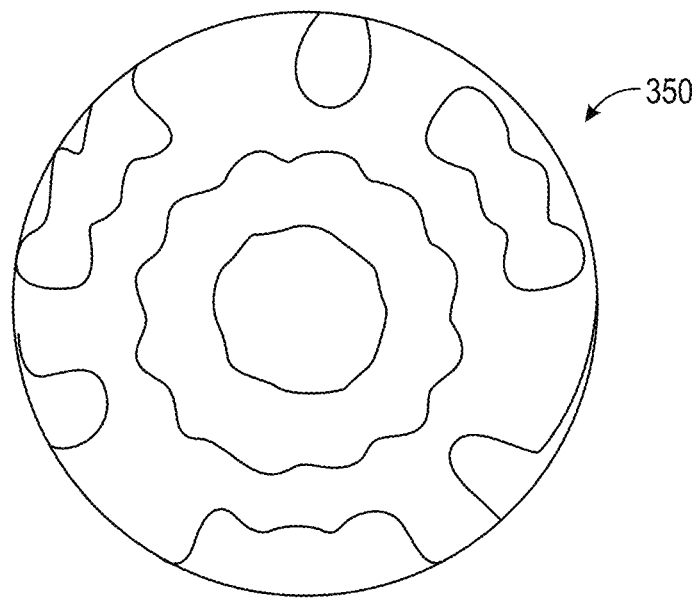
Figure 31D:
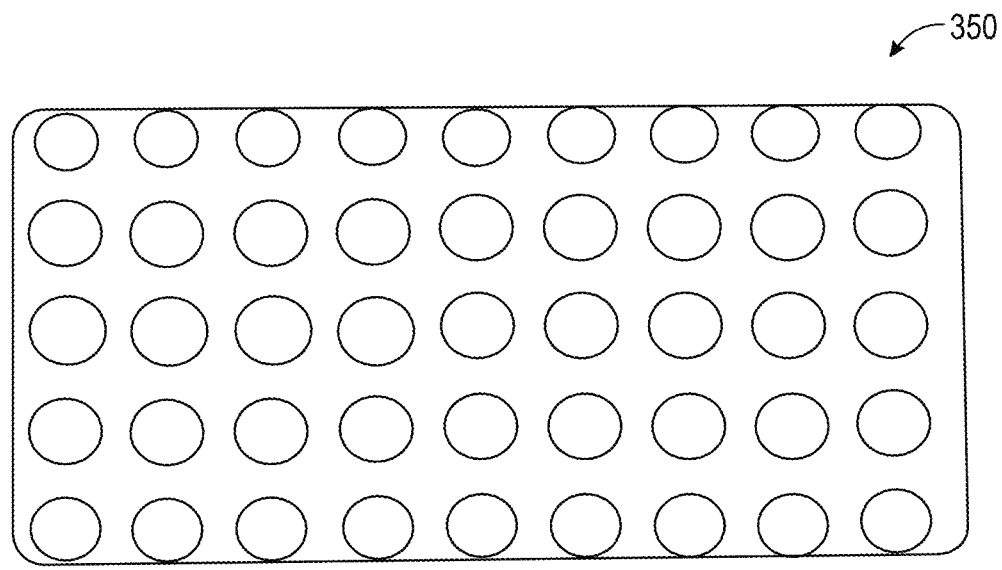
Figure 31E:
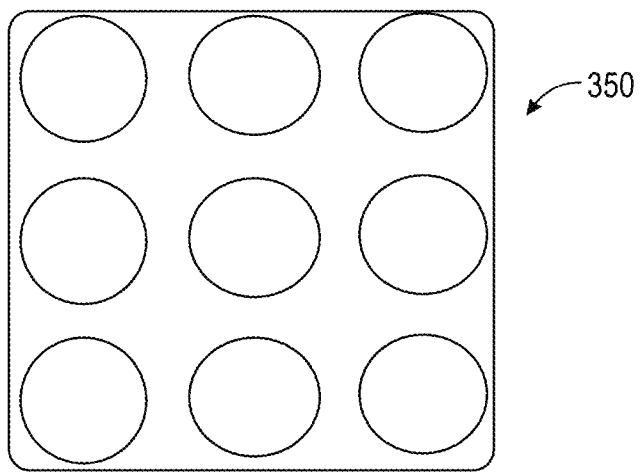
Figure 31F:
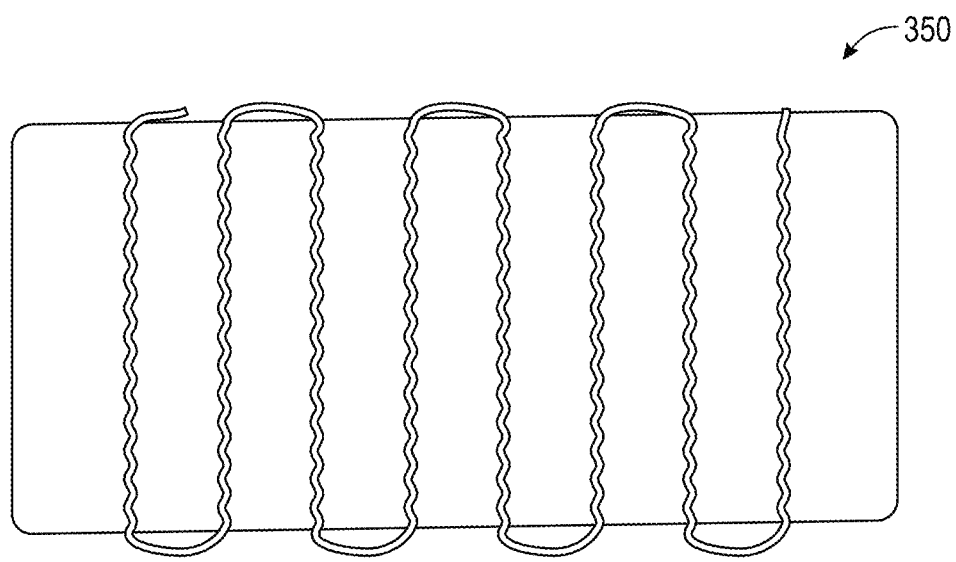

FIG. 30A illustrates two attach polymagnets wherein the magnetic field is designed to be close to the surface of the magnet. This feature provides greater safety from a distance and concentrates the field making it stronger.

While the embodiments have been described in connection with the preferred embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A respiratory assembly for use in conjunction with a continuous positive airway pressure (CPAP) equipment, the respiratory assembly comprising:
   a conduit coupler comprising a male member and a female member and a channel through the conduit coupler comprising an aperture defined in each of the male member and female member;
   a fabric based, disposable respiratory mask defining a central opening therethrough that is sized to receive the male member, wherein the mask is configured to fully cover and enclose a nose and a mouth of a patient;
   a first gasket positioned between the male member and the respiratory mask, the first gasket encircling the central opening to provide a sealing thereto; and
   a nasal respiratory assembly comprising a post having a first end that is selectively affixed to a sheet configured to directly couple to an exterior portion of a patient's nostril, wherein the nasal respiratory assembly is directly connected attached to one of the conduit coupler or tubing disposed through the channel of the conduit coupler and wherein the nasal respiratory assembly is configured to be unattached to the interior of the patient's nostril.

2. The respiratory assembly of claim 1, wherein the respiratory mask is configured for blocking at least 95 percent of particles of 0.3-micron size or greater.

3. The respiratory assembly of claim 1, wherein the respiratory mask is a surgical mask.

4. The respiratory assembly of claim 1, wherein the first gasket comprises an adhesive foam material.

5. The respiratory assembly of claim 1, wherein the first gasket is formed of a stretchable elastomeric material.

6. The respiratory assembly of claim 1, wherein at least one major surface of the first gasket comprises a peel-back glue membrane.

7. The respiratory assembly of claim 1, wherein at least one major surface of the first gasket comprises a glue material.

8. The respiratory assembly of claim 1, wherein respiratory assembly comprises a second gasket disposed between the female member and the respiratory mask, the second gasket encircling the central opening.

9. The respiratory assembly of claim 1, wherein female member selectively engages with the male member.

10. The respiratory assembly of claim 1, wherein both sides of the first gasket comprise an adhesive.

11. The respiratory assembly of claim 1, wherein the central opening comprises a snap-on lid.

12. A respiratory assembly for use in conjunction with a continuous positive airway pressure (CPAP) equipment, the respiratory assembly comprising:
- a respiratory mask defining an opening, wherein the respiratory mask is configured to fully cover and enclose a mouth and a nose of a patient;
- a conduit coupler forming a substantially airtight seal around the opening of the respiratory mask, wherein the conduit coupler comprises:
- a male member and a female member, each defining an aperture for a conduit to fit therethrough, wherein a sleeve of the male member is configured to pass through the opening of the respiratory mask to selectively engage with the female member, a gasket provided between the female member and the respiratory mask such that the gasket forms a substantially airtight seal between the sleeve of the male member and the opening when the male member selectively engages with the female member;

wherein a connector end of the female member is in fluid communication with a channel opening of a fluid source; and a nasal respiratory assembly having a portion a post having a first end that is selectively affixed to a sheet that is configured to directly couple to a patient's nostril, wherein the nasal respiratory assembly is directly connected attached to the conduit coupler and wherein the nasal respiratory assembly is configured to be unattached to the interior of the patient's nostril.

* * * * *